US011203765B2

(12) United States Patent
Song et al.

(10) Patent No.: US 11,203,765 B2
(45) Date of Patent: Dec. 21, 2021

(54) DROUGHT TOLERANT PLANTS

(71) Applicant: University of Florida Research Foundation, Inc., Gainesville, FL (US)

(72) Inventors: Wen-Yuan Song, Gainesville, FL (US); Xiuhua Chen, St. Louis, MO (US); Xiaoen Huang, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 86 days.

(21) Appl. No.: 16/186,954

(22) Filed: Nov. 12, 2018

(65) Prior Publication Data

US 2019/0062776 A1     Feb. 28, 2019

Related U.S. Application Data

(63) Continuation-in-part of application No. PCT/US2017/032502, filed on May 12, 2017.

(60) Provisional application No. 62/335,241, filed on May 12, 2016.

(51) Int. Cl.
    *C12N 15/82*     (2006.01)
    *C07K 14/415*     (2006.01)

(52) U.S. Cl.
    CPC ........ *C12N 15/8273* (2013.01); *C07K 14/415* (2013.01); *C12N 15/8237* (2013.01)

(58) Field of Classification Search
None
See application file for complete search history.

(56) References Cited

U.S. PATENT DOCUMENTS 5,952,485 A * 9/1999 Ronald .............. C12N 15/8281
                                                 435/320.1

FOREIGN PATENT DOCUMENTS

| WO | WO-1999/045129 A1 | 9/1999 | |
|---|---|---|---|
| WO | WO2009127441 | * 10/2009 | ............ C12N 15/82 |
| WO | WO2014113605 | * 7/2014 | ............ C12N 15/82 |
| WO | WO-2015/081061 A2 | 6/2015 | |

OTHER PUBLICATIONS

Gao et al. Do transgenesis and marker-assisted backcross breeding produce substantially equivalent plants? A comparative study of transgenic and backcross rice carrying bacterial blight resistant gene Xa21. BMC Genomics. 2013. 14(738): pp. 1-26.*
GenBank Accession ACC49123. Receptor kinase-like protein [Oryza sativa Indica Group], Published Dec. 14, 1995. pp. 1-2.*
GenBank Accession No. U37133. Oryza sativa receptor kinase-like protein (Xa21) gene, complete cds. Published Dec. 14, 1995. pp. 1-2.*
Sharma et al. Recent advances in dissecting stress-regulatory crosstalk in rice. Molecular Plant. 2013. 6(2): 250-260.*

(Continued)

*Primary Examiner* — Ashley K Buran
(74) *Attorney, Agent, or Firm* — Alston & Bird

(57) ABSTRACT

Described are methods and compositions for enhancing drought tolerance in plants. Nucleic acid constructs therefore are also described. Transgenic plants are also provided that exhibit enhanced agronomic properties. The inventors have demonstrated increased drought tolerance in connection with increased expression of the Xa21 gene.

20 Claims, 26 Drawing Sheets

Specification includes a Sequence Listing.

(56) References Cited

OTHER PUBLICATIONS

Park et al. Identification of rice genes involved in variety-specific tolerance to drought and phosphorous-deficiency. ETH Zurich. 2014. pp. 1-135.*

Rabbani et al. Monitoring expression profiles of rice genes under cold, drought, and high-salinity stresses and abscisic acid application of using cDNA microarray and RNA gel-blot analyses. Plant Physiology. 2003. 133: pp. 1755-1767.*

Liu et al. OsWRKY71, a rice transcription factor, is involved in rice defense response. Journal of Plant Physiology. 2007. 164: 969-979.*

Zhang et al. Overlap between Signaling Pathways Responsive to Xanthomonas oryzae pv. oryzae Infection and Drought Stress in Rice Introgression Line Revealed by RNA-Seq. Journal of Plant Growth Regul. 2016 (published online Sep. 14, 2015). 35:345-356.*

Kumar et al. Leaf gas exchange physiology in rice genotypes infected with bacterial blight: An attempt to link photosynthesis with disease severity and rice yield. Australian Journal of Crop Science. 2013. 7(1):32-39.*

Vemanna et al. Cross-Talk Signaling in Rice During Combined Drought and Bacterial Blight Stress. Frontiers in Plant Science. 2019. 10(193): 1-11.*

Wang et al., "Rice XA21 Binding Protein 3 Is a Ubiquitin Ligase Required for Full Xa21-Mediated Disease Resistance," Plant Cell., 18(12): 3635-3646, (2006).

International Search Report and Written Opinion for PCT/US2017/032502, dated Aug. 22, 2017.

* cited by examiner

Before Drought

Drought + recovery

SEQUENCE LISTING

```
<160> NUMBER OF SEQ ID NOS: 31

<210> SEQ ID NO 1
<211> LENGTH: 3078
<212> TYPE: DNA
<213> ORGANISM: Oryza sativa L.

<400> SEQUENCE: 1
atgatatcac tcccattatt gctcttcgtc ctgttgttct ctgcgctgct gctctgccct        60
tcaagcagtg acgacgatgg tgatgctgcc ggcgacgaac tcgcgctgct ctctttcaag       120
tcatccctgc tataccaggg gggccagtcg ctggcatctt ggaacacgtc cggccacggc       180
cagcactgca catgggtggg tgttgtgtgc ggccgccgcc gccgccggca cccacacagg       240
gtggtgaagc tgctgctgcg ctcctccaac ctgtccggga tcatctcgcc gtcgctcggc       300
aacctgtcct tcctcaggga gctggacctc ggcgacaact acctctccgg cgagatacca       360
ccggagctca gccgtctcag caggcttcag ctgctggagc tgagcgataa ctccatccaa       420
gggagcatcc ccgcggccat ggagcatgc accaagttga catcgctaga cctcagccac       480
aaccaactgc gaggtatgat cccacgtgag attggtgcca gcttgaaaca tctctcgaat       540 ttgtacctt acaaaaatgg tttgtcagga gagattccat ccgctttggg caatctcact       600
agcctccagg agtttgattt gagcttcaac agattatcag gagctatacc ttcatcactg       660
gggcagctca gcagtctatt gactatgaat ttgggacaga acaatctaag tgggatgatc       720
cccaattcta tctggaacct ttcgtctcta agagcgttta gtgtcagaga aaacaagcta       780
ggtggtatga tccctacaaa tgcattcaaa acccttcacc tcctcgaggt gatagatatg       840
ggcactaacc gtttccatgg caaaatccct gcctcagttg ctaatgcttc tcatttgaca       900
gtgattcaga tttatggcaa cttgttcagt ggaattatca cctcggggtt tggaaggtta       960
agaaatctca cagaactgta tctctggaga aatttgtttc aaactagaga acaagatgat      1020
```

```
tgggggttca tttctgacct aacaaattgc tccaaattac aaacattgaa cttgggagaa    1080
aataacctgg ggggagttct tcctaattcg ttttccaatc tttccacttc gcttagtttt    1140
cttgcacttg aattgaataa gatcacagga agcattccga aggatattgg caatcttatt    1200
ggcttacaac atctctatct ctgcaacaac aatttcagag ggtctcttcc atcatcgttg    1260
ggcaggctta aaaacttagg cattctactc gcctacgaaa acaacttgag cggttcgatc    1320
ccgttggcca taggaaatct tactgaactt aatatcttac tgctcggcac caacaaattc    1380
agtggttgga taccatacac actctcaaac ctcacaaact tgttgtcatt aggcctttca    1440
actaataacc ttagtggtcc aatacccagt gaattattca atattcaaac actatcaata    1500
atgatcaatg tatcaaaaaa taacttggag ggatcaatac cacaagaaat agggcatctc    1560
aaaaatctag tagaatttca tgcagaatcg aatagattat caggtaaaat ccctaacacg    1620
cttggtgatt gccagctctt acggtatctt tatctgcaaa ataatttgtt atctggtagc    1680
atcccatcag ccttgggtca gctgaaaggt ctcgaaactc ttgatctctc aagcaacaat    1740
ttgtcaggcc agatacccac atccttagca gatattacta tgcttcattc cttgaacctt    1800
tctttcaaca gctttgtggg ggaagtgcca accattggtg ctttcgcagc tgcatccggg    1860
atctcaatcc aaggcaatgc caaactctgt ggtggaatac ctgatctaca tctgcctcga    1920
tgttgtccat tactagagaa cagaaaacat ttcccagttc tacctatttc tgtttctctg    1980
gccgcagcac tggccatcct ctcatcactc tacttgctta taacctggca aagagaact    2040 aaaaagggag ccccttcaag aacttccatg aaaggccacc cattggtctc ttattcgcag    2100
ttggtaaaag caacagatgg tttcgcgccg accaatttgt tgggttctgg atcatttggc    2160
tcagtataca aaggaaagct taatatccaa gatcatgttg cagtgaaggt actaaagctt    2220
gaaaatccta aggcgctcaa gagtttcact gccgaatgtg aagcactacg aaatatgcga    2280
catcgaaatc ttgtcaagat agttacaatt gctcgagca ttgataacag agggaacgat    2340
ttcaaagcaa ttgtgtatga cttcatgccc aacggcagtc tggaagattg gatacaccct    2400
gaaacaaatg atcaagcaga ccagaggcac ttgaatctgc atcgaagagt gaccatacta    2460
cttgatgttg cctgcgcact ggactatctt caccgccatg gccctgaacc tgttgtacac    2520
tgtgatatta aatcaagcaa tgtgctgtta gattctgata tggtagccca tgttggagat    2580
tttgggcttg caagaatact tgttgatggg acctcattga tacaacagtc aacaagctcg    2640
atgggattta tagggacaat tggctatgca gcaccagagt atggcgttgg gctcattgca    2700
tcaacgcatg gagatatttta cagctatgga attctagtgc tggaaatagt aaccgggaag    2760
cggccaactg acagtacatt cagacccgat ttgggcctcc gtcagtacgt tgaactgggc    2820
ctacatggca gagtgacgga tgttgttgac acgaagctca ttttggattc tgagaactgg    2880
ctgaacagta caaataattc tccatgtaga agaatcactg aatgcattgt ttggctgctt    2940
agacttgggt tgtcttgctc tcaggaattg ccatcgagta gaacgccaac cggagatatc    3000
atcgacgaac tgaatgccat caaacagaat ctctccggat tgtttccagt gtgtgaaggt    3060
gggagccttg aattctga                                                    3078
```

<210> SEQ ID NO 2
<211> LENGTH: 1025
<212> TYPE: PRT
<213> ORGANISM: Oryza sativa L.

<400> SEQUENCE: 2

```
Met Ile Ser Leu Pro Leu Leu Leu Phe Val Leu Leu Phe Ser Ala Leu
  1               5                  10                  15

Leu Leu Cys Pro Ser Ser Asp Asp Asp Gly Asp Ala Ala Gly Asp
         20                  25                  30

Glu Leu Ala Leu Leu Ser Phe Lys Ser Ser Leu Leu Tyr Gln Gly Gly
             35                  40                  45

Gln Ser Leu Ala Ser Trp Asn Thr Ser Gly His Gly Gln His Cys Thr
     50                  55                  60

Trp Val Gly Val Val Cys Gly Arg Arg Arg Arg His Pro His Arg
 65              70                  75                  80

Val Val Lys Leu Leu Arg Ser Ser Asn Leu Ser Gly Ile Ile Ser
             85                  90                  95

Pro Ser Leu Gly Asn Leu Ser Phe Leu Arg Glu Leu Asp Leu Gly Asp
             100                 105                 110

Asn Tyr Leu Ser Gly Glu Ile Pro Pro Glu Leu Ser Arg Leu Ser Arg
             115                 120                 125

Leu Gln Leu Leu Glu Leu Ser Asp Asn Ser Ile Gln Gly Ser Ile Pro
         130                 135                 140

Ala Ala Ile Gly Ala Cys Thr Lys Leu Thr Ser Leu Asp Leu Ser His
145                 150                 155                 160

Asn Gln Leu Arg Gly Met Ile Pro Arg Glu Ile Gly Ala Ser Leu Lys
             165                 170                 175

His Leu Ser Asn Leu Tyr Leu Tyr Lys Asn Gly Leu Ser Gly Glu Ile
             180                 185                 190

Pro Ser Ala Leu Gly Asn Leu Thr Ser Leu Gln Glu Phe Asp Leu Ser
     195                 200                 205

Phe Asn Arg Leu Ser Gly Ala Ile Pro Ser Ser Leu Gly Gln Leu Ser
     210                 215                 220

Ser Leu Leu Thr Met Asn Leu Gly Gln Asn Asn Leu Ser Gly Met Ile
225                 230                 235                 240

Pro Asn Ser Ile Trp Asn Leu Ser Ser Leu Arg Ala Phe Ser Val Arg
             245                 250                 255

Glu Asn Lys Leu Gly Gly Met Ile Pro Thr Asn Ala Phe Lys Thr Leu
             260                 265                 270

His Leu Leu Glu Val Ile Asp Met Gly Thr Asn Arg Phe His Gly Lys
             275                 280                 285

Ile Pro Ala Ser Val Ala Asn Ala Ser His Leu Thr Val Ile Gln Ile
             290                 295                 300

Tyr Gly Asn Leu Phe Ser Gly Ile Ile Thr Ser Gly Phe Gly Arg Leu
305                 310                 315                 320

Arg Asn Leu Thr Glu Leu Tyr Leu Trp Arg Asn Leu Phe Gln Thr Arg
             325                 330                 335

Glu Gln Asp Asp Trp Gly Phe Ile Ser Asp Leu Thr Asn Cys Ser Lys
             340                 345                 350

Leu Gln Thr Leu Asn Leu Gly Glu Asn Asn Leu Gly Gly Val Leu Pro
             355                 360                 365

Asn Ser Phe Ser Asn Leu Ser Thr Ser Leu Ser Phe Leu Ala Leu Glu
             370                 375                 380

Leu Asn Lys Ile Thr Gly Ser Ile Pro Lys Asp Ile Gly Asn Leu Ile
385                 390                 395                 400

Gly Leu Gln His Leu Tyr Leu Cys Asn Asn Phe Arg Gly Ser Leu
             405                 410                 415

Pro Ser Ser Leu Gly Arg Leu Lys Asn Leu Gly Ile Leu Leu Ala Tyr
```

-continued

```
                420                 425                 430
Glu Asn Asn Leu Ser Gly Ser Ile Pro Leu Ala Ile Gly Asn Leu Thr
            435                 440                 445
Glu Leu Asn Ile Leu Leu Gly Thr Asn Lys Phe Ser Gly Trp Ile
        450                 455                 460
Pro Tyr Thr Leu Ser Asn Leu Thr Asn Leu Leu Ser Leu Gly Leu Ser
465                 470                 475                 480
Thr Asn Asn Leu Ser Gly Pro Ile Pro Ser Glu Leu Phe Asn Ile Gln
                485                 490                 495
Thr Leu Ser Ile Met Ile Asn Val Ser Lys Asn Asn Leu Glu Gly Ser
            500                 505                 510
Ile Pro Gln Glu Ile Gly His Leu Lys Asn Leu Val Glu Phe His Ala
        515                 520                 525
Glu Ser Asn Arg Leu Ser Gly Lys Ile Pro Asn Thr Leu Gly Asp Cys
    530                 535                 540
Gln Leu Leu Arg Tyr Leu Tyr Leu Gln Asn Asn Leu Leu Ser Gly Ser
545                 550                 555                 560
Ile Pro Ser Ala Leu Gly Gln Leu Lys Gly Leu Glu Thr Leu Asp Leu
                565                 570                 575
Ser Ser Asn Asn Leu Ser Gly Gln Ile Pro Thr Ser Leu Ala Asp Ile
            580                 585                 590
Thr Met Leu His Ser Leu Asn Leu Ser Phe Asn Ser Phe Val Gly Glu
        595                 600                 605
Val Pro Thr Ile Gly Ala Phe Ala Ala Ala Ser Gly Ile Ser Ile Gln
    610                 615                 620
Gly Asn Ala Lys Leu Cys Gly Gly Ile Pro Asp Leu His Leu Pro Arg
625                 630                 635                 640
Cys Cys Pro Leu Leu Glu Asn Arg Lys His Phe Pro Val Leu Pro Ile
                645                 650                 655
Ser Val Ser Leu Ala Ala Ala Leu Ala Ile Leu Ser Ser Leu Tyr Leu
            660                 665                 670
Leu Ile Thr Trp His Lys Arg Thr Lys Lys Gly Ala Pro Ser Arg Thr
        675                 680                 685
Ser Met Lys Gly His Pro Leu Val Ser Tyr Ser Gln Leu Val Lys Ala
    690                 695                 700
Thr Asp Gly Phe Ala Pro Thr Asn Leu Leu Gly Ser Gly Ser Phe Gly
705                 710                 715                 720
Ser Val Tyr Lys Gly Lys Leu Asn Ile Gln Asp His Val Ala Val Lys
                725                 730                 735
Val Leu Lys Leu Glu Asn Pro Lys Ala Leu Lys Ser Phe Thr Ala Glu
            740                 745                 750
Cys Glu Ala Leu Arg Asn Met Arg His Arg Asn Leu Val Lys Ile Val
        755                 760                 765
Thr Ile Cys Ser Ser Ile Asp Asn Arg Gly Asn Asp Phe Lys Ala Ile
    770                 775                 780
Val Tyr Asp Phe Met Pro Asn Gly Ser Leu Glu Asp Trp Ile His Pro
785                 790                 795                 800
Glu Thr Asn Asp Gln Ala Asp Gln Arg His Leu Asn Leu His Arg Arg
                805                 810                 815
Val Thr Ile Leu Leu Asp Val Ala Cys Ala Leu Asp Tyr Leu His Arg
            820                 825                 830
His Gly Pro Glu Pro Val Val His Cys Asp Ile Lys Ser Ser Asn Val
        835                 840                 845
```

```
Leu Leu Asp Ser Asp Met Val Ala His Val Gly Asp Phe Gly Leu Ala
    850                 855                 860

Arg Ile Leu Val Asp Gly Thr Ser Leu Ile Gln Gln Ser Thr Ser Ser
865                 870                 875                 880

Met Gly Phe Ile Gly Thr Ile Gly Tyr Ala Ala Pro Glu Tyr Gly Val
            885                 890                 895

Gly Leu Ile Ala Ser Thr His Gly Asp Ile Tyr Ser Tyr Gly Ile Leu
            900                 905                 910

Val Leu Glu Ile Val Thr Gly Lys Arg Pro Thr Asp Ser Thr Phe Arg
        915                 920                 925

Pro Asp Leu Gly Leu Arg Gln Tyr Val Glu Leu Gly Leu His Gly Arg
    930                 935                 940

Val Thr Asp Val Val Asp Thr Lys Leu Ile Leu Asp Ser Glu Asn Trp
945                 950                 955                 960

Leu Asn Ser Thr Asn Asn Ser Pro Cys Arg Arg Ile Thr Glu Cys Ile
                965                 970                 975

Val Trp Leu Leu Arg Leu Gly Leu Ser Cys Ser Gln Glu Leu Pro Ser
            980                 985                 990

Ser Arg Thr Pro Thr Gly Asp Ile  Ile Asp Glu Leu Asn  Ala Ile Lys
        995                 1000                1005

Gln Asn  Leu Ser Gly Leu Phe  Pro Val Cys Glu Gly  Gly Ser Leu
    1010                1015                1020

Glu Phe
    1025

<210> SEQ ID NO 3
<211> LENGTH: 26
<212> TYPE: DNA
<213> ORGANISM: Artificial Sequence
<220> FEATURE:
<223> OTHER INFORMATION: PCR primer

<400> SEQUENCE: 3
ctttccgaag acgagtatat ctaacg                                          26

<210> SEQ ID NO 4
<211> LENGTH: 29
<212> TYPE: DNA
<213> ORGANISM: Artificial Sequence
<220> FEATURE:
<223> OTHER INFORMATION: PCR primer

<400> SEQUENCE: 4
actagtggta cccgtcttat atcgcctca                                       29

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ggaatgtgga cggtgacact                                                 20

<210> SEQ ID NO 6
<211> LENGTH: 27
<212> TYPE: DNA
<213> ORGANISM: Artificial Sequence
<220> FEATURE:
```

<223> OTHER INFORMATION: PCR primer

<400> SEQUENCE: 6
tcaaaataga gtccagtaga tttgtca                                           27

<210> SEQ ID NO 7
<211> LENGTH: 22
<212> TYPE: DNA
<213> ORGANISM: Artificial Sequence
<220> FEATURE:
<223> OTHER INFORMATION: PCR primer

<400> SEQUENCE: 7
gtacatctag atttggggta ga                                                22

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
gtacgaacac aagctaacac ga                                                22

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
ccaagcagaa gaccgccga                                                    19

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
gtcatcccca gcgtgctca                                                    19

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
cgatgacgac gctgagtgaa                                                   20

<210> SEQ ID NO 12
<211> LENGTH: 21
<212> TYPE: DNA
<213> ORGANISM: Artificial Sequence
<220> FEATURE:
<223> OTHER INFORMATION: PCR primer

<400> SEQUENCE: 12
caggtgacat cacacgcttg a                                                 21

```
<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
taacagcacc accaccacaa                                               20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
gtcttcaagc tgttcgacgg                                               20

<210> SEQ ID NO 15
<211> LENGTH: 13
<212> TYPE: PRT
<213> ORGANISM: Artificial sequence
<220> FEATURE:
<223> OTHER INFORMATION: Antibody tags

<400> SEQUENCE: 15

Glu Gln Lys Leu Ile Ser Glu Glu Asp Leu Leu Glu Lys
1               5                   10

<210> SEQ ID NO 16
<211> LENGTH: 28
<212> TYPE: PRT
<213> ORGANISM: Artificial sequence
<220> FEATURE:
<223> OTHER INFORMATION: Antibody tags

<400> SEQUENCE: 16

Asp Tyr Lys Asp Asp Asp Asp Lys Gly Gly Asp Tyr Lys Asp Asp Asp
1               5                   10                  15

Asp Lys Gly Gly Asp Tyr Lys Asp Asp Asp Asp Lys
            20                  25

<210> SEQ ID NO 17
<211> LENGTH: 8
<212> TYPE: PRT
<213> ORGANISM: Artificial sequence
<220> FEATURE:
<223> OTHER INFORMATION: Antibody tags

<400> SEQUENCE: 17

Pro Lys Lys Lys Arg Lys Val Gly
1               5

<210> SEQ ID NO 18
<211> LENGTH: 24
<212> TYPE: DNA
<213> ORGANISM: Artificial sequence
<220> FEATURE:
<223> OTHER INFORMATION: PCR primer

<400> SEQUENCE: 18
ctggatcatt tggctcagta taca                                          24

<210> SEQ ID NO 19
```

```
<211> LENGTH: 22
<212> TYPE: DNA
<213> ORGANISM: Artificial sequence
<220> FEATURE:
<223> OTHER INFORMATION: PCR primer

<400> SEQUENCE: 19
aaattcaagg ctcccacctt ca                                              22

<210> SEQ ID NO 20
<211> LENGTH: 44
<212> TYPE: DNA
<213> ORGANISM: Artificial sequence
<220> FEATURE:
<223> OTHER INFORMATION: PCR primer

<400> SEQUENCE: 20
ggtgggagcc ttgaatttgt cgacatggtg agcaagggcg agga                      44

<210> SEQ ID NO 21
<211> LENGTH: 58
<212> TYPE: DNA
<213> ORGANISM: Artificial sequence
<220> FEATURE:
<223> OTHER INFORMATION: PCR primer

<400> SEQUENCE: 21
tgatcgtgtg gtagatacca ctgcagtcag tcgaccttgt acagctcgtc catgccga       58

<210> SEQ ID NO 22
<211> LENGTH: 64
<212> TYPE: DNA
<213> ORGANISM: Artificial sequence
<220> FEATURE:
<223> OTHER INFORMATION: PCR primer

<400> SEQUENCE: 22
gtgtggatcc atgggtcacg gtgtcagctg cgcccgcacc cctagggtga gcaagggcga     60
ggag                                                                  64

<210> SEQ ID NO 23
<211> LENGTH: 24
<212> TYPE: DNA
<213> ORGANISM: Artificial sequence
<220> FEATURE:
<223> OTHER INFORMATION: PCR primer

<400> SEQUENCE: 23
gaatagggaa ttctcccagc cgaa                                            24

<210> SEQ ID NO 24
<211> LENGTH: 40
<212> TYPE: DNA
<213> ORGANISM: Artificial sequence
<220> FEATURE:
<223> OTHER INFORMATION: PCR primer

<400> SEQUENCE: 24
gttctagagg atccatggct cacggtgtca gctgcgcccg                           40

<210> SEQ ID NO 25
<211> LENGTH: 40
<212> TYPE: DNA
<213> ORGANISM: Artificial sequence
<220> FEATURE:
<223> OTHER INFORMATION: PCR primer
```

<400> SEQUENCE: 25
gttctagaag atcttcatag atcgtgctca ggcttgtcca					40

<210> SEQ ID NO 26
<211> LENGTH: 65
<212> TYPE: DNA
<213> ORGANISM: Artificial sequence
<220> FEATURE:
<223> OTHER INFORMATION: PCR primer

<400> SEQUENCE: 26
tgacaagccg tcatccctgc aactcacccg ggaggagtcg gaacgatctc acaacctcag			60 tgagg					65

<210> SEQ ID NO 27
<211> LENGTH: 65
<212> TYPE: DNA
<213> ORGANISM: Artificial sequence
<220> FEATURE:
<223> OTHER INFORMATION: PCR primer

<400> SEQUENCE: 27
cctcactgag gttgtgagat cgttccgact cctcccgggt gagttgcagg gatgacggct			60 tgtca					65

<210> SEQ ID NO 28
<211> LENGTH: 38
<212> TYPE: DNA
<213> ORGANISM: Artificial sequence
<220> FEATURE:
<223> OTHER INFORMATION: PCR primer

<400> SEQUENCE: 28
gtgttctaga actagtatgg cctcctccga ggacgtca					38

<210> SEQ ID NO 29
<211> LENGTH: 61
<212> TYPE: DNA
<213> ORGANISM: Artificial sequence
<220> FEATURE:
<223> OTHER INFORMATION: PCR primer

<400> SEQUENCE: 29
gtgttctaga ctatcccacc ttacgctttt tcttaggtcc caggaacagg tggtggcggc			60 c					61

<210> SEQ ID NO 30
<211> LENGTH: 45
<212> TYPE: DNA
<213> ORGANISM: Artificial sequence
<220> FEATURE:
<223> OTHER INFORMATION: PCR primer

<400> SEQUENCE: 30
gtgcggccgc actagtggcg gaatggtgag caagggcgag gagga					45

```
<210> SEQ ID NO 31
<211> LENGTH: 34
<212> TYPE: DNA
<213> ORGANISM: Artificial sequence
<220> FEATURE:
<223> OTHER INFORMATION: PCR primer

<400> SEQUENCE: 31 gtagatctttacttgtacagctcgtccatgccgc                                34
```

DROUGHT TOLERANT PLANTS

CROSS-REFERENCE TO RELATED APPLICATIONS

This application is a Continuation-in-Part of International Application PCT/US2017/032502, filed May 12, 2017, which claims the benefit of U.S. Provisional Application No. 62/335,241, filed on May 12, 2016, the entire disclosures of which are incorporated herein by reference.

STATEMENT REGARDING FEDERALLY SPONSORED RESEARCH OR DEVELOPMENT

This invention was made with government support under Grant 1444456 awarded by the National Science Foundation and under Grant 2011-67003-30215 awarded by the United States Department of Agriculture. The government has certain rights in the invention.

INCORPORATION OF SEQUENCE LISTINGS

The sequence listing that is contained in the file named 519547_SeqListing_ST25.txt, which is 18 kilobytes (as measured in Microsoft Windows®) and was created on Sep. 24, 2018, is filed herewith by electronic submission and is incorporated by reference herein.

FIELD

The present disclosure relates generally to the field of molecular biology. More specifically, the disclosure relates to plant genes involved in drought tolerance and methods of use thereof.

BACKGROUND

Drought is a major constraint to crop production worldwide. The greenhouse effect is predicted to raise temperatures and to prolong droughts. Human-induced climate change is predicted to put pressure on the supply of water for agriculture. At the same time the world population is estimated to exceed 9.5 billion by the year 2050. Therefore, central to long-term agricultural security is implementing a sustainable system that is more resilient and productive, while at the same time requires less of the increasingly costly inputs such as water.

SUMMARY

The present disclosure provides methods of increasing drought tolerance in a plant, comprising expressing in the plant a heterologous receptor kinase Xa21 coding region, wherein the drought tolerance of the plant is increased when compared to a control plant that lacks the expressing of the heterologous Xa21 coding region. In some embodiments the expressing comprises introducing into the plant a DNA construct comprising the heterologous receptor kinase Xa21 coding region operably linked to a native receptor kinase Xa21 promoter. In some embodiments the expressing comprises introducing into the plant a DNA construct comprising the heterologous receptor kinase Xa21 coding region operably linked to a heterologous promoter functional in the plant. The promoter can be, but is no limited to, a constitutive or an inducible promoter.

In some embodiments, methods for increasing drought tolerance in a plant during dehydration stress are described. Such methods can comprise expressing in one or more plants a heterologous Xa21 coding region, subjecting the one or more plants to dehydration stress, and selecting a plant having increased drought tolerance when compared to a plant that lacks the heterologous Xa21 coding region. Dehydration stress includes drought, moderate drought, drought stress, or water-limiting conditions.

In some embodiments, the heterologous receptor kinase Xa21 coding region comprises a polynucleotide sequence at least 85%, 90%, 95%, 97%, 98% 99%, or 100% identical to the rice receptor kinase Xa21 coding region (SEQ ID NO: 1, Xa21 gene sequence), or an ortholog or homolog thereof. In some embodiments the heterologous receptor kinase Xa21 coding region comprises a polynucleotide sequence encoding an XA21 protein at least 90%, 95%, 97%, 98%, 99% or 100% identical to the rice receptor kinase XA21 protein (SEQ ID NO: 2), or an ortholog or homolog thereof.

In some embodiments, the plant is a monocotyledonous plant, such as a monocotyledonous plant selected from the group consisting of maize, wheat, rice, sorghum (*Sorghum bicolor*), oats, barley, sugar cane, African oil palm (*Elaeis guineensis*), or switchgrass. In other embodiments, the plant is a dicotyledonous plant, such as a dicotyledonous plant selected from the group consisting of *Arabidopsis*, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp.

In some embodiments, a plant, or part thereof, expressing a heterologous receptor kinase Xa21 coding region is provided, wherein drought tolerance of the plant or part thereof is increased when compared to a control plant or part thereof that lacks the expressing of the heterologous Xa21 coding region. In some embodiments, the expressing comprises introducing into the plant or part thereof a DNA construct comprising the heterologous receptor kinase Xa21 coding region operably linked to a native receptor kinase Xa21 promoter. In some embodiments, the overexpressing comprises introducing into the plant or part thereof a DNA construct comprising the heterologous receptor kinase Xa21 coding region operably linked to a heterologous promoter functional in the plant or part thereof. In some embodiments, the part thereof is a cell, meristem, root, leaf, node, pistil, anther, flower, seed, embryo, stalk or petiole.

In some embodiments, methods of producing food for human or animal consumption are provided, comprising obtaining a plant, or part thereof, expressing a heterologous receptor kinase Xa21 coding region, wherein drought tolerance of the plant or part thereof is increased when compared to a control plant or part thereof that lacks the expressing, and preparing food for human or animal consumption from the plant or part thereof. In some aspects, the food is starch, protein, meal, flour or grain. In some embodiments, methods of producing food for human or animal consumption are provided, comprising expressing in one or more plants a heterologous Xa21 coding region, subjecting the one or more plants to dehydration stress, and selecting a plant having increased drought tolerance when compared to a plant that lacks the heterologous Xa21 coding region, wherein increased drought tolerance provide increased production of food. Dehydration stress includes drought, moderate drought, drought stress, or water-limiting conditions.

In some embodiments, methods of increasing drought tolerance in a rice plant are provided, comprising introducing into the rice plant a DNA construct comprising the rice receptor kinase Xa21 coding region or a heterologous receptor kinase Xa21 coding region operably linked to a heterologous promoter functional in the rice plant, wherein the drought tolerance of the rice plant is increased when compared to a control rice plant that lacks the Xa21 coding region or heterologous Xa21 coding region. In some embodiments, methods for increasing drought tolerance in a rice plant during dehydration stress are described, comprising expressing in one or more rice plants a heterologous Xa21 coding region, subjecting the one or more rice plants to dehydration stress, and selecting a rice plant having increased drought tolerance when compared to a rice plant that lacks the heterologous Xa21 coding region. Dehydration stress includes, drought, moderate drought, drought stress or water-limiting conditions.

In some embodiments, methods of producing a drought tolerant plant are provided, comprising crossing a first plant, said first plant expressing a heterologous receptor kinase Xa21 coding region and selected for increased drought tolerance when compared to a control plant that lacks the expressing of the heterologous Xa21 coding region, with a second plant to produce at least a first progeny plant selected to contain the heterologous Xa21 coding region and/or increased drought tolerance when compared to a control plant that lacks the expressing of the heterologous Xa21 coding region. In some embodiments, the drought tolerant plant is a drought tolerant rice plant.

In some embodiments, methods of increasing drought tolerance in a plant are provided, comprising introducing into the plant a DNA construct comprising a heterologous receptor kinase Xa21 coding region operably linked to a promoter, and selecting a progeny plant that has increased drought tolerance when compared to a control plant that lacks the DNA construct. In some embodiments, the promoter is a native Xa21 gene promoter. In some embodiments, the promoter is a heterologous promoter. In some embodiments, the promoter is an inducible promoter. In some embodiments the inducible promoter is a drought-inducible promoter. In some embodiments, the promoter is a constitutive promoter In some embodiments, methods for improving survival of a plant during dehydration stress are described. Such methods can comprise expressing in one or more plants a heterologous Xa21 coding region, subjecting the one or more plants to dehydration stress, and selecting a plant having increased survival during dehydration stress when compared to a plant that lacks the heterologous Xa21 coding region. Dehydration stress includes drought, moderate drought, drought stress, or water-limiting conditions.

In some embodiments, methods for increasing expression of one or more genes related to desiccation tolerance, biosynthesis of cell walls, and/or transcellular water movement in a plant in response to dehydration stress are described. Such methods can comprise expressing in one or more plants a heterologous Xa21 coding region, subjecting the one or more plants to dehydration stress, and selecting a plant having increased expression of the one or more genes related to desiccation tolerance, biosynthesis of cell walls, and/or transcellular water movement in response to dehydration stress when compared to a plant that lacks the heterologous Xa21 coding region. Dehydration stress includes drought, moderate drought, drought stress, or water-limiting conditions.

In some embodiments, methods for improving plant growth during moderate drought are described. Such methods can comprise expressing in one or more plants a heterologous Xa21 coding region, subjecting the one or more plants to moderate drought conditions, and selecting a plant having improved plant growth during moderate drought when compared to a plant that lacks the heterologous Xa21 coding region. Dehydration stress includes drought, moderate drought, drought stress, or water-limiting conditions.

In some embodiments, methods for increasing deposition of lignin and cellulose in the xylem vessels and their surrounding cells in a plant during dehydration stress are described. Such methods can comprise expressing in one or more plants a heterologous Xa21 coding region, subjecting the one or more plants to dehydration stress, and selecting a plant having increased deposition of lignin and cellulose in the xylem vessels and/or their surrounding cells during dehydration stress when compared to a plant that lacks the heterologous Xa21 coding region. Dehydration stress includes drought, moderate drought, drought stress, or water-limiting conditions.

In some embodiments, methods for decreasing xylem wall collapse and/or decreasing embolism (gas bubble) formation in xylem in plants during dehydration stress are described. Such methods can comprise expressing in one or more plants a heterologous Xa21 coding region, subjecting the one or more plants to dehydration stress, and selecting a plant having decreased xylem wall collapse and/or decreased embolism (gas bubble) formation in xylem during dehydration stress when compared to a plant that lacks the heterologous Xa21 coding region. Dehydration stress includes drought, moderate drought, drought stress, or water-limiting conditions.

In some embodiments, methods for improving xylem functionality in a plant during dehydration stress are described. Such methods can comprise expressing in one or more plants a heterologous Xa21 coding region, subjecting the one or more plants to dehydration stress, and selecting a plant having improved xylem functionality during dehydration stress when compared to a plant that lacks the heterologous Xa21 coding region. Dehydration stress includes drought, moderate drought, drought stress, or water-limiting conditions.

BRIEF DESCRIPTION OF THE DRAWINGS

The following drawings form part of the present specification and are included to further demonstrate the various embodiments. The disclosure may be better understood by reference to one or more of these drawings in combination with the detailed description of the embodiments presented herein.

FIG. 1A. Schematic representation of a double-tagged Xa21. An 8,739 bp genomic fragment containing the Xa21 coding region, its own intron (not indicated in FIG. 1A) and the native 5' and 3' regulatory sequences was used to express the gene. Domains of Xa21 were as described previously (Song, et al., Science 270:1804-1806, 1995): LRRs, leucine-rich repeats; TM, transmembrane domain; JM, juxtamembrane domain. A triple FLAG tag was inserted into the Dra III site, whereas a c-Myc tag was fused in frame to the C-terminus of Xa21.

Blue, A36; pink, 4021-3. The asterisk signs indicate statistically significant difference from the control A36 as calculated by Student's t test (**: p<0.01).

Figure 3A:
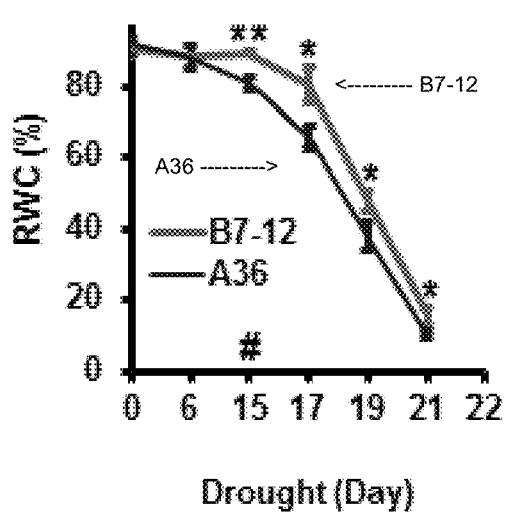

FIG. 3A. Xa21 confers tolerance to drought in rice. RWC of A36 and B7-12 plants during the course of drought treatment. # indicates the day at which A36 leaves were rolled. Results are means±s.e.m. (n=3). Data sets with asterisks indicate statistically significant difference from A36 (*: p<0.05; **: p<0.01).

Figure 3B:
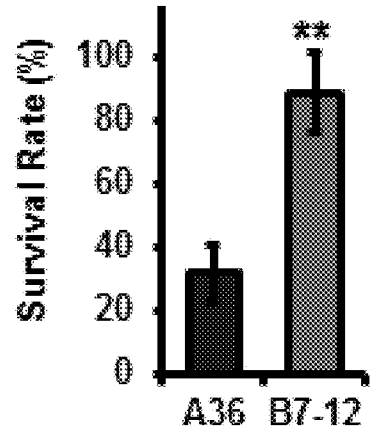

FIG. 3B. Xa21 confers tolerance to drought in rice. Survival rates of the drought-treated seedlings. Results are means±s.e.m. (n=3). Data sets with asterisks indicate statistically significant difference from A36 (**: p<0.01).

Figure 3C:
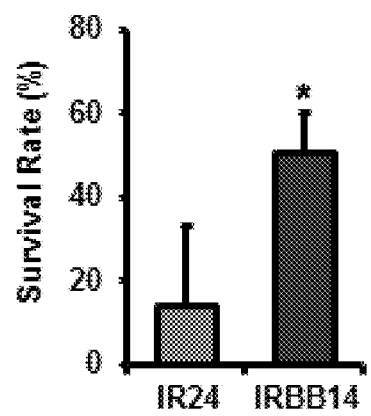

FIG. 3C. Survival rates of the drought-treated seedlings. Results are means±s.e.m. (n=3). Data sets with asterisks indicate statistically significant difference from A36 (*: p<0.05).

Figure 4A:
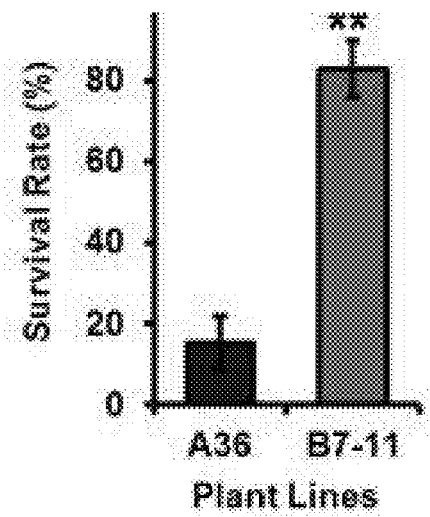

FIG. 4A. The Xa21 line B7-11 displays tolerance to drought. Survival rates of the drought-treated seedlings. Results are means±s.e.m. (n=3). The asterisk signs indicate statistically significant difference from A36 as calculated using Student's t test (**: p<0.01).

Figure 4B:
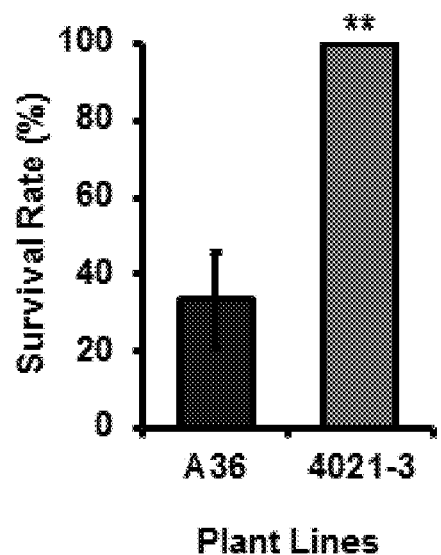

FIG. 4B. The Xa21 line 4021-3 is tolerant to drought. Survival rates of the stress-treated seedlings. Results are means±s.e.m. (n=3). The asterisk signs indicate statistically significant difference from A36 or IR24 as calculated by Student's t test (**: p<0.01).

Figure 4C:
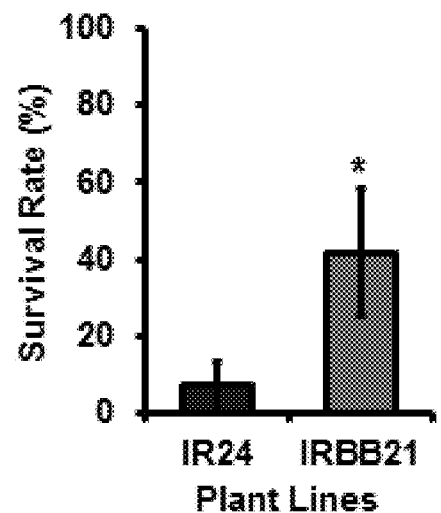

FIG. 4C. The Xa21 line IRBB21 is tolerant to drought. Survival rates of the drought-treated seedlings. Results are means±s.e.m. (n=3). The asterisk signs indicate statistically significant difference from A36 or IR24 as calculated by Student's t test (*: p<0.05). Of note, transgenic lines containing Xa21 are often more resistant to Xoo PXO99A than the introgression line IRBB21, likely due to higher levels of transgene expression (Song, et al., *Science* 270:1804-1806, 1995).

Figure 5:
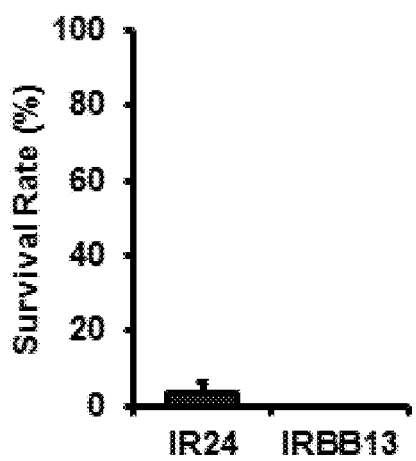

FIG. 5. IRBB13 seedlings display no tolerance to drought. Survival rates of the drought-treated seedlings (n=20). Results are means±s.e.m. (n=3).

Figures 6A, 6B, 6C, 6D:
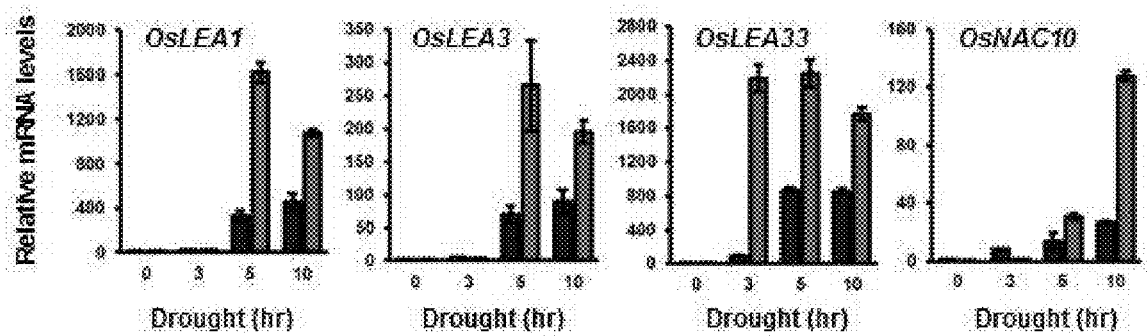

FIG. 6A. Xa21 potentiates expression of OsLEA1 drought-related gene in response to water stress in A36 and B7-12 seedlings.

FIG. 6B. Xa21 potentiates expression of OsLEA3 drought-related gene in response to water stress.

FIG. 6C. Xa21 potentiates expression of OsLEA33 drought-related gene in response to water stress.

FIG. 6D. Xa21 potentiates expression of OsNAC10 drought-related gene in response to water stress.

Figure 6E:
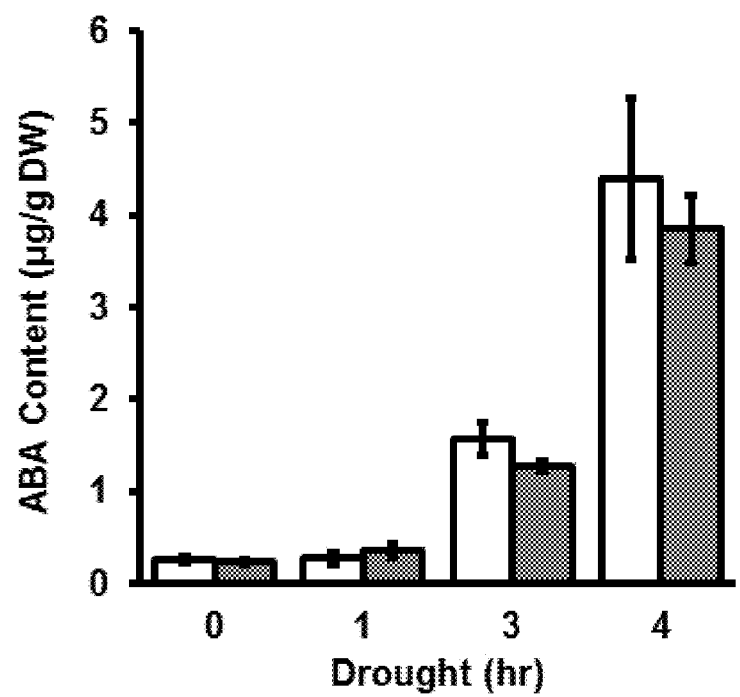

FIG. 6E. Comparisons of ABA levels in A36 and the Xa21-expressing line B7-12 after drought treatment. ABA contents of leaves were determined from two-week-old seedlings. Each data point represents mean of three independent biological replicates. White, A36; gray, B7-12.

Figure 7A:
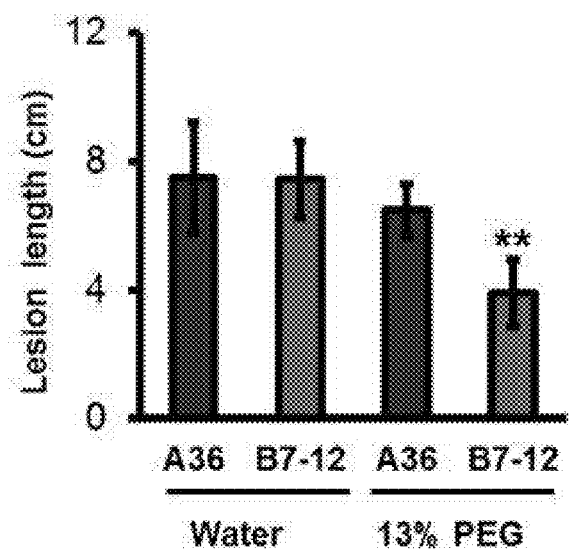

FIG. 7A. Lesion length measurements of inoculated plants (n=15 each line) at 7 dpi. Severe drought-stress induces Xa21-dependent defense against the compatible Xoo strain DY87031. Two-week-old A36 and B7-12 seedlings were inoculated with Xoo strain DY87031 and incubated with or without 13% PEG to initiate disease development. Data points represent mean±SD (n=3 each). CFU, colony-forming unit. The asterisk signs indicate statistically significant difference from the control A36 (treated with 13% PEG) as calculated using Student's t test (**: p<0.01).

Figure 7B:
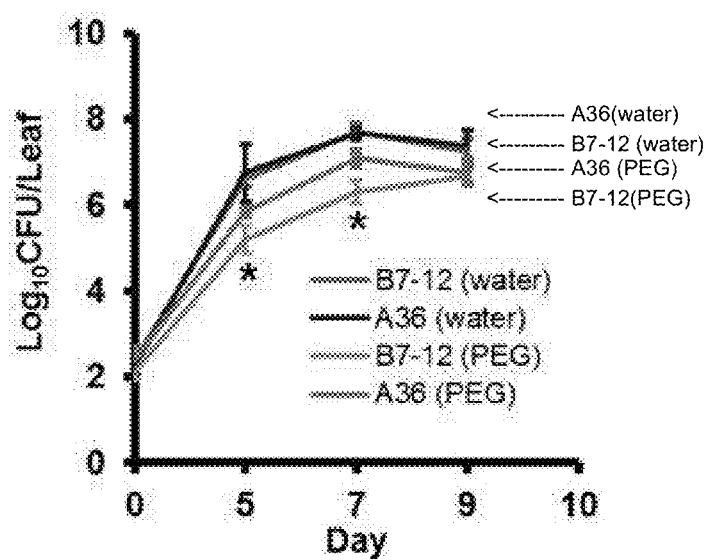

FIG. 7B. Growth of Xoo in inoculated plants. Data points represent mean±SD (n=3 each). CFU, colony-forming unit. The asterisk signs indicate statistically significant difference from the control A36 (treated with 13% PEG) as calculated using Student's t test (*: p<0.05).

Figure 8A:
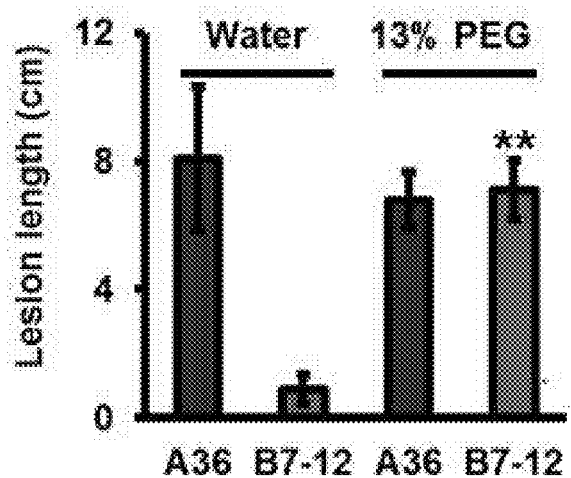

FIG. 8A. Lesion lengths of diseased leaves (n=15 each line) at 10 dpi. Two-week-old A36 and B7-12 seedlings were inoculated with Xoo PXO99A and incubated with or without 13% PEG. The asterisk signs indicate statistically significant difference from the control B7-12 as calculated using Student's t test (*: p<0.05; **: p<0.01).

Figure 8B:
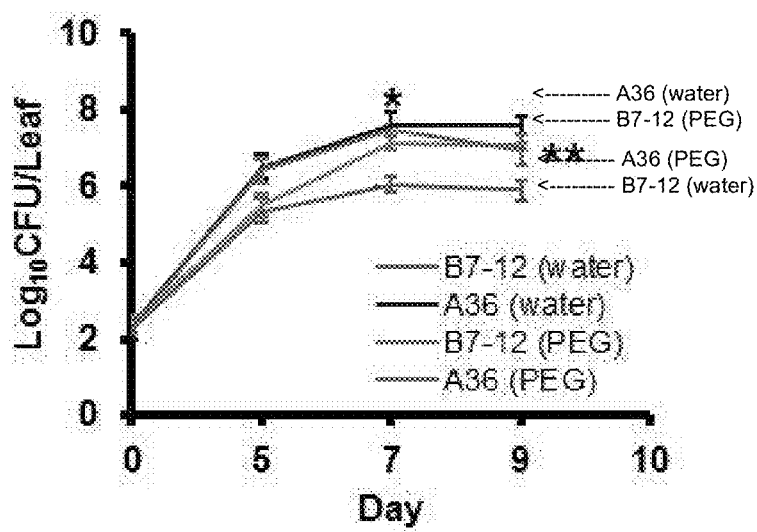

FIG. 8B. Growth of PXO99A in PEG-treated plants. Two-week-old A36 and B7-12 seedlings were inoculated with Xoo PXO99A and incubated with or without 13% PEG. The asterisk signs indicate statistically significant difference from the control B7-12 as calculated using Student's t test (*: p<0.05; **: p<0.01).

Figure 8C:
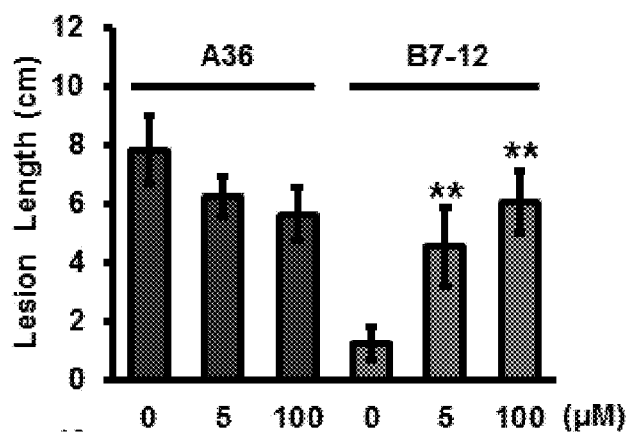

FIG. 8C. Lesion lengths of diseased leaves (n=15 each line) at 10 dpi. Two-week-old A36 and B7-12 seedlings were inoculated with Xoo PXO99A and incubated with or without ABA. The asterisk signs indicate statistically significant difference from the control B7-12 as calculated using Student's t test (*: p<0.05; **: p<0.01).

Figure 8D:
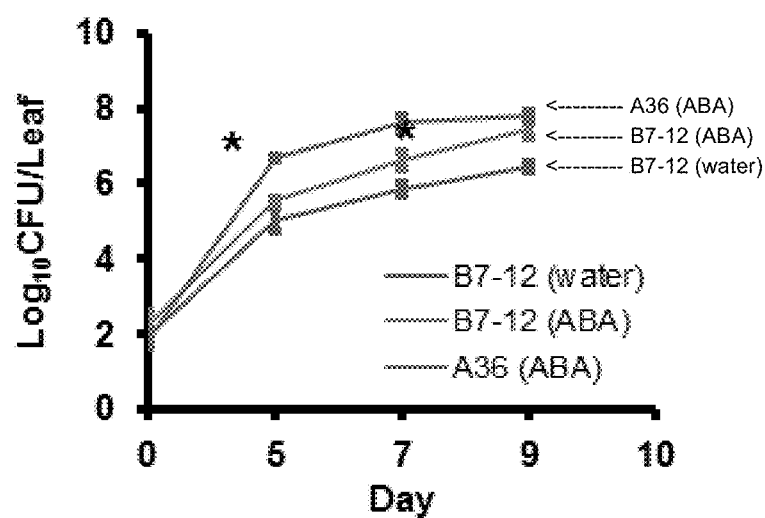

FIG. 8D. Growth of PXO99A in ABA-treated plants Two-week-old A36 and B7-12 seedlings were inoculated with Xoo PXO99A and incubated with or without ABA. The asterisk signs indicate statistically significant difference from the control B7-12 as calculated using Student's t test (*: p<0.05; **: p<0.01).

Figure 9A:
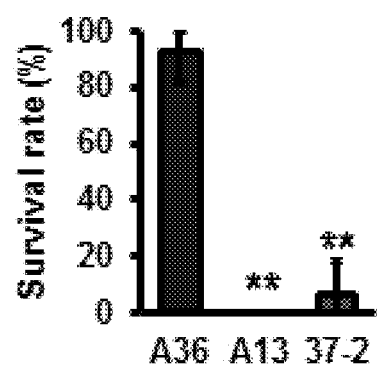

FIG. 9A. The rice Xb3 gene acts as a drought regulator. Survival rates of the drought-treated lines. Results in are means±s.e.m. (n=3). Data sets with asterisks indicate statistically significant difference from A36 (*: p<0.05; **: p<0.01).

Figure 9B:
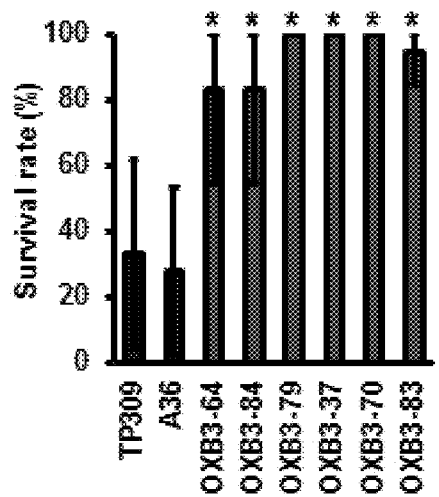

FIG. 9B. The rice Xb3 gene acts as a drought regulator. Survival rates of the indicated lines after drought stress. Results in are means±s.e.m. (n=3). Data sets with asterisks indicate statistically significant difference from A36 (*: p<0.05; **: p<0.01).

Figure 9C:
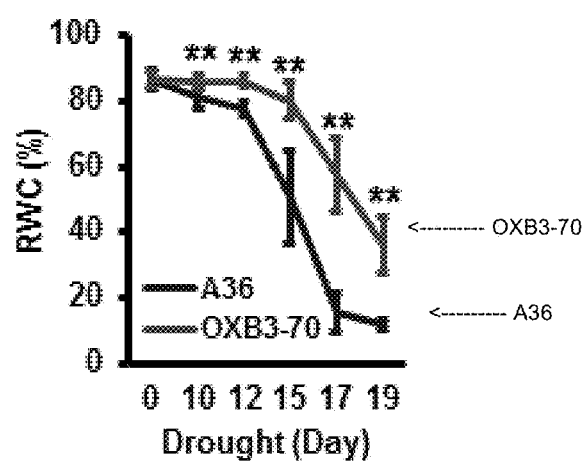

FIG. 9C. The rice Xb3 gene acts as a drought regulator. RWC of A36 and OXB3-70 plants during the course of drought treatment. Results in are means±s.e.m. (n=3). Data sets with asterisks indicate statistically significant difference from A36 (*: p<0.05; **: p<0.01).

Figure 10:

FIG. 10. XA21 regulates XB3 nuclear accumulation. Structure and domain organization of XB3. The predicted XB3 domains include an N-terminal putative myristoylation motif in which the myristoylation residue $G^2$ (Gly-2) is indicated, an ankyrin domain, a RING finger (RF) motif and the C-terminal region possessing a newly identified NLS (the basic residues underlined, the number indicates position of the Lys residue in the full-length XB3). The insertion sites for eGFP and mCherry are shown.

Figure 11:
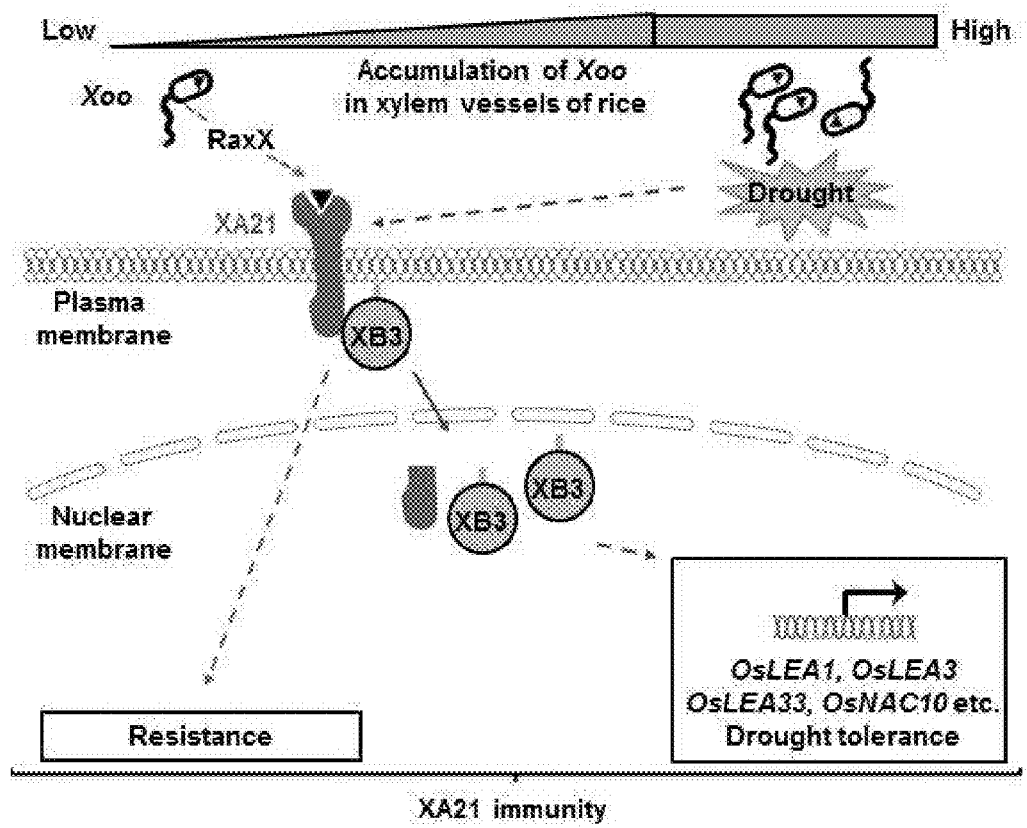

FIG. 11. Working model for Xa21-mediated immunity. At the early stage of incompatible Xoo infection, progressive bacterial growth in rice leaves triggers Xa21-mediated defense signaling (green dashed lines), which leads to the restriction of bacterial over-proliferation and disease development. With the Xoo levels reaching a plateau in the xylem vessels, drought stress becomes evident, which in turn activates Xa21-mediated drought signaling (red lines) that involves a release of XB3 from the XA21 complex into the nucleus, where the E3 ubiquitin ligase might degrade a substrate(s) for tolerance to drought.

Figure 12:
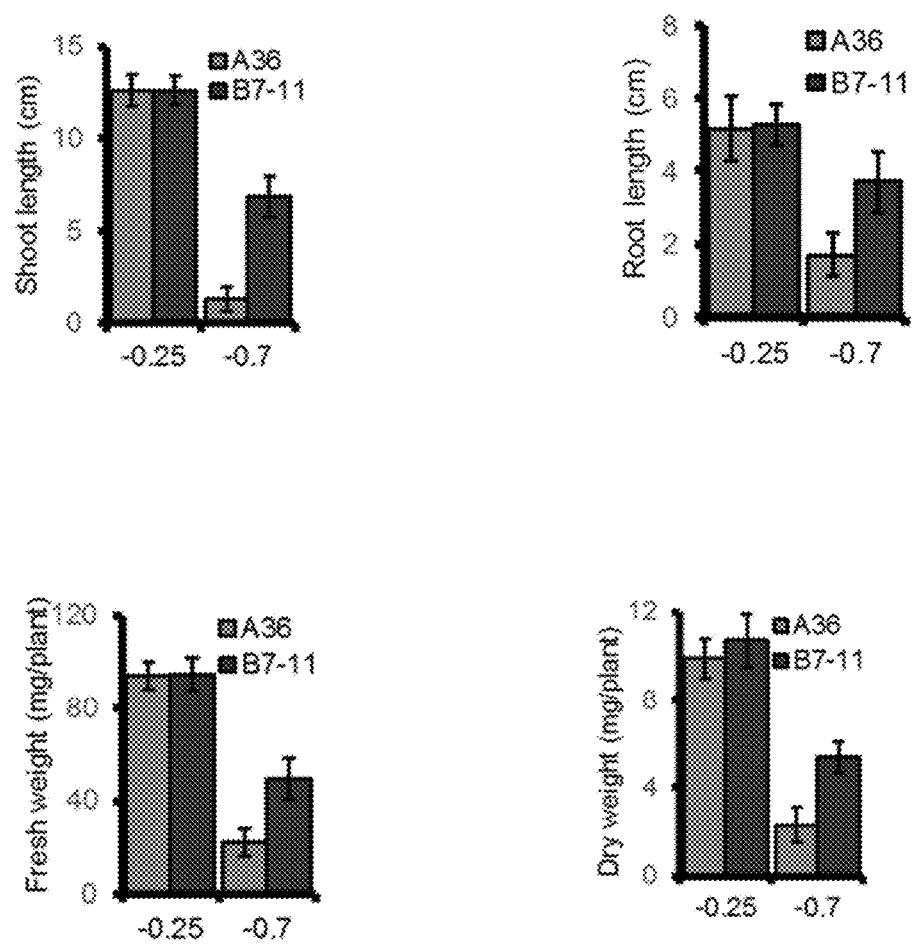

FIG. 12. Xa21 is required for enhanced growth under low-$\psi_w$ stress. Three-day-old rice seedlings of Xa21 (B7-11) and control (A36) lines (n=10 per line) were transferred from half strength MS media (−0.25 MPa) to low-$\psi_w$ agar plates (−0.7 MPa). Growth parameters were scored 5 days after transfer, Shoot and root lengths of low-$\psi_w$ treated seedlings. Fresh and dry weights of low-$\psi_w$ treated seedlings. Error bars are SD (n=3). \*\*, P<0.01. Similar results were observe for 4021-3 and IRBB21 plants.

Figure 13A:
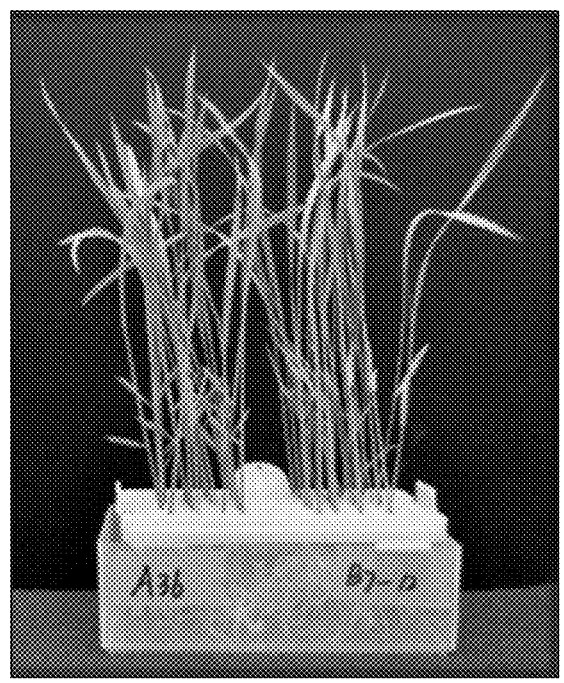
Figure 13A:
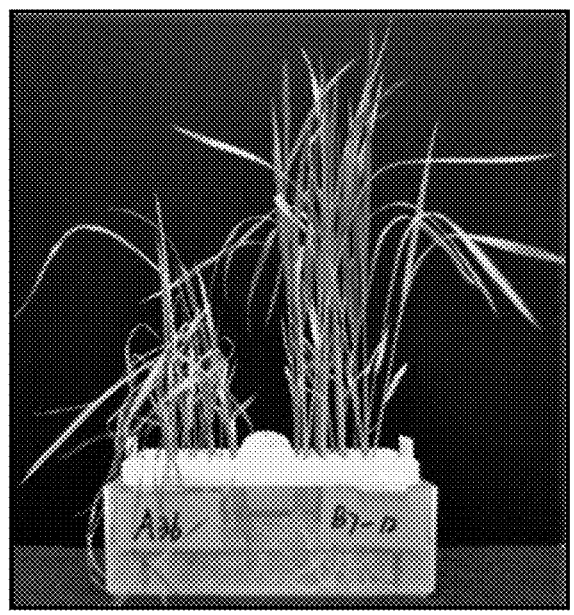

FIG. 13A. Phenotypes of representative 2-week-old A36 (empty-vector control) and B7-12 (expressing 3×FLAG-Xa21-Myc) plants (n=24 per line) prior to and after dehydration stress.

Figure 13B:
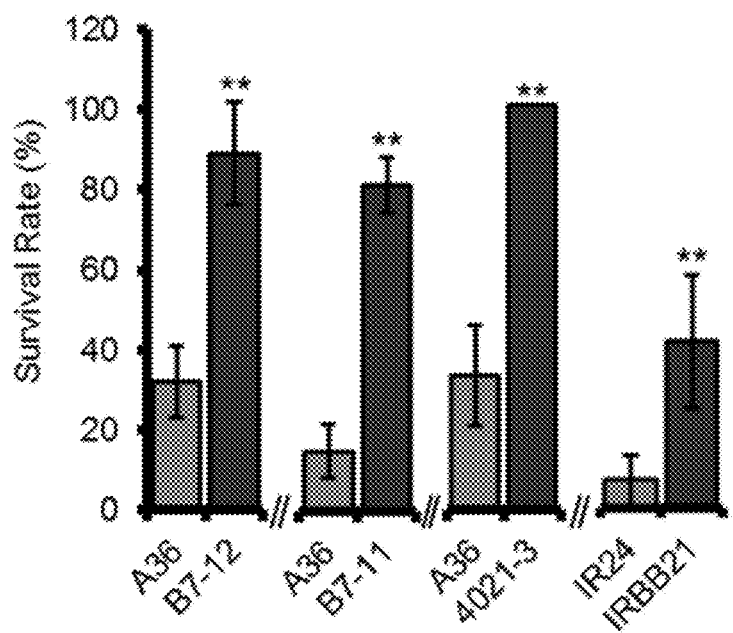

FIG. 13B. Survival rates of dehydration-treated Xa21 (B7-12, B7-11, 4021-3 and IRBB21) and control (A36, IR24) lines (n=24 per line). Scale bars (yellow) in a=2 cm. Error bars in b and c are SD (n=3). \*, P<0.05; \*\*, P<0.01.

Figure 13C:
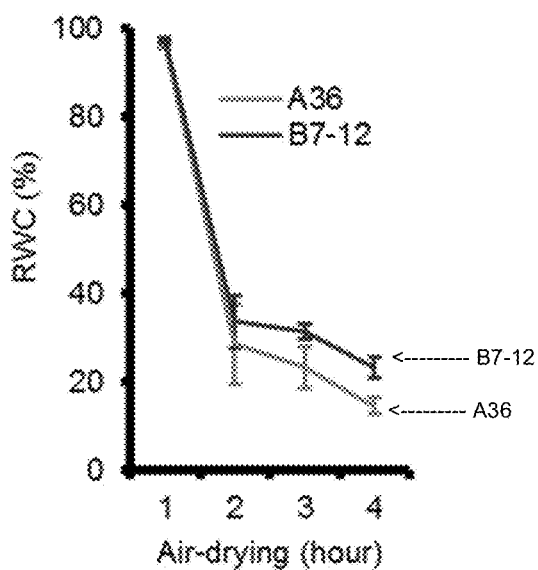

FIG. 13C. Relative Water Content (RWC) of A36 and B7-12 seedlings during 4 h of dehydration. Scale bars (yellow) in a=2 cm. Error bars in b and c are SD (n=3). \*, P<0.05; \*\*, P<0.01.

Figure 14A:
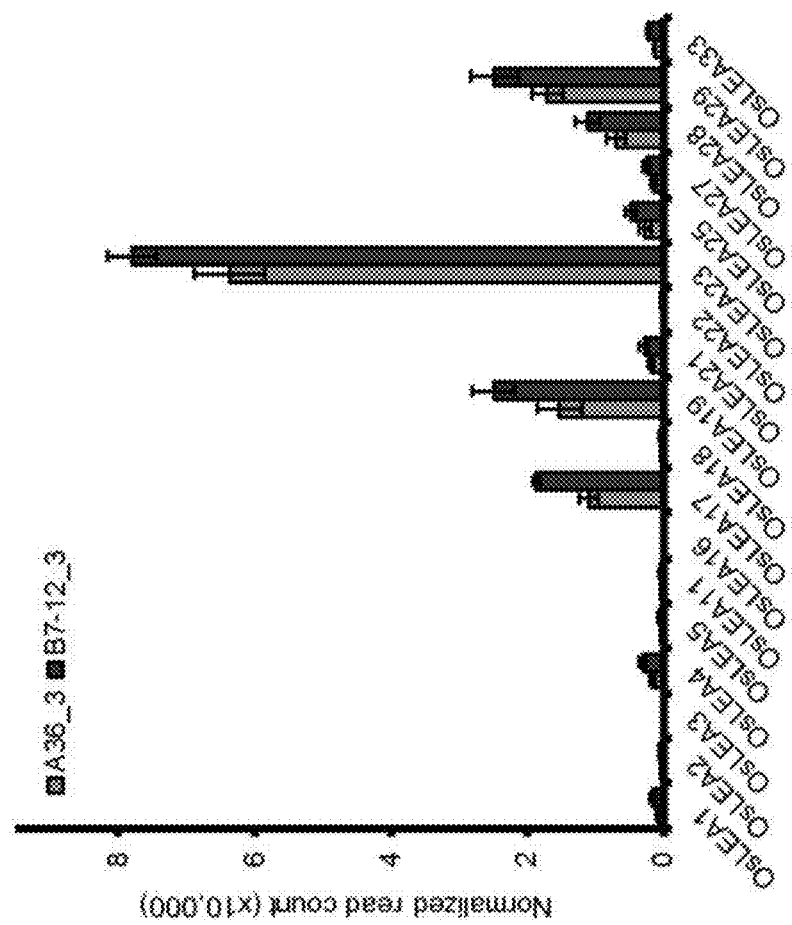

FIG. 14A. Expression of OsLEA genes in the indicated genotypes 3 h (A36_3 and B7-12_3) post air-drying (hpa) measured by RNA-seq.

Figures 14B, 14C, 14D:
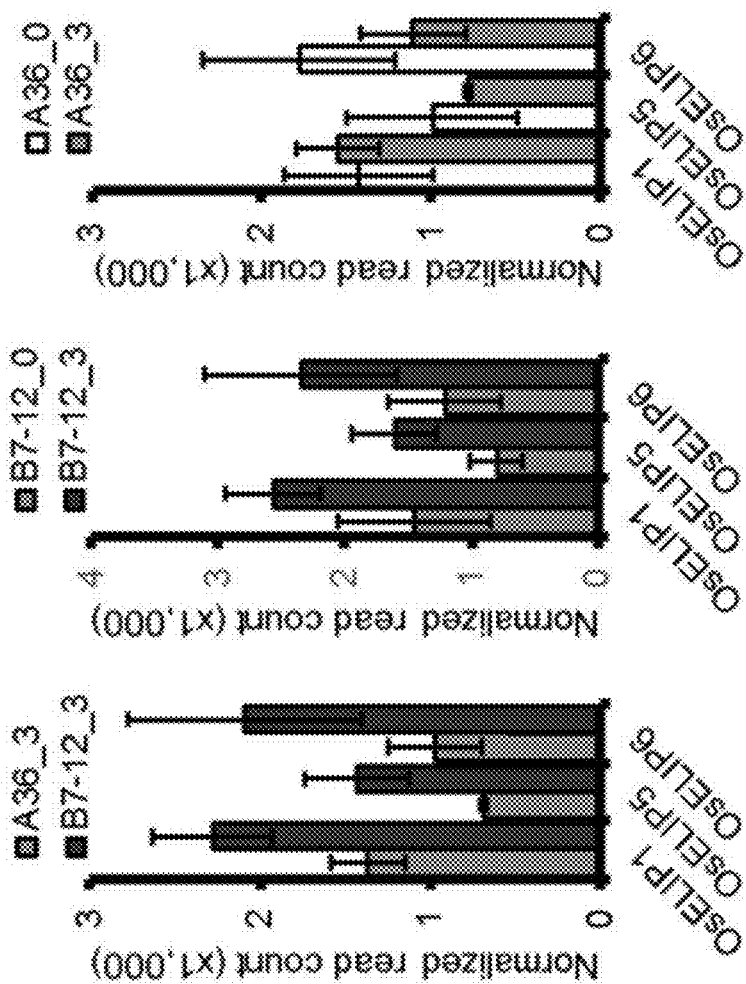

FIG. 14B. Expression of OsELIPs 3 h at 3 hpa.

FIG. 14C. Expression of OsELIPs in B7-12 at 0 (B7-12_0) and 3 hpa.

FIG. 14D. Expression of OsELIPs in A36 at 0 (A36_0) and 3 hpa. Unless otherwise indicated, all the genes described in expression studies in this and the other figures were selected based on their differential expression (adjusted P<0.05) at 3 hpa or under moderate drought stress between A36 and B7-12. Error bars are SD (n=3). \*, P<0.05; \*\*, P<0.01.

Figure 15A:
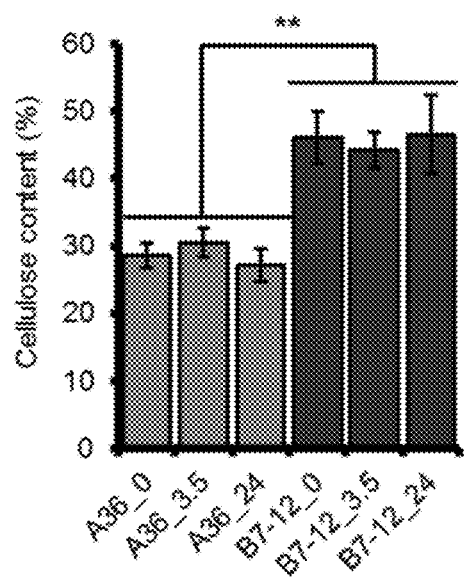

FIG. 15A. Leaf cellulose content at 0, 3.5 or 24 hpa. Error bars are SD (n=4).

Figure 15B:
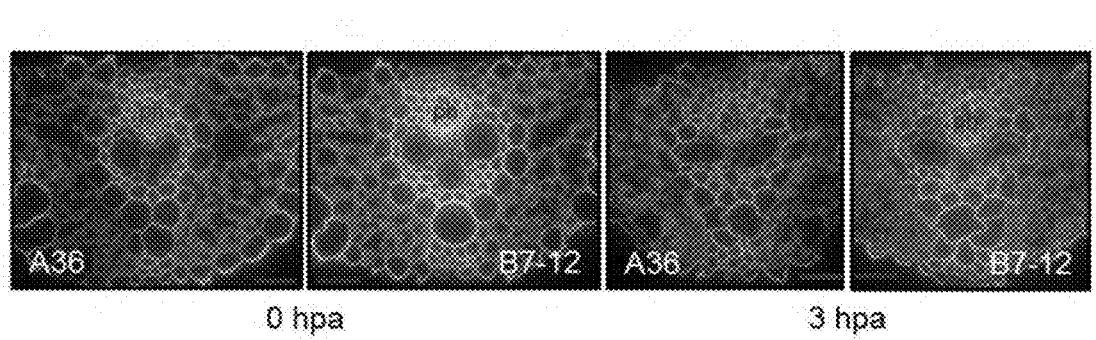

FIG. 15B. Cross sections of leaf blades of indicated lines stained with calcofluor white (binding with cellulose) at 0 or 3 hpa. Scale bars=20 μm.

Figure 15C:
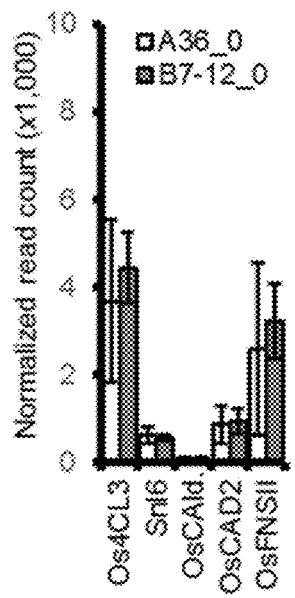

FIG. 15C. Expression of rice lignin biosynthetic genes measured by RNA-seq.

Figure 15D:
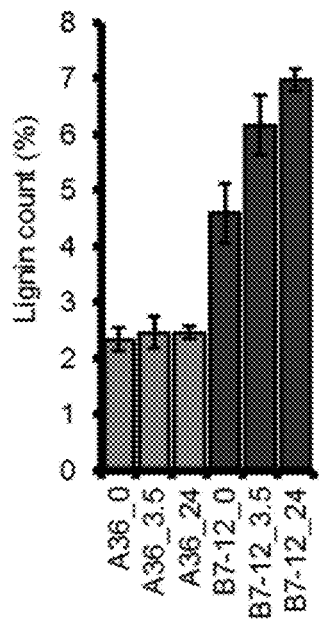

FIG. 15D. Leaf lignin content of indicated genotypes at 0, 3.5 or 24 hpa. Error bars are SD (n=4).

Figure 16:
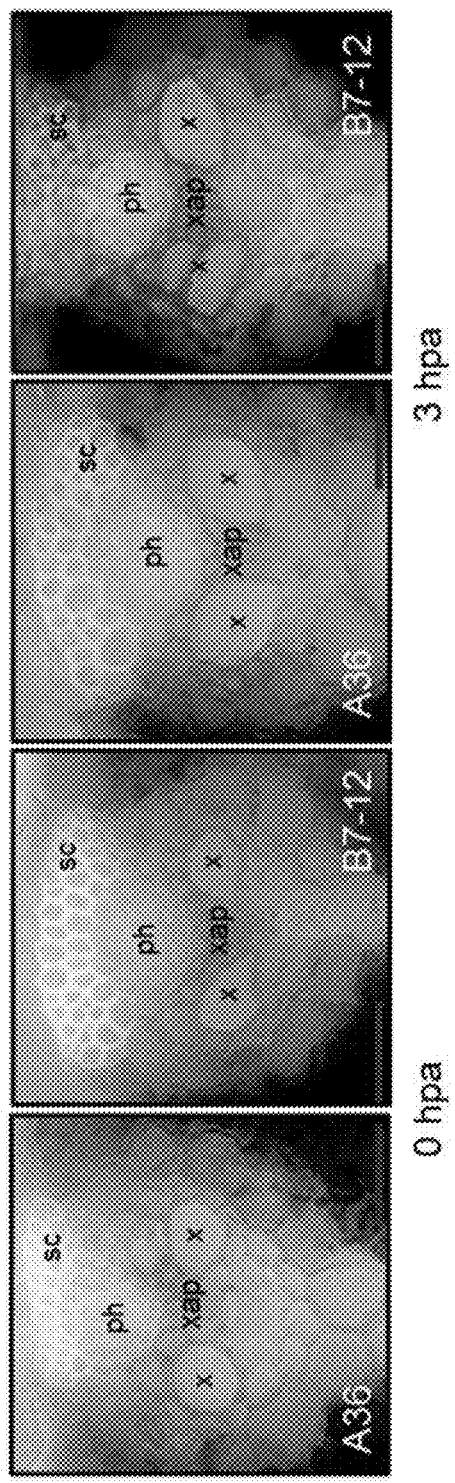

FIG. 16. Cross sections of leaf blades of indicated lines stained with phloroglucinol (staining lignin polymers in red). x, xylem; ph, phloem; sc, sclerenchyma cell; xap, xylem associated parenchyma cell. Scale bars=20 μm.

Figure 17A:
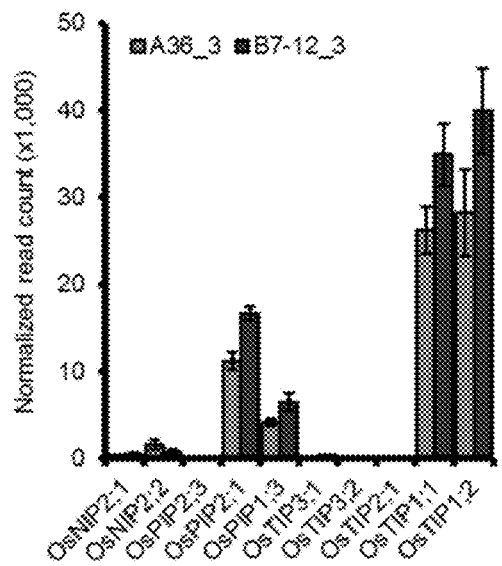

FIG. 17A. Expression of rice aquaporin genes in the indicated genotypes at 0 and 3 hpa measured by RNA-seq.

Figure 17B:
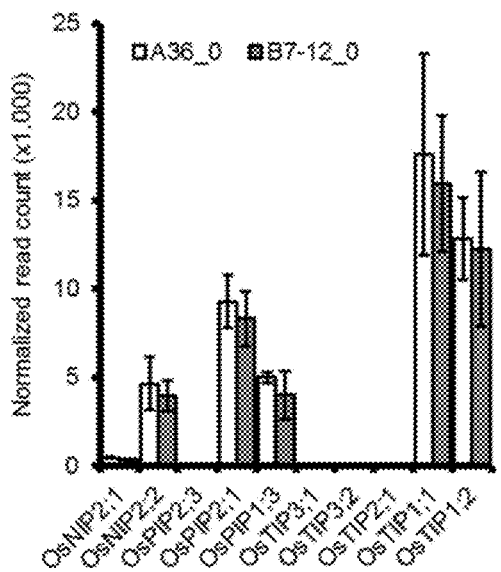

FIG. 17B. Expression of rice aquaporin genes in the indicated genotypes at 0 and 3 hpa measured by RNA-seq.

Figure 17C:
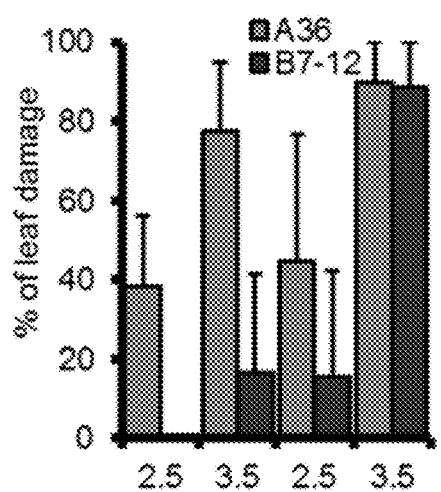

FIG. 17C. Percentage of leaf damage after dehydration recovery with or without $HgCl_2$. Error bars are SD (n=10).

Figure 18A:

FIG. 18A. Phenotypes of representative A36 and B7-12 seedlings grown on control (−0.25 MPa) or low-$\psi_w$ (−0.7 MPa; PEG-infused) medium.

Figures 18B, 18C, 18D, 18E:
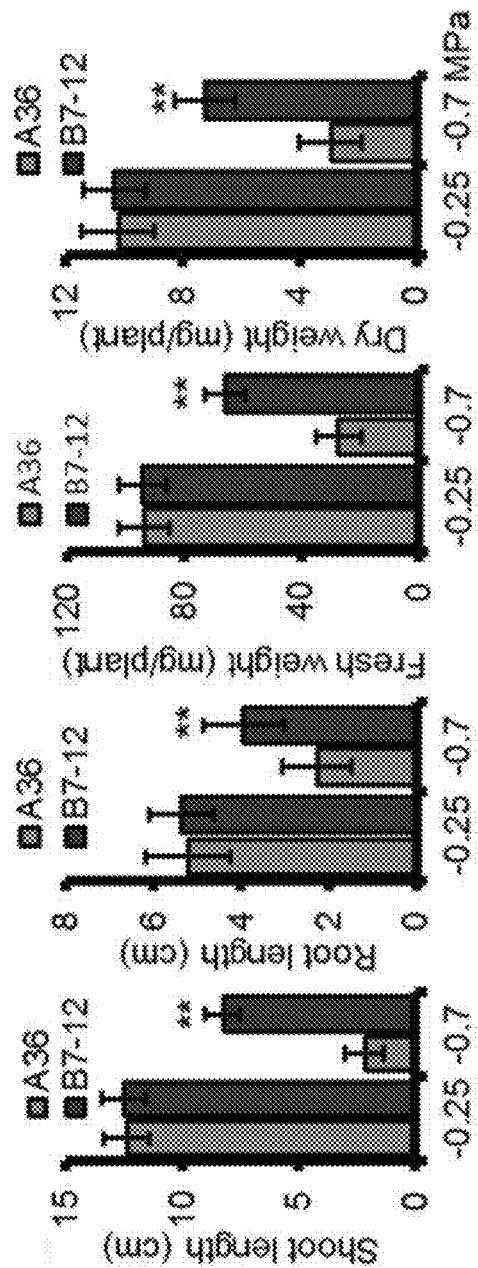

FIG. 18B. Graph showing shoot length in A36 and B7-12 seedlings grown on control (−0.25 MPa) or low-$\psi_w$ (−0.7 MPa; PEG-infused) medium.

FIG. 18C. Graph root length in A36 and B7-12 seedlings grown on control (−0.25 MPa) or low-$\psi_w$ (−0.7 MPa; PEG-infused) medium.

FIG. 18D. Graph showing fresh weight of A36 and B7-12 seedlings grown on control (−0.25 MPa) or low-$\psi_w$ (−0.7 MPa; PEG-infused) medium.

FIG. 18E. Graph showing dry weight of A36 and B7-12 seedlings grown on control (−0.25 MPa) or low-$\psi_w$ (−0.7 MPa; PEG-infused) medium.

Figure 18F:
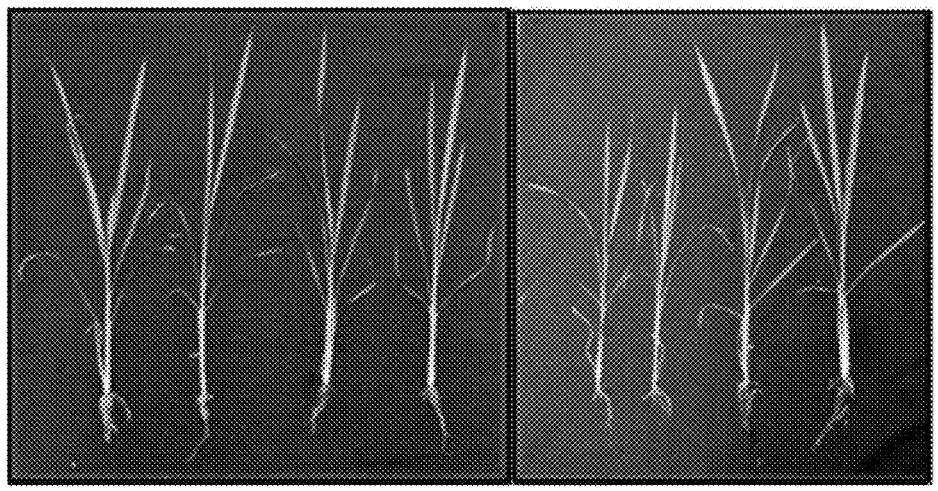

FIG. 18F. Phenotypes of A36 and B7-12 plants grown in well-watered soil or partially dry soil for one month.

Figure 18G:
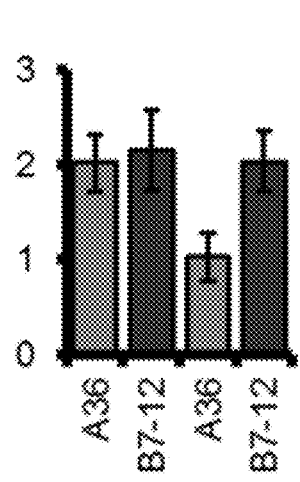

FIG. 18G. Graph showing fresh weight of A36 and B7-12 plants treated with moderate drought.

Figure 18H:
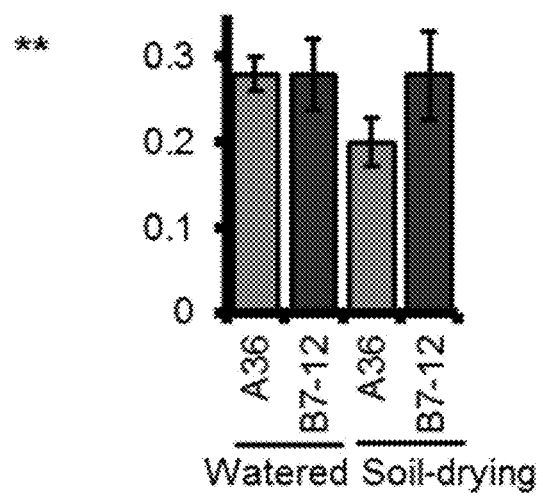

FIG. 18H. Graph showing dry weight of A36 and B7-12 plants treated with moderate drought.

Figure 19:
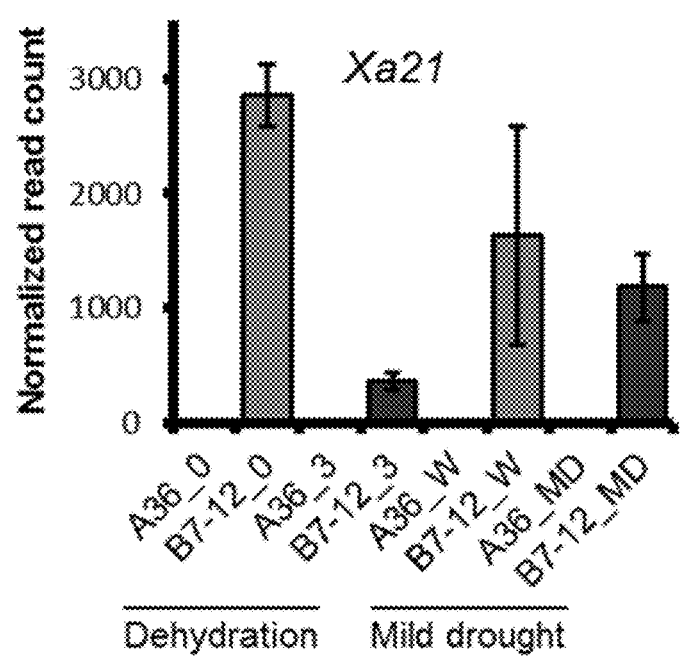

FIG. 19. Comparative transcriptomic profile analysis of drought treated Xa21 plants. Expression of Xa21 as measured by RNA-seq following dehydration and moderate drought. Error bars are SD (n=3). \*, P<0.05; \*\*, P<0.01.

DETAILED DESCRIPTION

The following detailed description is provided to guide those of ordinary skill in the art in the practice of the present invention. Unless otherwise noted, terms are to be understood according to conventional usage by those of ordinary skill in the relevant art.

It has surprisingly been shown that transgenic plants expressing a heterologous Xa21 gene displayed strong drought tolerance, as compared to control plants that lack the heterologous Xa21 gene. Disclosed are methods and compositions that permit engineering of plants for drought tolerance. In this manner, agronomic performance of crop plants may be increased, particularly when plants are subject to osmotic stress at any given stage of growth. This is particularly important in avoiding crop loss and also in increasing water use efficiency. Methods and compositions are provided for obtaining improvements in osmotic stress tolerance. In specific embodiments, expression cassettes comprising an Xa21 nucleotide sequence are described operably linked to a promoter that directs expression or overexpression of the Xa21 nucleotide sequence in the plant cell. In additional embodiments, a plurality of Xa21 transgenic plants are generated, and plants having improved drought tolerance compared to a control plant are selected.

Innate immunity plays an important role in protecting evolutionarily diverse species from pathogen infection. To perceive pathogenic invaders, hosts have evolved pattern-recognition receptors (PRRs) for detecting pathogen- or microbe-associated molecular patterns (PAMPs or MAMPs) and receptors for recognizing virulence effectors produced by pathogens for manipulating PAMP-triggered immunity and/or host cell physiology (Chisholm, et al., *Cell* 124:803-814, 2006; Jones and Dangl, *Nature* 444:323-329, 2006). Plant PRRs are cell-surface proteins belonging to receptor kinase and receptor-like protein superfamilies, whereas the majority of effector-recognizing receptors are intracellular proteins possessing nucleotide-binding (NB) and leucine-rich repeat (LRR) domains (Couto and Zipfel, *Nat. Rev. Immunol.* 16:537-552, 2016; Dangl and Jones, *Nature* 411: 826-833, 2001). Well-studied PRRs include *Arabidopsis* flagellin sensitive 2 (FLS2), elongation factor receptor (EFR) and chitin elicitor receptor kinase 1 (CREK1) that recognize bacterial flagellin, elongation factor Tu (EF-Tu) and the fungal cell wall component chitin, respectively (Gómez-Gómez and Boller, *Mol. Cell* 5:1003-1011, 2000; Zipfel, et al., *Cell* 125:749-760, 2006; Miya, et al., *Proc. Natl. Acad. Sci. USA* 104:19613-19618, 2007). Many NB-LRR proteins are encoded by classic disease resistance genes and NB-LRR-encoding sequences represent one of the largest gene families in plants (Meyers, et al., *Plant Cell* 15:809-834, 2003; Sanseverino, et al., *Nucleic Acids Res.* 38(Database issue):D814-821, 2010). Upon activation, immune receptors mobilize a defense response leading to restriction of pathogen proliferation.

Figure 2:
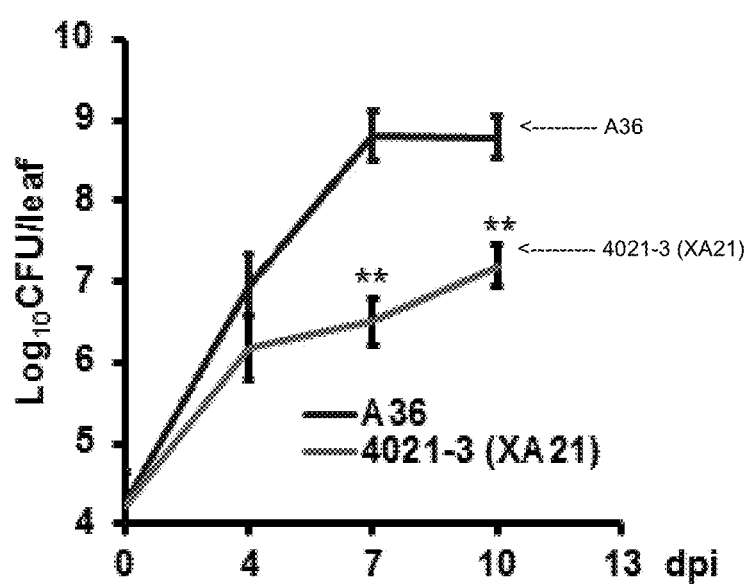
FIG. 2. Xa21-expressing plants display milder drought-related injuries than the control after Xoo infection. Growth of PXO99A in 4021-3 and A36 plants. Each data point represents mean±SD (n=3 each). CFU, colony-forming unit.

The Gram-negative bacteria *Xanthomonas oryzae* pv. *oryzae* (Xoo) is the causal agent of bacterial leaf blight disease of rice (*Oryza sativa* L.). After entering leaves, Xoo exclusively accumulates and spreads in xylem vessels, causing phenotypes (i.e., leaf rolling and wilting) similar to those seen in plants stressed by drought (Niño-Liu, et al., *Mol. Plant Pathol.* 7:303-324, 2006). The product of the rice gene Xa21 confers resistance to Xoo and is among the first cell-surface receptors identified in the innate immune system of plants and animals (Song, et al., *Science* 270:1804-1806, 1995; Chen, et al., *Mol. Plant.* 3:917-926, 2010; Park, et al., *PLoS One* 5:e9262, 2010). Like FLS2 and EFR, XA21 is a LRR-receptor kinase whose intracellular domain belongs to the non-RD subclass of the receptor-like kinase/Pelle family (Song, et al., *Science* 270:1804-1806, 1995; Dardick and Ronald, *PLoS Pathog.* 2:e2, 2006). Evidence has been shown to support XA21 as a PRR recognizing the Xoo protein 'required for activation of XA21' (RaxX) (Pruitt et al., *Sci. Adv.* 1:e1500245, 2015). Xa21-mediated resistance is only fully expressed in adult plants (Century, et al., *Plant J.* 20:231-236, 1999), however the inventors have shown that the developmentally-regulated resistance can be restored at the seedling stage by a low temperature (23-27° C.) treatment. In highly resistant plants expressing Xa21, incompatible Xoo strains (e.g., PXO99A) still grow and propagate to a significant level (~$10^7$ to $10^8$ bacterial cells/infected leaf), but they induce only shorter disease lesions and weaker water stress phenotypes than observed in susceptible individuals (FIG. 2).

Under normal growth conditions devoid of Xoo, Xa21 is constitutively expressed and likely forms stable protein complexes with XA21 binding proteins (XBs) in multiple subcellular compartments. Aside from the plasma membrane, XA21 is also localized to the endoplasmic reticulum (ER) (Park, et al., *PLoS One* 5:e9262, 2010). Co-immunoprecipitation experiments have detected five XBs in XA21 precipitates prepared from fully mature leaves. They are XB3, the ATPase XB24, the ER chaperone luminal-binding protein 3 (OsBiP3), XB25, and rice somatic embryogenesis receptor kinase 2 (OsSERK2) (Park, et al., 2010, supra; Wang, et al., *Plant Cell* 18:3635-3646, 2006; Chen, et al., *Proc. Natl. Acad. Sci. USA* 107:8029-8034, 2010; Jiang, et al., *Plant J.* 73:814-823, 2013; Chen, et al., *Mol. Plant* 7:874-892, 2014).

The first reported XA21 binding partner XB3 possesses an N-terminal myristoylation site, eight imperfect copies of ankyrin repeats, a RING finger (RF) domain, and a C-terminal region (XB3-C) (Wang, et al., 2006, supra). XB3 binds to the intracellular domain of XA21 through its ankyrin repeats, while the RF motif of XB3 is responsible for ubiquitin ligase activity. The Xb3 gene is required for full XA21 accumulation and resistance. When over-expressed in *Nicotiana benthamiana* (*N. benthamiana*), XB3 and its orthologs from diverse plant species are capable of triggering rapid cell death (Huang, et al., *PLoS One* 8: e63868, 2013). Despite these informative findings, the function and subcellular localization of XB3 are not fully understood.

It has been shown in rice that an N-terminal c-Myc epitope-tagged XA21 (Myc-XA21, ~140 kDa) is sensitive to proteolytic cleavage by an unidentified protease(s) resulting in an N-terminal cleavage product (XA21$^{ncp}$) of ~100 kDa (Xu, et al., *Plant J.* 45:740-751, 2006). XA21$^{ncp}$ can also be detected in microsomal fractions and XA21 immunoprecipitates (Park, et al., 2010, supra; Wang, et al., 2006, supra; Chen, et al., 2010, supra; Jiang, et al., 2013, supra; Xu, et al., 2006, supra; Park and Ronald, *Nat. Commun.* 3:920, 2012). The C-terminal portion of cleaved XA21 (XA21$^{ncp}$, ~37 kDa) is detectable in the nucleus (Park and Ronald, 2012, supra). Kinase inactive (Myc-XA21$^{K736E}$) and autophosphorylation (Myc-XA21$^{S686A/T688A/S689A}$) mutants both appear to be more sensitive to cleavage, suggesting that autophosphorylation protects XA21 from degradation (Xu, et al., 2006, supra). In addition to XA21, proteolysis has been observed from other PRRs/receptor-like kinases including the *Arabidopsis* CERK1 and brassinosteroid insensitive 1-associated receptor kinase 1 (BAK1); and the symbiotic receptor kinase (SYMRK) from *Lotus japonicas* (Petutschnig, et al., *New Phytol.* 204:955-967, 2014; Domínguez-Ferreras, et al., *Plant Physiol.* 168:1106-1121, 2015; Antolín-Llovera, et al., *Curr. Biol.* 24:422-427, 2014).

The inventors have shown that XA21 signaling has a significant role in counteracting drought, which is surprising and unexpected because an immune sensor has never before been assigned a similar function under physiological conditions.

To secure survival under drought conditions, plants allow the activation of some drought protective mechanisms that can cause an otherwise unfavorable growth penalty (Kasuga et al. "Improving plant drought, salt, and freezing tolerance by gene transfer of a single stress-inducible transcription factor." Nat. Biotechnol. 17(3), 287-291 (1999). Our data show that heterologous expression of Xa21 increases drought stress tolerance. Under moderate water-deficits, XA21 induces OsbHLH148 and possibly another transcription factor gene(s), which in turn transcriptionally activate the conserved OsDREB1s for drought protection and OsJAZs for maintaining plant growth. In wild-type plants, OsbHLH148 is up-regulated by severe, but not by moderate, water deficit stress. Transgenic rice and *Arabidopsis* plants over-expressing OsDREB1A or OsDREB1B alone display drought resistance with growth retardation (Dubouzet 2003 and Ito 2006). In contrast, plant over-expressing OsbHLH148 in conjunction with up-regulated OsDREB1A and OsDREB1B confer resistance to drought, but grow normally (Seo 2011). Thus, XA21-mediated activation of OsDREB1s and OsJAZs may be a mechanism for rice and other plants to withstand moderate drought stress with less on no growth penalty. Additionally, the suppression of drought-induced expression of the rice DELLA gene SLR1 may also contribute to XA21-mediated growth under moderate drought. In some embodiments heterologous Xa21 expression does not decrease plant growth under normal conditions and/or non-drought conditions. As used herein moderate drought conditions are conditions in which the soil matric potential (SMP) is between −700 to −900 kPa.

In some embodiments, heterologous Xa21 expression increases the expression of one or more genes related to desiccation tolerance, biosynthesis of cell walls, and/or transcellular water movement. Heterologous expression of Xa21 differentially regulates transcriptional networks based on the severity of the water stress and improves plant performance under both moderate drought and severe dehydration conditions. The control of such a broad range of plastic and adaptive drought responses by a single plant mediator has not been previously reported.

Studies from *Arabidopsis* have suggested that mechanisms regulating dehydration survival under drought stress differ from those controlling growth during mild to moderate water deficits. Many plants rapidly reduce their growth rates under mild to moderate drought. In some embodiments, heterologous Xa21 expression increases plant growth during moderate drought when compared to plants not expressing heterologous Xa21. In some embodiments, the plant is a rice plant. Increasing growth under moderate drought conditions is agronomically favorable because photosynthesis and carbon accumulation largely remain active at this stage. Without being bound by theory, heterologous expression may increase growth during moderate drought conditions by initiating growth-promoting and stress-responsive signaling through transcriptional activation of genes encoding the transcription regulators such as, but not limited to, OsbHLH148, OsDREBs, OsJAZs, and SLR1.

In some embodiments, heterologous Xa21 expression increases deposition of lignin and cellulose in the xylem vessels and their surrounding cells. Heterologous expression of Xa21 may protect water transport capacity under stress by increasing secondary cell wall thickness, providing rigidity and mechanical support to the xylem. Increased lignin may also increase plant resistance to embolism.

In some embodiments, heterologous Xa21 expression in a plant results in one or more of the following during drought, drought stress, or water limiting conditions when compared a control plant that does not express a heterologous Xa21 coding region: decreased xylem wall collapse, decreased embolism (gas bubble) formation in xylem, increased living cell protections and/or xylem functionality, increased plant survival, and plant survival.

Nucleic Acids, Polypeptides and Plant Transformation Constructs

In some embodiments, a recombinant nucleic acid sequence comprising an Xa21 gene sequence is used in generating plants expressing a heterologous Xa21 coding region. In some embodiments, a recombinant nucleic acid sequence comprising a rice Xa21 gene sequence is used in generating plants expressing a heterologous Xa21 coding region. In some embodiments, the rice Xa21 gene sequence comprises SEQ ID NO: 1. In some embodiments, a recombinant nucleic acid sequence comprising an ortholog of the rice Xa21 gene sequence is used in generating plants expressing a heterologous Xa21 coding region. In some embodiments, a recombinant nucleic acid sequence comprising a homolog of the rice Xa21 gene sequence is used in generating plants expressing a heterologous Xa21 coding region. Complements to any nucleic acid sequences described herein can also be used. Orthologs and homologs of the rice Xa21 coding region or Xa21 gene sequence can be, but are not limited to, the orthologs and/or homologs described in Song, et al., *Plant Cell* 9:1279-1287, 1997.

In some embodiments, nucleic acids and polypeptides are used that have at least about 80% (percent) sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to any of the nucleic acid or protein sequences described herein. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Methods to determine "percent sequence identity" are codified in numerous publicly available programs including, but are not limited to, GCG (also known as The Wisconsin Package™), and the BLAST programs that are publicly available from NCBI. Optimal alignment of sequences for aligning a comparison window are well known to those skilled in the art and may be conducted by tools including, but not limited to, the local homology algorithm of Smith and Waterman (*Adv. Appl. Math.* 2:482-489, 1981), the homology alignment algorithm of Needleman and Wunsch (*J. Mol. Biol.* 48:443-453, 1970), and the search for similarity method of Lipman and Pearson (*Science* 227:1435-1441, 1985).

The nucleic acids for use in any of the embodiments may be from any source, e.g., identified as naturally occurring in a plant, or synthesized, e.g., by mutagenesis. In certain embodiments, the naturally occurring sequence may be from any plant. In some embodiments, the plant may be a dicotyledonous plant, for example, Arabidopsis, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp. In some embodiments, the plant may be a monocotyledonous plant, for example maize, wheat, rice, sorghum (*Sorghum bicolor*), oats, barley, sugar cane, African oil palm (*Elaeis guineensis*), or switchgrass.

Coding sequences used in any of the embodiments may be provided in a recombinant vector operably linked to a homologous or heterologous promoter functional in plants. Expression constructs may also be used comprising these sequences. In other embodiments, plants and plant cells transformed with the sequences may be provided. The construction of vectors which may be employed in conjunction with plant transformation techniques using these or other sequences are known to those of skill of the art in light of the present disclosure (see, for example, Sambrook, et al., *Molecular Cloning: a Laboratory Manual*, Volume 3, Cold Spring Harbor Laboratory Press, Cold Spring Harbor, N.Y., 1989). The techniques described herein are thus not limited to the use of any particular nucleic acid sequences.

The choice of any additional elements used in conjunction with the Xa21 coding sequences may depend on the purpose of the transformation. One of the major purposes of transformation of crop plants is to add commercially desirable, agronomically important traits to the plant, as described herein.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences obtained therefrom and otherwise, are included. It is contemplated that utilization of cloning systems with large insert capacities will allow introduction of large DNA sequences comprising more than one selected gene. In some embodiments, a vector can be used to introduce genes corresponding to, e.g., an entire biosynthetic pathway, into a plant.

In some embodiments, expression cassettes which have been derived from such vectors are described above are used. DNA segments used for transforming plant cells will generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Components which can be included with vectors can be, but are not limited to, the components described as follows.

A. Regulatory Elements

In certain embodiments, exemplary promoters for expression of a nucleic acid sequence include plant promoters such as the CaMV 35S (Odell, et al., *Nature* 313:810-812, 1985), CaMV 19S (Lawton, et al., *Plant Mol. Biol.* 9:315-324, 1987), nos (Ebert, et al., *Proc. Natl. Acad. Sci. USA* 84:5745-5749, 1987), actin (Wang, et al., *Mol. Cell. Biol.* 12:3399-3406, 1992), UDP glucose flavonoid glycosyl-transferase gene promoter (Ralston, et al., *Genet.* 119:185-197, 1988), MPI proteinase inhibitor (Cordero, et al., *Plant J.* 6141-150, 1994), and the glyceraldehyde-3-phosphate dehydrogenase (Kohler, et al., *Plant Mol. Biol.* 29:1293-1298, 1995; Quigley, et al., *J. Mol. Evol.* 29:412-421, 1989; Martinez, et al., *J. Mol. Biol.* 208:551-565, 1989) promoter, and the ubiquitin promoters from maize or rice, or ubiquitin promoters for use in various monocotyledonous plants (Christensen and Quail, *Transgenic Res.* 5:213-218, 1996).

Tissue-specific promoters, such as Adh (Walker, et al., *Proc. Natl. Acad. Sci. USA* 84:6624-6628, 1987), sucrose synthase (Yang and Russell, *Proc. Natl. Acad. Sci. USA* 87:4144-4148, 1990), α-tubulin (Kim and An, *Transgenic Research* 1:188-194, 1992), cab (Sullivan, et al., *Mol. Gen. Genet.* 215:431-440, 1989), PEPCase (Hudspeth and Grula, *Plant Mol. Biol.* 12:579-589, 1989), lectin (Vodkin, et al., *Cell* 34:1023, 1983; Lindstrom, et al., *Dev. Genet.* 11:160, 1990), corn alcohol dehydrogenase 1 (Vogel, et al., *J. Cell. Biochem.* 13:Part D, 1989; Dennis, et al., *Nucl. Acids Res.* 12:3983-4000, 1984); corn light harvesting complex (Simpson, *Science* 233:34, 1986; Bansal, et al., *Proc. Natl. Acad. Sci. USA* 89:3654-3658, 1992), corn heat shock protein (Rochester, et al., *EMBO J.* 5:451-458, 1986), pea small subunit RuBP carboxylase (Poulsen, et al., *Mol. Gen. Genet.* 205:193-200, 1986; Cashmore, et al., *Gen. Eng. of Plants*, Plenum Press, New York, 29-38, 1983), Ti plasmid mannopine synthase or nopaline synthase (Langridge, et al., *Proc. Natl. Acad. Sci. USA* 86:3219-3223, 1989), *petunia* chalcone isomerase (Van Tunen, et al., *EMBO J.* 7:1257, 1988), bean glycine rich protein 1 (Keller, et al., *EMBO J.* 8:1309-1314, 1989), potato patatin promoters (Wenzler, et al., *Plant Mol. Biol.* 12:41-50, 1989), root cell promoters (Conkling, et al., *Plant Physiol.* 93:1203-1211, 1990), maize zein (Reina, et al., *Nucl. Acids Res.* 18:6426, 1990; Kriz, et al., *Mol. Gen. Genet.* 207:90-98, 1987; Wandelt and Feix, *Nucl. Acids Res.* 17:2354, 1989; Langridge and Feix, *Cell* 34:1015-1022, 1983; Reina, et al., *Nucl. Acids Res.* 18:6426, 1990), globulin-1 (Belanger and Kriz, *Genet.* 129:863-872, 1991), R gene complex-associated promoters (Chandler, et al., *The Plant Cell* 1:1175-1183, 1989), and chalcone synthase (Franken, et al., *EMBO J.* 10:2605-2612, 1991), or tissue selective promoters and tissue-specific enhancers (Fromm, et al., *Nature* 312:791-793, 1986, Fromm, et al., *The Plant Cell* 1:977-984, 1989) are also contemplated to be useful in certain embodiments, as are inducible promoters such as ABA- and turgor-inducible promoters, as well as drought-inducible promoters. Any suitable promoters known in the art may be used to express Xa21 coding sequences in a plant. In some embodiments, a drought-inducible or osmotic stress-inducible promoter may be used to express Xa21 coding sequences in a plant.

The DNA sequence between the transcription initiation site and the start of the coding sequence, i.e., the untranslated leader sequence, can also influence gene expression. In some embodiments, a particular leader sequence is used with a transformation construct. In some embodiments, a leader sequence can be, but is not limited to, a leader sequence which comprises sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of Xa21 coding sequences.

B. Terminators

Transformation constructs prepared in accordance with any of the described embodiments, may include a 3' end DNA sequence that acts as a signal to terminate transcription and allow for the polyadenylation of the mRNA produced by coding sequences operably linked to a promoter. In some embodiments, the native terminator of a Xa21 coding sequence is used. In some embodiments, a heterologous 3' end enhances expression of an Xa21 coding sequence. Non-limiting examples of terminators that may be used in this context include those from the nopaline synthase gene of *Agrobacterium tumefaciens* (nos 3' end) (Bevan, et al., *Nucl. Acids Res.* 11:369-385, 1983), the terminator for the T7 transcript from the octopine synthase gene of *Agrobacterium tumefaciens*, and the 3' end of the protease inhibitor I or II gene from potato or tomato. Regulatory elements such as an Adh intron (Canis, et al., *Genes Dev.* 1:1183-1200, 1987), sucrose synthase intron (Vasil, et al., *Plant Physiol.* 91:1575-1579, 1989) or TMV omega element (Gallie, et al., *The Plant Cell* 1:301-311, 1989), may further be included in some embodiments where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed.

Many selectable marker coding regions are known and could be used including, but not limited to, neo (Potrykus, et al., *Mol. Gen. Genet.* 199:183-188, 1985), which provides kanamycin resistance and can be selected for using kanamycin, G418, paromomycin, etc.; bar, which confers bialaphos or phosphinothricin resistance (Rathore, et al., *Plant Mol. Biol.* 21:871-884, 1993); a mutant EPSP synthase protein (Hinchee, et al., *Bio/Technol.* 6:915-922, 1988) conferring glyphosate resistance; a nitrilase such as bxn from *Klebsiella ozaenae* which confers resistance to bromoxynil (Stalker, et al., *Science* 242:419-423, 1988); a mutant acetolactate synthase (ALS) which confers resistance to imidazolinone, sulfonylurea or other ALS inhibiting chemicals (European Patent Application 154204, 1985); a methotrexate resistant DHFR (Thillet, et al., *J. Biol. Chem.* 263:12500-12508, 1988), a dalapon dehalogenase that confers resistance to the herbicide dalapon (Buchanan-Wollaston, et al., *Plant Cell Reports* 11:627-631, 1992); or a mutated anthranilate synthase that confers resistance to 5-methyl tryptophan (Li and Last, *Plant Physiol.* 110:51-59, 1996).

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromo* genes. The enzyme phosphinothricin acetyl transferase (PAT) inactivates the active ingredient in the herbicide bialaphos, phosphinothricin (PPT). PPT inhibits glutamine synthetase (Murakami, et al., *Mol. Gen. Genet.* 205:42-50, 1986; Twell, et al., *Plant Physiol.* 91:1270-1274, 1989), causing rapid accumulation of ammonia and cell death.

Genetic Transformation

Additionally provided herein are transgenic plants transformed with the above-identified recombinant vectors encoding Xa21, or a sequence modulating up-regulation thereof, and exhibiting tolerance to drought.

Suitable methods for transformation of plant or other cells include virtually any method by which DNA can be introduced into a cell, such as by direct delivery of DNA such as by PEG-mediated transformation of protoplasts (Omirulleh, et al., *Plant Mol. Biol.* 21:415-428, 1993), by desiccation/inhibition-mediated DNA uptake (Potrykus, et al., *Mol. Gen. Genet.* 199:183-188, 1985), by electroporation (U.S. Pat. No. 5,384,253, specifically incorporated herein by reference in its entirety), by agitation with silicon carbide fibers (Kaeppler, et al., *Plant Cell Reports* 9:415-418, 1990; U.S. Pat. Nos. 5,302,523 and 5,464,765, both specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety). Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Horsch, et al. (*Science* 227:1229-1231, 1985), Rogers and Klee (*Plant DNA Infectious Agents*, Chapter 7, Springer-Verlag/Wein, 1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas, et al., *Plant Sci.* 69:189-198, 1990), it has only more recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei, et al., *Plant Mol. Biol.* 35:205-218, 1997; U.S. Pat. No. 5,591,616, specifically incorporated herein by reference in its entirety), wheat (McCormac, et al., *Euphytica* 99:17-25, 1998), barley (Tingay, et al., *The Plant Journal* 11:1369-1376, 1997) and maize (Ishidia, et al., *Nature Biotechnology* 14:745-750, 1996).

One also may employ protoplasts for electroporation transformation of plants (Bates, *Mol. Biotechnol.* 2:135-145, 1994; Lazzeri, *Methods Mol. Biol.* 49:95-106, 1995). Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force.

A transgenic plant expressing a heterologous Xa21 coding region and exhibiting drought tolerance can be of any species. The plant can be an R0 transgenic plant (i.e., a plant derived from the original transformed tissue). The plant can be a progeny plant of any generation of an R0 transgenic plant, wherein the transgenic plant comprises the heterologous Xa21 coding region from the R0 transgenic plant.

Seeds of the above-described transgenic plants are provided, particularly where the seed comprises the heterologous Xa21 coding region. Additionally contemplated are host cells transformed with an above-identified recombinant vector. In some embodiments, the host cell is a plant cell.

The described plants having increased or enhanced expression of Xa21 and drought tolerance may be of any species. The species may be any monocotyledonous or dicotyledonous plant, such as those described herein. One of skill in the art will recognize described methods may be applied to plants of other species by employing methods described herein and others known in the art.

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Production and Characterization of Stably Transformed Plants

After effecting delivery of exogenous DNA to recipient cells, the next steps generally concern identifying the transformed cells for further culturing and plant regeneration. In order to improve the ability to identify transformants, one or more selectable or screenable marker gene may be employed with a transformation vector. In this case, one would then generally assay the potentially transformed cell population by exposing the cells to a selective agent or agents, or one would screen the cells for the desired marker gene trait. Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent Application Publication Number WO 97/4103.

The transformed cells, identified by selection or screening and cultured in an appropriate medium that supports regeneration, will then be allowed to mature into plants. Developing plantlets can be transferred to soilless plant growth mix, and hardened, e.g., in an environmentally controlled chamber, for example, at about 85% relative humidity, 600 ppm $CO_2$, and 25-250 microeinsteins $m^{-2} s^{-1}$ of light. Plants may be matured in a growth chamber or greenhouse. Plants can be regenerated after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C., for example. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant. The expression of a gene product is often determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes that change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays. Such assays for determining drought tolerance are well-described herein Breeding Plants In addition to direct transformation of a particular plant genotype with a construct prepared, transgenic plants may be made by crossing a plant having a described DNA to a second plant lacking the construct. For example, a selected Xa21 coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps: (a) plant seeds of the first (starting line) and second (donor plant line that comprises a transgene of the invention) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower. Backcrossing is herein defined as the process including the steps of: (a) crossing a plant of a first genotype containing a desired gene, DNA sequence or element to a plant of a second genotype lacking the desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype. In any one or more generations of crossing, selection may be made for drought tolerance, yielding drought tolerant progeny.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Definitions

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Overexpression: The increase in the expression of a DNA or RNA transcript and/or the function or activity of a protein relative to a control or naturally-occurring counterpart.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. In some embodiments, transformation constructs will comprise all of the genetic elements necessary to direct the expression of one or more exogenous genes. In some embodiments, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Up-regulation: The increase in the expression of a DNA or RNA transcript and/or the function or activity of a protein relative to a control or naturally-occurring counterpart.

Vector: A DNA molecule designed for transformation into a host cell. Some vectors may be capable of replication in a host cell. A plasmid is an exemplary vector, as are expression cassettes obtained therefrom.

Homolog: A gene related to a second gene by descent from a common ancestral DNA sequence. The term, homolog, may apply to the relationship between genes separated by the event of speciation or to the relationship between genes separated by the event of genetic duplication. As used herein a homolog retains the same or similar function as the reference gene or protein.

Ortholog: An ortholog is any of two or more homologous gene sequences found in different species related by linear descent. Orthologs are genes in different species that evolved from a common ancestral gene by speciation. As used herein orthologs retain the same or similar function in the different species.

As used herein drought conditions are conditions in which the soil matric potential is less that −900 kPa.

As used herein "moderate drought" conditions are conditions in which the soil matric potential (SMP) is between −700 to −900 kPa.

EXAMPLES

The following examples are included to demonstrate illustrative of the described embodiments. It should be appreciated by those of skill in the art that the techniques disclosed in the examples which follow represent techniques discovered by the inventors to function well in the practice disclosed embodiments. However, those of skill in the art should, in light of the present disclosure, will appreciate that many changes can be made in the disclosed embodiments and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1—Plasmid Construction and Plant Transformation

Figure 1A:
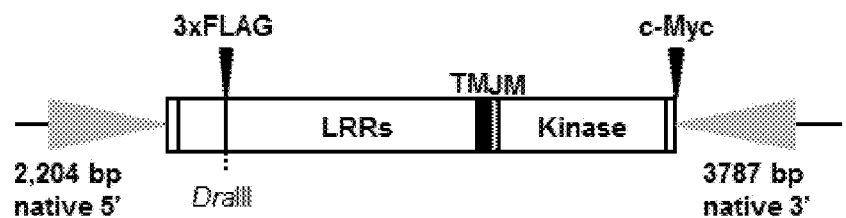
FIG. 1A. Double-tagged Xa21 confers resistance to Xoo PXO99A.

The 3×FLAG-Xa21-Myc construct was made using an 8.7 kb genomic fragment containing the c-Myc-tagged Xa21 coding region, intron and the native 5' and 3' regulatory sequences (FIG. 1A). To delete the extra 3' from the 9.9 kb Xa21-containing fragment previously used for rice transformation (Wang, et al., Plant Cell 18:3635-3646, 2006), a KpnI-SpeI fragment with Myc-Xa21 was mobilized from the plasmid pBEK822-Bm into the vector pKBluescript to generate pKBXA21KS-M. An additional 1.8 kb 3' sequence, PCR amplified from the 9.9 kb Xa21 fragment with primers Xa21-Tail-F (CTTTCCGAAGACGAGTATATCTAACG; SEQ ID NO: 3)/Xa21-Tail-R (ACTAGTGGTACCCGTCT-TATATCGCCTCA; SEQ ID NO: 4), was added to the 3' end of the KpnI-SpeI fragment of pBXA21KS-M using the SpeI site. The resultant construct, namely pKB-Myc-XA21-S, contains a c-Myc tag (EQKLISEEDLLEK; SEQ ID NO: 15) in the N-terminal region (domain B) of XA21. To introduce a c-Myc tag to the C-terminus of XA21, the EcoRI fragment of pKB-Myc-XA21-S was replaced by one with the tag fused to the C-terminus of XA21. The N-terminal c-Myc tag in the construct was replaced with 3×FLAG (DYKDDDDKGGDYKDDDDKGGDYKDDDDK; SEQ ID NO: 16) using the DraIII site. The 8.7 kb KpnI fragment containing Myc-Xa21-3×FLAG was then subcloned into the binary vector pCAMBIA1300. Agrobacterium-mediated rice transformation was performed using cultivar TP309 as recipient as described previously (Wang, et al., 2006, supra).

For protoplast transformation, enhanced green fluorescent protein (eGFP) with its own start codon removed was in-frame fused with XB3 between residues Thr-10 and Gly-11 to make pCR8GW-eGFP-XB3New-3×FLAG using primers SEQ ID NO: 22 (GTGTGGATCCATGGGT-CACGGTGTCAGCTGCGCCCGCACCCCTAGGGT-GAGCAAGG GCGAGGAG; GFP-F) and SEQ ID NO: 23 (GAATAGGGAATTCTCCCAGCCGAA; XB3seq-2). The XB3-mCherry fusion plasmid was constructed by replacing the C-terminal tag of XB3-3×FLAG in pCR8GW-XB3New-3×FLAG (Huang, et al., PLoS One 8: e63868, 2013) with mCherry fluorescent protein. The mCherry open reading frame was PCR amplified from pmCherry-C1 (Clontech) using primers mCherry-F (GTGCGGCCGCACTAGTG-GCGGAATGGTGAGCAAGGGCGAGGAGGA; SEQ ID NO: 30)/mCherry-R (GTAGATCTTTACTTGTACAGCT CGTCCATGCCGC; SEQ ID NO: 31). To generate the eGFP-XB3$^{G2A}$ mutant, PCR was carried out using primers XB3New-2 (GTTCTAGAAGATCTTCATAGATCGTGCT-CAGGCTTGTCCA; SEQ ID NO: 25)/XB3New-3 (GTTCTAGAGGATCCATGGCTCACGGTGTCAGCT-GCGCCCG; SEQ ID NO: 24) (carrying a mutation leading to substitution of Gly-2 in XB3 to Ala) and the mutated Xb3 gene was cloned into the vector pCR8GW (ThermoFisher Scientific). To construct the eGFP-XB3$^{nls}$ mutant, site-directed mutagenesis was performed using primers XB3NLS-3 (TGACAAGCCGTCATCCCTGCAACT-CACCCGGGAGGAGTCGGAACGATCTCACAACC TCAGTGAGG; SEQ ID NO: 26)/XB3NLS-4 (CCTCACT-GAGGTTGTGAGATCGTTCCGACTCCTCCCGGGT-GAGTTGCAGGGATGAC GGCTTGTCA; SEQ ID NO: 27) and the template plasmid pCR8GW-XB3New-3×FLAG. eGFP-Xb3 and its mutants were then cloned into the binary vector pCAMBIA1300S containing a rice gene expression cassette with a double cauliflower mosaic virus (CaMV) 35S promoter. To fuse a functional NLS (PKKKRKVG; SEQ ID NO: 17 from SV40 T antigen) to the C-terminus of Discosoma sp. red fluorescent protein (DsRed), PCR was carried out using primers DsRed-F (GTGTTCTAGAACTAGTA-TGGCCTCCTCCGAGGACGTCA; SEQ ID NO: 28)/ DsRed-R (GTGTTCTAGACTATCCCACCTTACGCTTT-TTCTTAGGTCCCAGGAACAGGTGGTGGC GGCC; SEQ ID NO: 29) to amplify DsRed-NLS. The resultant product was cloned into pCAMBIA1300S. The XA21-eGFP fusion was made by using NEBuilder® HiFi DNA Assembly Kit (New England Biolabs). The coding sequences for the Xa21 kinase domain and eGFP were PCR amplified using primer pairs Xa21eGFP-1 (CTGGATCATTTGGCT-CAGTATACA; SEQ ID NO: 18)/Xa21eGFP-2 (AAATT-CAAGGCTCCCACCTTCA; SEQ ID NO: 19) and Xa21 eGFP-3 (GGTGGGAGCCTTGAATTTGTCGACATGGT-GAGCAAGGGCGAGGA; SEQ ID NO: 20)/Xa21 eGFP-4 (TGATCGTGTGGTAGATACCACTGCAGTCAGTCG-ACCTTGTACAGCTCGTCCATGCCG A; SEQ ID NO: 21), respectively. Full-length Xa21-eGFP was assembled using the PCR products and a restriction fragment coding for the N-terminal half of XA21. The resultant gene was inserted into pCAMBIA1300S for protein expression in rice protoplasts.

For agrobacterium-mediated transient gene expression, Myc-Xa21 was generated by cloning a c-Myc-tagged Xa21 cDNA into pCAMBIA1300S. The plasmid pCAMBIA1303 was used to express the GUS-GFP-6×His fusion. pCAMBIA1300S-XB3-3×FLAG for expressing XB3-3× FLAG was described previously (Huang, et al., 2013, supra). All constructs were introduced into Agrobacterium tumefaciens strain EHA105. Infiltration of N. benthamiana was performed as described previously (Huang, et al., 2013, supra), except for tissue collection at 42 hours post infiltration. All constructs were verified by DNA sequencing.

Example 2—Transient Expression of Fluorescent Proteins in Rice Protoplasts

Rice protoplasts were isolated from cultivar TP309 as described (Zhang, et al., Plant Methods 7:30, 2011) except for the use of eight-day-old, dark-grown seedlings. Sixteen hours after transfection with the constructs described above, the protoplasts were visualized using a 40× objective with a Zeiss LSM800 confocal laser scanning microscope. N-(3 triethylammoniumpropyl)-4-(6-(4(diethylamino) phenyl) hexatrienyl) pyridinium dibromide (FM4-64) staining was performed by incubating the dye [final concentration 1% (v/v)] with transfected protoplasts for 10 min at room temperature. eGFP, DsRed, mCherry and FM4-64 were excited with 488, 561, 561 and 488 nm laser lines, respectively. Fluorescence emissions were captured at 410-535 nm for eGFP, at 410-585 nm for DsRed, at 600-617 nm for mCherry and at 650-700 nm for FM4-64. Images were analyzed using ZEN 2.0 software packages.

Example 3—Plant Growth and Treatments

Rice seeds were surface sterilized and germinated on half-strength Murashige-Skoog (MS) medium supplemented with 30 g/L sucrose (for wild-type) or the same medium with 30 g/L sucrose and 50 µg/ml hygromycin (for transgenic lines) for nine days at 25° C. under fluorescent light with a 16-hour photoperiod. Germinated seedlings of both Xa21-expressing lines and the vector control A36 were transferred into soil and grown in shared soil-holding trays prepared with evenly distributed holes on the bottom for absorbing water. The trays were maintained in large tanks filled with water in a greenhouse under nature light conditions in Gainesville, Fla. For drought treatments, the plant trays were transferred to a bench and kept under natural light conditions without watering for approximately 20-40 days depending on the season. To recover drought-stressed plants, the trays were returned to water tanks for 12 days before survivors were scored. RWC of drought-stressed leaves was determined using the equation: RWC=(FW−DW)/(TW−DW), where FW is the fresh weight of the leaf discs collected. Turgid weight (TW) was measured after floating the leaf discs on water for 24 hours at room temperature in dark. Dry weight (DW) was determined by weighing the leaves after drying at 65° C. for three days, which was adequate to assure complete drying of the biomass.

For seedling air-drying assays, germinated individuals were cultured in water for an additional two (for indica lines) and five (for transgenic japonica lines) days, respectively. Two-week-old japonica seedlings were air-dried in a growth chamber (23° C.) for three and half hours followed by a recovery in half-strength MS medium for three days. Survivors were defined as individuals possessing at least one true leaf flattened after recovery. A similar method, except that a five-hour-drought treatment and 11-day-old seedlings, was used to dehydrate the indica lines.

Example 4—Total RNA Extraction, RNA-Seq, q-PCR and RNA Blot Analyses

Transgenic A36 and B7-12 plants were subjected to drought stress treatments for 15 days at which point most of the treated A36 leaves, but not the B7-12 leaves, were rolled. Leaf tissues from five plants were harvested and pooled for each sample in order to minimize individual variations. Total RNA was extracted using the TRIzol Reagent (Ambion) according to the manufacturer's instruction. After treatment with RNase-free DNase (Qiagen) to eliminate genomic DNA contamination followed by further purification using RNeasy MinElute Cleanup Kit (Qiagen), the purified RNA was used for RNA-seq library construction and sequencing using the HiSeq 2000 platform (Illumina).

The obtained reads were aligned to the *O. sativa* Nipponbare reference genome using TopHat version 2.013 (Kawahara, et al., *Rice* 6:4, 2013; Trapnell, et al., *Bioinformatics* 25:1105-1111, 2009). Ambiguous reads that mapped to more than one region in the genome or those with a MAPQ score of less than 10 were removed. Transcript quantification was carried out by the Partek Genomics Suite (version 6.4, Partek, Inc.) to obtain raw read counts and normalized read counts (RPKM: Reads per kilobase per million mapped reads) (Mortazavi, et al., *Nat. Methods* 5:621-628, 2008). Differential gene expression was analyzed using generalized linear model approaches (GLM) implemented in the BioConductor edgeR package. Significant differential expression genes (DEGs) were selected based on the following criteria: fold change over 2, p-value less than 0.05 and RPKM greater than 1 for B7-12 in up-regulation or RPKM greater 1 for A36 in down-regulation.

For q-PCR analysis, two-week-old seedlings were subjected to dehydration followed by RNA isolation as described above. cDNA was synthesized with 1 µg of total RNA using RT$^2$ First Strand Kit (Qiagen). Q-PCR was performed under the following conditions: 95° C., 2 min; (95° C., 5 s; 60° C., 5 s)×40 cycles, 72° C., 5 min using the CFX 96 Real-Time PCR Detection System (Bio-Rad) according to the manufacturer's instruction. Results were normalized to the expression of the rice reference gene Os06g11170.1 (Narsai, et al., *BMC Plant Biol.* 10:56, 2010). Primer sequences SEQ ID NO: 7 (GTACATCTAGATTTGGGGTAGA; forward) and SEQ ID NO: 8 (GTACGAACACAAGCTAACACGA; reverse) were used for OsLEA1, SEQ ID NO: 9 (CCAAGCAGAAGACCGCCGA; forward) and SEQ ID NO: 10 (GTCATCCCCAGCGTGCTCA; reverse) were used for OsLEA3, SEQ ID NO: 11 (CGATGACGACGCTGAGTGAA; forward) and SEQ ID NO: 12 (CAGGTGACATCACACGCTTGA; reverse) were used for OsLEA33, SEQ ID NO: 13 (TAACAGCACCACCACCACAA; forward) and SEQ ID NO: 14 (GTCTTCAAGCTGTTCGACGG; reverse) were used for OsNAC10, and SEQ ID NO: 5 (GGAATGTGGACGGTGACACT; forward) and SEQ ID NO: 6 (TCAAAATAGAGTCCAGTAGATTTGTCA; reverse) were used for Os06g11170.1.

RNA blot analysis was performed using a radiolabeled Xb3-specific probe as described previously (Wang, et al., 2006, supra).

Example 5—Immunodetection

To generate monoclonal anti-XA21K antibody, the intracellular kinase domain of XA21 was expressed in *E. coli* and the purified fusion protein was used as immunogen in mice. Antibody production was performed as described (Rong, et al., *J. Integrative Agricultural* 15:726-734, 2016).

Nuclear fraction was isolated by homogenization of leaf tissues in 1× nuclei isolation buffer (2.5% Ficoll 400, 0.4 M sucrose, 25% glycerol, 25 mM Tris-HCl, pH 7.5, 10 mM MgCl2, 1 mM DTT, 1 mM PMSF, and 1× complete protease inhibitor cocktail) using a mortar and pestle. The homogenate was sequentially filtered through one-layer of 75 µm nylon mesh, two-layers of miracloth (Millipore) and four-layers of miracloth. After addition of Triton X-100 to a final concentration of 0.5%, the homogenate was incubated on ice for 15 min and centrifuged at 1,500 g for 5 min. The supernatant was saved as a nuclei-depleted fraction and the pellet was washed with washing buffer (lx nuclei isolation buffer containing 0.1% Triton X-100) and centrifuged at 100×g for 1 min to remove starch and cell debris. The pellet was further washed three times using washing buffer, and then resuspended in 1 ml of washing buffer. After centrifuging at 1,800×g for 5 min, the nuclei-enriched pellet was collected.

Microsomal fraction was isolated by homogenization of leaf tissue harvested from two-month-old plants in 1× extraction buffer (50 mM Tris-HCl, pH 7.5; 150 mM NaCl; 1 mM EDTA; 10% glycerol; 1 mM PMSF, and 1× complete protease inhibitor cocktail), filtrated through Miracloth, and centrifuged at 1,000×g for 10 min at 4° C. The supernatant was re-centrifuged at 15,000×g for 5 min at 4° C. The resultant supernatant was centrifuged at 150,000×g for 60 min at 4° C. The pellet was re-suspended in solubilization buffer (extraction buffer containing 0.1% Triton X-100, but lacking glycerol) and stored at −70° C. until used.

Protein extraction and protein blot analysis was performed as previously described (Xu, et al., *Plant J.* 45:740-751, 2006).

Example 6—Inoculation of Plants with Xoo

Six-week-old plants were inoculated with Xoo strains using the leaf-clipping method (Kauffman, et al., *Plant Disease Rep.* 57:537-541, 1993). After inoculation, disease lesion development and bacterial population were determined as described previously (Song, et al., *Science* 270:1804-1806, 1995).

Example 7—Xa21 Confers Drought Tolerance in Rice

Figure 1B:
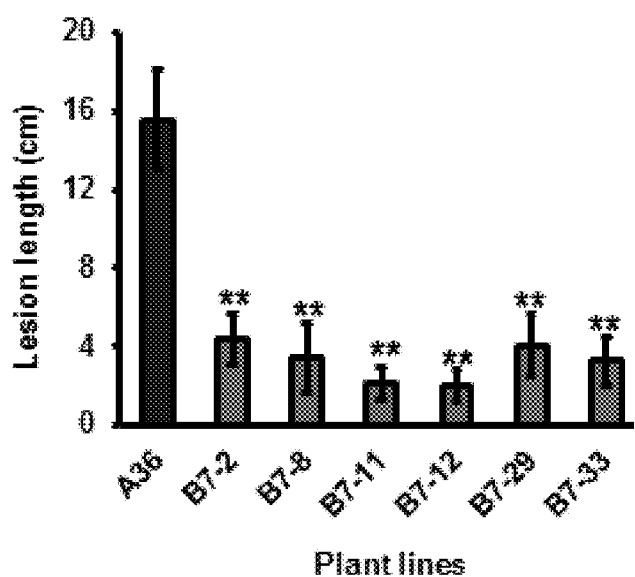
FIG. 1B. Lesion length data of inoculated plants (n=11 each line). The asterisk signs indicate statistically significant difference from the control A36 as calculated by Student's t test (**: $p<0.01$).

After infection, incompatible Xoo strains (e.g., PXO99A) can propagate to a significant level in rice; but they cause short disease lesions and weak water stress injuries (FIG. 2). The inventors reasoned that Xa21 might play a role in counteracting drought, although an immune sensor has never before been assigned a similar function under physiological conditions. The ability of Xa21 to confer drought tolerance was tested in the absence of Xoo. Newly generated Xa21 lines (B7-12 and B7-11) and the empty-vector control A36 [both using cultivar *O. sativa* ssp. *japonica* cv. Tai-Pei309 (TP309) as recipient] were stressed by withholding water. The Xa21 lines, expressing 3×FLAG-Xa21-Myc under the control of its native promoter, conferred resistance to PXO99A (FIG. 1B). Remarkably, Xa21 plants displayed delayed drought-related symptoms and were recovered from the water stress with significantly higher survival rates than A36. The tolerance appeared to be influenced by the seasons and developmental stages with greater degree in winter and at the older stages. The leaf water status of stressed plants was measured and it was confirmed that the B7-12 line was able to maintain higher levels of relative water content (RWC) than did A36 during drought conditions (FIG. 3A).

The novel function of XA21 was confirmed in temperature-controlled laboratory settings. Air-drying of two-week-old seedlings for three and half hours at 23° C. induced more than 54% mortality in A36, but caused less than 25% death in B7-12, B7-11 and the previously characterized line 4021-3 with a higher level of Myc-XA21 (FIG. 3B; FIG. 4A; FIG. 4B; Wang, et al., 2006, supra). Relative to the near-isogenic recurrent parent IR24 (*O. sativa* ssp. *indica*), the Xa21 introgression line IRBB21 (the original source for isolating the Xa21 gene, Khush, et al., *Rice Genetics Newsletter* 7:121-122, 1990) as well as IRBB14 seedlings, which carry the genetically-characterized BLB resistance gene Xa14 (Taura, et al., *Rice Genetics Newsletter* 4:101-102, 1987), exhibit better performance after five hour of drought treatment (FIG. 4C; FIG. 3C). By contrast, IRBB13 seedlings containing the recessive resistance gene xa13 coding for a sugar transporter (Chu, et al., *Genes Dev.* 20:1250-1255, 2006; Yang, et al., *Proc. Natl. Acad. Sci. USA* 103: 10503-10508, 2006; Chen, et al., *Annu. Rev. Biochem.* 84:865-894, 2015) are sensitive to water stress (FIG. 5).

Example 8—Water Deficit Induces Heightened Expression of Drought Stress-Related Genes in an Xa21 Dependent Manner To determine the molecular mechanisms underlying Xa21-mediated drought response, RNA-seq analysis was performed. Adult plants were drought-stressed under greenhouse conditions for 15 days at which point most of the treated A36 leaves, but not the B7-12 leaves, were rolled, a phenotypic sign of early stage water deficit. Total RNA was isolated and subjected to library construction and sequencing. More than 61 million reads were generated from each sample and the obtained reads were aligned to the *O. sativa* Nipponbare reference genome using TopHat version 2.013 (Kawahara, et al., 2013, supra; Trapnell, et al., 2009, supra). A total of 430 differentially expressed genes (DEGs) were identified between B7-12 and A36 after drought treatment, with 17 of them previously known to be water stress regulated (Table 1). In Table 1, known drought/dehydration-responsive genes are indicated in bold, genes whose differential expression was validated by q-PCR are indicated in bold and underlining, and known drought/dehydration-responsive genes whose differential expression was validated by q-PCR are underlined (no bold). Fold change and p-value were generated by edgeR, and RPKM value is average value for each line. Real-time quantitative reverse transcription-PCR (q-PCR) validated the drought induction and differential expression of four DEGs (OsLEA1, OsLEA3, OsLEA33 and OsNAC10) (FIG. 6A, FIG. 6B, FIG. 6C and FIG. 6D, respectively). These data indicate that in response to water stress Xa21 triggers heightened expression of a battery of drought-responsive genes.

TABLE 1

| Gene model | Annotation | Fold change drought (B7-12/A36) | p-value | B7-12 (RPKM) | A36 (RPKM) |
| --- | --- | --- | --- | --- | --- |
| Os08g36740.1 | bHelix-loop-helix transcription factor, putative, expressed | 65.60 | 0.014347791 | 1.05888 | 0.0101797 |
| Os02g20940.2 | CHCH domain containing protein, expressed | 64.92 | 0.015035143 | 1.31103 | 0.0123909 |
| Os07g48450.2 | NAC domain transcription factor | 57.63 | 2.91E−07 | 3.48369 | 0.0360582 |
| Os07g40460.2 | prefoldin, putative, expressed | 57.40 | 0.025212223 | 1.39779 | 0.0133264 |
| Os05g47860.1 | expressed protein | 56.03 | 0.027707752 | 1.30644 | 0.014704 |
| Os06g42430.2 | expressed protein | 46.81 | 0.004351535 | 1.62423 | 0.0252887 |
| Os08g18974.2 | expressed protein | 36.56 | 0.015416347 | 1.47982 | 0.0254192 |
| Os01g65090.1 | aminotransferase, classes I and II, domain containing protein, expressed | 32.25 | 4.74E−06 | 2.51309 | 0.0474212 |
| Os02g58730.2 | ras-related protein, putative, expressed | 27.11 | 0.014580597 | 1.13705 | 0.0277986 |
| Os03g17870.1 | metallothionein, putative, expressed (related to OsMT1a) | 25.45 | 0.006840116 | 5.56079 | 0.137775 |
| Os05g47730.1 | LTPL153 - Protease inhibitor/seed storage/LTP family protein precursor, expressed | 19.93 | 7.64E−07 | 15.8955 | 0.502877 |
| Os11g25040.1 | plant-specific domain TIGR01615 family protein, expressed | 17.47 | 0.006340921 | 1.35904 | 0.0490498 |
| Os08g31860.1 | expressed protein | 15.54 | 3.00E−09 | 23.074 | 0.936311 |
| Os03g08360.1 | 3-ketoacyl-CoA synthase 10, putative, expressed | 15.35 | 4.78E−05 | 2.42981 | 0.100974 |
| Os04g33920.1 | LTPL102 - Protease inhibitor/seed storage/LTP family protein precursor, expressed | 14.33 | 1.17E−08 | 35.8224 | 1.57634 |
| Os01g62420.3 | triosephosphate isomerase, cytosolic, putative, expressed | 12.90 | 0.01944993 | 1.73492 | 0.0852586 |
| Os05g31140.2 | glycosyl hydrolases family 17, putative, expressed | 12.43 | 2.42E−07 | 12.3571 | 0.626934 |
| Os05g11320.1 | metallothionein-like protein 3B, putative, expressed | 12.30 | 1.57E−09 | 691.652 | 35.4509 |
| Os10g38470.1 | glutathione S-transferase, putative, expressed | 11.44 | 2.51E−07 | 21.5953 | 1.19037 |
| Os08g44270.1 | vignain precursor, putative, expressed | 11.28 | 0.018962743 | 1.03103 | 0.0576694 |
| Os07g23640.1 | retrotransposon protein, putative, Ty3-gypsy subclass, expressed | 11.10 | 0.004396684 | 2.18513 | 0.124103 |

TABLE 1-continued

| Gene model | Annotation | Fold change drought (B7-12/A36) | p-value | B7-12 (RPKM) | A36 (RPKM) |
|---|---|---|---|---|---|
| Os01g45640.1 | tat pathway signal sequence family protein, expressed | 10.95 | 4.59E−08 | 73.6573 | 4.24383 |
| Os11g18570.1 | cytochrome P450, putative, expressed | 10.78 | 4.03E−06 | 6.69536 | 0.391673 |
| Os12g09300.1 | amino acid transporter, putative, expressed | 10.78 | 0.000118804 | 3.17876 | 0.185964 |
| Os04g33510.1 | expressed protein | 10.75 | 0.01806747 | 1.66628 | 0.101577 |
| Os01g46120.1 | GDSL-like lipase/acylhydrolase, putative, expressed | 10.61 | 0.004705021 | 1.64294 | 0.0968729 |
| Os01g62420.1 | triosephosphate isomerase, cytosolic, putative, expressed | 10.50 | 0.020205805 | 1.26389 | 0.0724757 |
| Os01g43740.1 | cytochrome P450 72A1, putative, expressed | 9.72 | 0.006632195 | 1.15791 | 0.0751394 |
| Os09g29660.1 | white-brown complex homolog protein 11, putative, expressed | 9.69 | 0.000123738 | 2.50208 | 0.162849 |
| Os10g35070.4 | alpha-galactosidase precursor, putative, expressed | 9.40 | 0.004817214 | 2.52422 | 0.167932 |
| Os12g41680.1 | NAC domain transcription factor | 8.82 | 8.61E−06 | 10.5794 | 0.756102 |
| Os01g03730.1 | nuclease PA3, putative, expressed | 8.72 | 5.59E−06 | 14.1191 | 1.02108 |
| Os01g43372.1 | expressed protein | 8.64 | 0.000127875 | 3.45949 | 0.251629 |
| Os05g48510.1 | phenylalanyl-tRNA synthetase beta chain, putative, expressed | 8.60 | 0.005416772 | 1.08485 | 0.0800341 |
| <u>Os05g46480.2</u> | <u>late embryogenesis abundant protein, group 3, putative, expressed (OsLEA3)</u> | <u>8.42</u> | <u>1.08E−05</u> | <u>18.4447</u> | <u>1.38329</u> |
| Os07g37690.1 | UDP-glucoronosyl and UDP-glucosyl transferase domain containing protein, expressed | 8.42 | 0.012705122 | 1.21277 | 0.0908814 |
| Os02g16000.1 | E1-BTB1 - Bric-a-Brac, Tramtrack, and Broad Complex domain with E1 subfamily conserved sequence, expressed | 8.41 | 0.001700045 | 1.86881 | 0.138122 |
| Os01g73830.1 | expressed protein | 8.11 | 0.028925119 | 1.32138 | 0.102768 |
| Os01g68290.1 | expressed protein | 8.07 | 2.86E−07 | 408.154 | 31.9028 |
| Os01g06310.1 | glycine-rich cell wall structural protein precursor, putative, expressed | 8.06 | 1.41E−06 | 66.2272 | 5.18048 |
| Os12g33130.1 | expressed protein | 7.81 | 1.44E−06 | 119.968 | 9.68975 |
| Os03g18850.1 | pathogenesis-related Bet v I family protein, putative, expressed | 7.80 | 0.001346482 | 6.01608 | 0.486655 |
| Os08g19420.1 | O-methyltransferase, putative, expressed | 7.62 | 1.94E−05 | 11.9352 | 0.987687 |
| Os06g49660.1 | transferase family protein, putative, expressed | 7.43 | 0.004939444 | 1.95157 | 0.165563 |
| Os06g46270.1 | NAC domain transcription factor | 7.40 | 0.0320483 | 1.26111 | 0.107533 |
| Os01g55940.1 | OsGH3.2 - Probable indole-3-acetic acid-amido synthetase, expressed | 7.14 | 9.95E−05 | 4.82056 | 0.425924 |
| Os06g36390.2 | expressed protein | 7.04 | 0.000893281 | 4.66685 | 0.418074 |
| Os12g07970.2 | transporter, major facilitator family, putative, expressed | 6.86 | 0.019455049 | 1.20617 | 0.110105 |
| <u>Os04g49980.1</u> | <u>late embryogenesis abundant group 1, putative, expressed (OsLEA1)</u> | <u>6.66</u> | <u>0.000841869</u> | <u>10.3023</u> | <u>0.975863</u> |
| Os02g28170.1 | transferase family protein, putative, expressed | 6.49 | 0.01744985 | 1.28606 | 0.124938 |
| Os01g42860.1 | inhibitor I family protein, putative, expressed | 6.45 | 0.049838642 | 3.9417 | 0.385182 |
| Os11g40530.1 | LTPL162 - Protease inhibitor/seed storage/LTP family protein precursor, expressed | 6.30 | 7.07E−06 | 179.129 | 17.9183 |
| Os01g09220.1 | transposon protein, putative, CACTA, En/Spm sub-class, expressed | 5.88 | 0.019435644 | 1.45257 | 0.155772 |
| Os04g54330.1 | acetyltransferase, GNAT family, putative, expressed | 5.82 | 0.045569669 | 1.40486 | 0.153768 |
| Os03g08550.1 | STRUBBELIG-RECEPTOR FAMILY 6 precursor, putative, expressed | 5.80 | 0.002096038 | 2.17117 | 0.234815 |
| Os03g20870.1 | zinc finger, C3HC4 type domain containing protein, expressed | 5.79 | 0.000419056 | 7.89185 | 0.859687 |
| Os05g43300.1 | expressed protein | 5.78 | 0.00324686 | 2.50565 | 0.27477 |
| Os08g31340.1 | heavy metal-associated domain containing protein, expressed | 5.76 | 0.010627881 | 2.69415 | 0.29489 |
| Os04g54330.3 | acetyltransferase, GNAT family, putative, expressed | 5.74 | 0.04074359 | 1.50025 | 0.1642 |
| Os07g10420.1 | expressed protein | 5.66 | 4.95E−05 | 39.7652 | 4.43137 |
| Os03g43720.1 | transporter family protein, putative, expressed | 5.61 | 0.006395436 | 2.00027 | 0.226837 |
| Os12g38270.1 | metallothionein, putative, expressed (related to OsMT1a) | 5.53 | 0.000403064 | 22.7044 | 2.58901 |

TABLE 1-continued

| Gene model | Annotation | Fold change drought (B7-12/A36) | p-value | B7-12 (RPKM) | A36 (RPKM) |
|---|---|---|---|---|---|
| Os10g34614.1 | csAtPR5, putative, expressed | 5.49 | 0.039014666 | 1.34781 | 0.152235 |
| Os05g07940.1 | glyoxalase family protein, putative, expressed | 5.46 | 0.000258157 | 13.8468 | 1.60099 |
| Os02g08440.1 | WRKY71, expressed | 5.38 | 0.03227178 | 1.41166 | 0.164446 |
| Os03g04500.1 | tetratricopeptide repeat domain containing protein, expressed | 5.33 | 0.021962974 | 1.04358 | 0.124314 |
| Os03g55590.1 | MYB family transcription factor, putative, expressed | 5.28 | 9.62E−05 | 18.0639 | 2.15755 |
| Os12g42910.1 | sodium/calcium exchanger protein, putative, expressed | 5.26 | 0.013891386 | 1.61749 | 0.194023 |
| Os08g35620.1 | HD domain containing protein, putative, expressed | 5.23 | 0.01181755 | 1.29624 | 0.156381 |
| Os04g38680.1 | transmembrane amino acid transporter protein, putative, expressed | 5.23 | 0.000612057 | 7.00345 | 0.844909 |
| Os04g58750.3 | protein kinase family protein, putative, expressed | 5.23 | 0.010002973 | 2.09933 | 0.251298 |
| Os05g01280.2 | expressed protein | 5.08 | 0.041787996 | 4.1354 | 0.508973 |
| Os02g36974.2 | 14-3-3 protein, putative, expressed | 5.07 | 0.002758265 | 5.64025 | 0.70212 |
| Os01g53240.1 | BURP domain containing protein, expressed | 5.07 | 0.000123555 | 22.1057 | 2.7515 |
| Os01g66100.1 | gibberellin 20 oxidase 2 (semi-dwarfing gene SD1) | 4.91 | 0.0045523 | 4.05657 | 0.521365 |
| Os06g23350.1 | late embryogenesis abundant protein D-34, putative, expressed (OsLEA33) | 4.90 | 0.013580481 | 3.53686 | 0.45529 |
| Os02g16630.1 | tryptophan biosynthesis protein trpCF, putative, expressed | 4.87 | 0.034101964 | 1.78049 | 0.228005 |
| Os04g42250.3 | transferase family protein, putative, expressed | 4.86 | 0.0027841 | 4.33123 | 0.561044 |
| Os01g27020.3 | transposon protein, putative, unclassified, expressed | 4.76 | 0.046556802 | 1.02605 | 0.134374 |
| Os05g23440.2 | solute carrier family 35 member F1, putative, expressed | 4.74 | 0.027841494 | 2.05889 | 0.273971 |
| Os04g02900.2 | dehydrogenase E1 component domain containing protein, expressed | 4.70 | 0.000341814 | 14.179 | 1.90125 |
| Os02g42290.3 | OsClp3 - Putative Clp protease homologue, expressed | 4.66 | 0.000410464 | 19.8523 | 2.68277 |
| Os03g07130.1 | RING finger protein 13, putative, expressed | 4.65 | 0.015820352 | 1.75596 | 0.23755 |
| Os07g47450.1 | flowering promoting factor-like 1, putative, expressed | 4.41 | 0.006286889 | 15.6035 | 2.23356 |
| Os05g45090.1 | anthocyanidin 5,3-O-glucosyltransferase, putative, expressed | 4.38 | 0.044069989 | 1.4007 | 0.201701 |
| Os05g15770.1 | glycosyl hydrolase, putative, expressed | 4.35 | 0.000540829 | 25.293 | 3.66743 |
| Os10g25130.1 | aminotransferase, classes I and II, domain containing protein, expressed | 4.32 | 0.001426589 | 7.73144 | 1.12752 |
| Os05g09600.3 | GA11916-PA, putative, expressed | 4.32 | 0.030862698 | 3.39147 | 0.498372 |
| Os05g49940.1 | expressed protein | 4.14 | 0.001070071 | 35.3562 | 5.37991 |
| Os05g07940.5 | glyoxalase family protein, putative, expressed | 4.13 | 0.00368885 | 10.1542 | 1.548 |
| Os08g08960.1 | Cupin domain containing protein, expressed | 4.12 | 0.027926452 | 3.87949 | 0.593737 |
| Os02g55590.1 | expressed protein | 4.07 | 0.011803933 | 2.68421 | 0.414516 |
| Os01g46600.1 | seed maturation protein PM41, putative, expressed | 4.06 | 0.003422302 | 41.6122 | 6.46556 |
| Os02g07230.2 | porphobilinogen deaminase, chloroplast precursor, putative, expressed | 4.05 | 0.028910079 | 2.56107 | 0.401008 |
| Os01g72890.2 | transposon protein, putative, CACTA, En/Spm sub-class, expressed | 4.03 | 0.019251511 | 2.75861 | 0.42939 |
| Os10g18150.1 | crooked neck, putative, expressed | 4.02 | 0.018603025 | 1.86837 | 0.292938 |
| Os09g29710.1 | beta-expansin precursor, putative, expressed | 4.02 | 0.041299195 | 4.5672 | 0.717197 |
| Os05g08980.3 | expressed protein | 4.00 | 0.007464156 | 5.90306 | 0.929681 |
| Os09g21120.1 | armadillo/beta-catenin repeat family protein, putative, expressed | 4.00 | 0.017785079 | 1.85889 | 0.293372 |
| Os07g04220.1 | wound and phytochrome signaling involved receptor like kinase, putative, expressed | 3.93 | 0.043253877 | 1.08147 | 0.17371 |
| Os09g33810.2 | ankyrin repeat domain containing protein, putative, expressed | 3.92 | 0.009507488 | 4.72312 | 0.76076 |
| Os04g33500.1 | protein kinase, putative, expressed | 3.92 | 0.035154191 | 2.07574 | 0.334254 |
| Os01g59600.2 | peptidase, T1 family, putative, expressed | 3.92 | 0.026888423 | 3.62538 | 0.583029 |
| Os04g55850.1 | nuclease PA3, putative, expressed | 3.89 | 0.003666708 | 11.3396 | 1.84064 |
| Os09g19940.2 | cwfJ-like family protein, putative, expressed | 3.87 | 0.048843213 | 1.31393 | 0.214269 |
| Os10g39920.1 | expressed protein | 3.85 | 0.006408314 | 12.0164 | 1.9664 |

TABLE 1-continued

| Gene model | Annotation | Fold change drought (B7-12/A36) | p-value | B7-12 (RPKM) | A36 (RPKM) |
|---|---|---|---|---|---|
| Os02g32520.1 | early-responsive dehydration 1 (ERD1) protein | 3.85 | 0.004053087 | 3.76972 | 0.618829 |
| Os10g38610.1 | glutathione S-transferase, putative, expressed | 3.83 | 0.007759607 | 8.05908 | 1.32678 |
| Os03g08580.1 | expressed protein | 3.80 | 0.008598883 | 7.34964 | 1.21944 |
| Os01g08440.1 | UDP-glucoronosyl and UDP-glucosyl transferase domain containing protein, expressed | 3.79 | 0.009586004 | 4.33448 | 0.721899 |
| Os04g10680.3 | zinc finger, C3HC4 type domain containing protein, expressed | 3.70 | 0.041016557 | 1.24967 | 0.212153 |
| Os01g51010.1 | DUF292 domain containing protein, expressed | 3.70 | 0.032642746 | 1.00933 | 0.172579 |
| Os05g10940.1 | metal cation transporter, putative, expressed | 3.68 | 0.013041639 | 4.15535 | 0.712355 |
| Os03g03810.1 | DEF8 - Defensin and Defensin-like DEFL family, expressed | 3.67 | 0.002356129 | 56.5489 | 9.72839 |
| Os07g36465.1 | vacuolar ATP synthase subunit H, putative, expressed | 3.65 | 0.045822573 | 6.42183 | 1.10929 |
| Os11g47809.1 | metallothionein, putative, expressed (OsMT1a) | 3.63 | 0.001210069 | 156.213 | 27.1128 |
| Os01g70920.2 | cullin-1, putative, expressed | 3.62 | 0.040235358 | 2.53091 | 0.442728 |
| Os05g34830.3 | NAC domain transcription factor | 3.59 | 0.010772328 | 6.60158 | 1.16018 |
| Os01g65480.1 | dnaJ domain containing protein, expressed | 3.57 | 0.016264368 | 4.51583 | 0.797834 |
| Os09g26620.4 | auxin-repressed protein, putative, expressed | 3.57 | 0.039860726 | 5.27219 | 0.926879 |
| Os01g19150.5 | CGMC_GSK.3 - CGMC includes CDA, MAPK, GSK3, and CLKC kinases, expressed | 3.55 | 0.032144494 | 2.3096 | 0.410895 |
| Os06g37010.2 | metal cation transporter, putative, expressed | 3.53 | 0.035643776 | 2.62741 | 0.46961 |
| Os10g33960.2 | START domain containing protein, expressed | 3.52 | 0.024508117 | 1.76838 | 0.317967 |
| Os04g52450.1 | aminotransferase, putative, expressed | 3.46 | 0.005097202 | 8.77895 | 1.59814 |
| Os06g03660.1 | peroxisomal biogenesis factor 11, putative, expressed | 3.44 | 0.010123999 | 6.15175 | 1.12762 |
| <u>Os11g03300.2</u> | <u>NAC domain transcription factor (OsNAC10)</u> | <u>3.42</u> | <u>0.043369255</u> | <u>3.19666</u> | <u>0.590187</u> |
| Os07g48830.2 | glycosyl transferase 8 domain containing protein, putative, expressed | 3.36 | 0.003255207 | 29.1802 | 5.47601 |
| Os02g12650.1 | puromycin-sensitive aminopeptidase, putative, expressed | 3.33 | 0.005200384 | 7.0731 | 1.33811 |
| Os01g09300.3 | oxidoreductase, putative, expressed | 3.31 | 0.040225522 | 3.25537 | 0.622002 |
| Os03g61920.1 | electron transfer flavoprotein subunit alpha, mitochondrial precursor, putative, expressed | 3.30 | 0.007785135 | 10.1092 | 1.93468 |
| Os04g56110.1 | protein kinase, putative, expressed | 3.29 | 0.009049751 | 8.07154 | 1.54822 |
| Os04g53690.1 | expressed protein | 3.29 | 0.036186551 | 4.03281 | 0.77431 |
| Os09g34280.1 | ankyrin repeat-containing protein, putative, expressed | 3.25 | 0.010233398 | 5.23619 | 1.01564 |
| Os07g48160.1 | alpha-galactosidase precursor, putative, expressed | 3.23 | 0.020628362 | 4.7077 | 0.918123 |
| Os04g54830.1 | expressed protein | 3.19 | 0.033398369 | 2.32475 | 0.459516 |
| Os01g37750.1 | glutathione S-transferase, putative, expressed | 3.18 | 0.0105181 | 14.6467 | 2.90378 |
| Os10g11810.1 | dehydrogenase, putative, expressed | 3.11 | 0.022703831 | 5.79326 | 1.17309 |
| Os08g05570.3 | monodehydroascorbate reductase, putative, expressed | 3.11 | 0.019060015 | 4.55583 | 0.926648 |
| Os03g50290.1 | 14-3-3 protein, putative, expressed | 3.09 | 0.005406408 | 31.7782 | 6.47917 |
| Os04g58360.1 | expressed protein | 3.09 | 0.025484871 | 18.1069 | 3.69421 |
| Os03g17930.2 | alpha-taxilin, putative, expressed | 3.06 | 0.047655945 | 3.01106 | 0.621429 |
| Os02g57840.2 | remorin C-terminal domain containing protein, putative, expressed | 3.05 | 0.021179187 | 11.2032 | 2.31616 |
| Os08g38880.4 | WD-40 repeat family protein, putative, expressed | 3.04 | 0.012817107 | 9.44055 | 1.95841 |
| Os01g53880.5 | OsIAA6 - Auxin-responsive Aux/IAA gene family member, expressed | 3.02 | 0.017470191 | 6.78062 | 1.41427 |
| Os05g34830.1 | NAC domain transcription factor | 3.02 | 0.012973598 | 11.6291 | 2.426 |
| Os05g03920.1 | TKL_IRAK_DUF26-lf.3 - DUF26 kinases have homology to DUF26 containing loci, expressed | 3.02 | 0.014560547 | 5.98364 | 1.25081 |
| Os12g03470.4 | alpha-N-arabinofuranosidase A, putative, expressed | 3.02 | 0.028865128 | 2.99124 | 0.626884 |
| Os09g28050.1 | asparate aminotransferase, putative, expressed | 3.01 | 0.00959124 | 13.2161 | 2.7631 |

TABLE 1-continued

| Gene model | Annotation | Fold change drought (B7-12/A36) | p-value | B7-12 (RPKM) | A36 (RPKM) |
|---|---|---|---|---|---|
| Os11g03780.2 | alpha-N-arabinofuranosidase, putative, expressed | 3.00 | 0.011278122 | 8.13877 | 1.71027 |
| Os04g33590.1 | hydrolase, alpha/beta fold family protein, putative, expressed | 2.99 | 0.044269298 | 3.8648 | 0.816558 |
| Os11g40090.2 | A49-like RNA polymerase I associated factor family protein, expressed | 2.98 | 0.024667002 | 5.07588 | 1.07563 |
| Os06g10750.1 | integral membrane protein DUF6 containing protein, expressed | 2.96 | 0.01881857 | 7.51249 | 1.59882 |
| Os08g35740.1 | 12-oxophytodienoate reductase, putative, expressed | 2.95 | 0.016204039 | 9.46148 | 2.02497 |
| Os09g31130.1 | citrate transporter, putative, expressed | 2.94 | 0.041760309 | 2.64974 | 0.568961 |
| Os03g44900.1 | CCR4-NOT transcription factor, putative, expressed | 2.93 | 0.043888981 | 2.01017 | 0.432212 |
| Os09g21230.2 | AMP-binding enzyme, putative, expressed | 2.87 | 0.011871401 | 11.3363 | 2.49409 |
| <u>Os05g46480.1</u> | <u>late embryogenesis abundant protein, group 3, putative, expressed (OsLEA3)</u> | <u>2.84</u> | <u>0.008633078</u> | <u>70.9919</u> | <u>15.7612</u> |
| Os01g63990.2 | hydrolase, alpha/beta fold family protein, putative, expressed | 2.84 | 0.011984955 | 20.3489 | 4.51509 |
| Os01g59000.1 | cytochrome P450, putative, expressed | 2.84 | 0.026288698 | 6.02527 | 1.33845 |
| Os02g52560.1 | xyloglucan fucosyltransferase, putative, expressed | 2.83 | 0.019421299 | 7.09289 | 1.57996 |
| Os10g41060.1 | expressed protein | 2.81 | 0.034573323 | 4.15975 | 0.932969 |
| Os12g03040.1 | NAC domain transcription factor | 2.80 | 0.022774518 | 7.96675 | 1.79473 |
| Os04g35060.1 | nicotinate phosphoribosyltransferase family domain containing protein, expressed | 2.80 | 0.026759488 | 5.27013 | 1.18742 |
| Os08g03290.1 | glyceraldehyde-3-phosphate dehydrogenase, putative, expressed | 2.79 | 0.007669592 | 174.12 | 39.3703 |
| Os07g12150.1 | acyl carrier protein, putative, expressed | 2.76 | 0.040950598 | 11.6442 | 2.65945 |
| Os05g42210.1 | serine/threonine-protein kinase receptor precursor, putative, expressed | 2.75 | 0.018907713 | 6.76181 | 1.54937 |
| Os09g11460.2 | AP2 domain containing protein, expressed | 2.75 | 0.024284631 | 9.94016 | 2.27893 |
| Os06g24730.1 | hydrolase, alpha/beta fold family domain containing protein, expressed | 2.75 | 0.009674252 | 47.9783 | 11.0139 |
| Os06g41930.3 | zinc-binding protein, putative, expressed | 2.73 | 0.036007727 | 6.44591 | 1.48721 |
| Os06g47200.1 | LTPL85 - Protease inhibitor/seed storage/LTP family protein precursor, expressed | 2.70 | 0.027390758 | 20.0421 | 4.6762 |
| Os02g56850.1 | glutathione reductase, putative, expressed | 2.70 | 0.019441752 | 11.4648 | 2.68255 |
| Os01g50450.1 | expressed protein | 2.68 | 0.023521504 | 14.7349 | 3.46828 |
| Os07g13270.1 | SNF7 domain containing protein, putative, expressed | 2.64 | 0.025151051 | 18.5537 | 4.43033 |
| Os04g49757.1 | purine permease, putative, expressed | 2.63 | 0.037495399 | 7.75265 | 1.86432 |
| Os02g15860.1 | expressed protein | 2.62 | 0.015275712 | 187.296 | 45.0737 |
| Os01g62060.1 | plant-specific domain TIGR01589 family protein, expressed | 2.58 | 0.040598341 | 17.8803 | 4.36682 |
| Os03g56460.1 | glucose-6-phosphate isomerase, putative, expressed | 2.57 | 0.039210869 | 5.37327 | 1.32074 |
| Os04g55720.2 | D-3-phosphoglycerate dehydrogenase, chloroplast precursor, putative, expressed | 2.55 | 0.021651388 | 16.1942 | 4.00543 |
| Os01g17190.1 | OsCam3 - Calmodulin, expressed | 2.54 | 0.02590334 | 33.2291 | 8.24689 |
| Os05g46560.2 | RAN GTPase-activating protein 1, putative, expressed | 2.53 | 0.033625822 | 8.10648 | 2.0235 |
| Os01g07950.1 | OsGrx_S15.2 - glutaredoxin subgroup II, expressed | 2.53 | 0.03846351 | 15.8821 | 3.96206 |
| Os04g56160.1 | plasma membrane ATPase, putative, expressed | 2.53 | 0.031998692 | 5.10151 | 1.27298 |
| Os01g58380.1 | 3-hydroxybutyryl-CoA dehydrogenase, putative, expressed | 2.51 | 0.028660723 | 18.6086 | 4.66751 |
| Os06g48500.1 | expressed protein | 2.51 | 0.031334088 | 13.4713 | 3.38703 |
| Os05g24550.4 | Papain family cysteine protease domain containing protein, expressed | 2.50 | 0.017546457 | 117.503 | 29.6923 |
| Os03g05310.1 | pheophorbide a oxygenase, chloroplast precursor, putative, expressed | 2.48 | 0.021235417 | 27.755 | 7.05028 |
| Os10g35070.1 | alpha-galactosidase precursor, putative, expressed | 2.46 | 0.019744005 | 103.457 | 26.5642 |
| Os01g73170.1 | peroxidase precursor, putative, expressed | 2.45 | 0.041846292 | 10.9312 | 2.81781 |
| Os04g55720.1 | D-3-phosphoglycerate dehydrogenase, chloroplast precursor, putative, expressed | 2.44 | 0.024351298 | 25.7436 | 6.64834 |

TABLE 1-continued

| Gene model | Annotation | Fold change drought (B7-12/A36) | p-value | B7-12 (RPKM) | A36 (RPKM) |
|---|---|---|---|---|---|
| Os10g31330.1 | retrotransposon protein, putative, unclassified, expressed | 2.39 | 0.025256249 | 86.8535 | 22.9056 |
| Os02g07260.1 | phosphoglycerate kinase protein, putative, expressed | 2.37 | 0.026635993 | 53.5015 | 14.2099 |
| Os04g38870.4 | 14-3-3 protein, putative, expressed | 2.34 | 0.040467828 | 23.7275 | 6.38233 |
| Os08g33710.1 | ribonuclease T2 family domain containing protein, expressed | 2.34 | 0.035044134 | 33.4444 | 9.00889 |
| Os02g32520.2 | ERD1 protein, chloroplast precursor, putative, expressed | 2.33 | 0.03683252 | 14.9923 | 4.05293 |
| Os06g07760.1 | sulfiredoxin-1, putative, expressed | 2.33 | 0.046904416 | 29.9865 | 8.1148 |
| Os06g03800.1 | pollen ankyrin, putative, expressed | 2.32 | 0.045719504 | 12.2605 | 3.33104 |
| Os01g10890.1 | CAMK_KIN1/SNF1/Nim1_like.8 - CAMK includes calcium/calmodulin dep. protein kinases, expressed | 2.31 | 0.039219237 | 18.5848 | 5.07691 |
| Os05g47700.1 | LTPL152 - Protease inhibitor/seed storage/LTP family protein precursor, expressed | 2.30 | 0.042697449 | 52.4999 | 14.3715 |
| Os08g25720.1 | pyrophosphate-fructose 6-phosphate 1-phosphotransferase subunit alpha, putative, expressed | 2.30 | 0.048255047 | 8.9484 | 2.45378 |
| Os06g29180.1 | erythronate-4-phosphate dehydrogenase domain containing protein, expressed | 2.30 | 0.033926849 | 44.5829 | 12.2327 |
| Os01g68300.1 | expressed protein | 2.22 | 0.035781973 | 1111.02 | 315.67 |
| Os02g52390.1 | M16 domain containing zinc peptidase, putative, expressed | 2.20 | 0.039703736 | 44.7604 | 12.8433 |
| Os07g05360.1 | photosystem II 10 kDa polypeptide, chloroplast precursor, putative, expressed | 2.18 | 0.045788927 | 59.2679 | 17.1484 |
| Os12g33120.1 | expressed protein | 2.17 | 0.045013224 | 237.343 | 68.9371 |
| Os01g37910.1 | vacuolar-processing enzyme precursor, putative, expressed | 2.15 | 0.04915593 | 48.0585 | 14.1222 |
| Os03g57220.2 | hydroxyacid oxidase 1, putative, expressed | −2.11 | 0.04973388 | 120.76 | 160.463 |
| Os08g44680.1 | photosystem I reaction center subunit II, chloroplast precursor, putative, expressed | −2.11 | 0.048774331 | 646.373 | 859.146 |
| Os09g00999.1 | expressed protein | −2.16 | 0.042040381 | 624.184 | 849.324 |
| Os07g09800.1 | expressed protein | −2.19 | 0.043369594 | 41.2813 | 57.066 |
| Os04g21350.1 | flowering promoting factor-like 1, putative, expressed | −2.22 | 0.039080205 | 81.6275 | 114.133 |
| Os08g01380.1 | 2Fe—2S iron-sulfur cluster binding domain containing protein, expressed | −2.23 | 0.036387607 | 104.838 | 147.563 |
| Os04g16872.1 | photosystem II D2 protein, putative, expressed | −2.29 | 0.039753954 | 14.3788 | 20.7646 |
| Os03g18770.1 | wound-induced protein WI12, putative, expressed | −2.32 | 0.037385003 | 17.4302 | 25.5421 |
| Os08g01170.1 | acetyltransferase, GNAT family, putative, expressed | −2.34 | 0.047340648 | 9.44318 | 13.9644 |
| Os01g58049.1 | photosystem I assembly protein ycf4, putative, expressed | −2.36 | 0.038341618 | 15.4432 | 23.0173 |
| Os01g43980.1 | retrotransposon protein, putative, unclassified, expressed | −2.36 | 0.042151575 | 1.88686 | 2.81276 |
| Os12g35465.1 | expressed protein | −2.36 | 0.040741528 | 6.94725 | 10.3569 |
| Os06g15360.3 | RAD23 DNA repair protein, putative, expressed | −2.38 | 0.044872431 | 5.14721 | 7.72242 |
| Os12g02340.2 | LTPL14 - Protease inhibitor/seed storage/LTP family protein precursor, expressed | −2.38 | 0.049365188 | 12.9394 | 19.4327 |
| Os11g35710.1 | cycloartenol synthase, putative, expressed | −2.39 | 0.033210561 | 4.83313 | 7.29655 |
| Os02g32250.1 | retrotransposon protein, putative, unclassified, expressed | −2.40 | 0.029254255 | 5.09024 | 7.69633 |
| Os06g16330.1 | BRASSINOSTEROID INSENSITIVE 1-associated receptor kinase 1 precursor, putative, expressed | −2.41 | 0.037727183 | 3.61924 | 5.49781 |
| Os01g01120.1 | enolase-phosphatase E1, putative, expressed | −2.42 | 0.028980149 | 13.3159 | 20.327 |
| Os08g11470.1 | transposon protein, putative, CACTA, En/Spm sub-class, expressed | −2.42 | 0.040771816 | 2.54775 | 3.89277 |
| Os02g01590.2 | glycosyl hydrolases, putative, expressed | −2.42 | 0.038144132 | 3.89457 | 5.9538 |
| Os07g01480.2 | oxygen evolving enhancer protein 3 domain containing protein, expressed | −2.43 | 0.021063133 | 65.8037 | 100.78 |
| Os12g43380.1 | thaumatin, putative, expressed | −2.45 | 0.025703885 | 23.6051 | 36.423 |
| Os04g16722.1 | uncharacterized protein ycf68, putative, expressed | −2.45 | 0.018254508 | 9550.19 | 14744.2 |
| Os09g08910.1 | ATP synthase, putative, expressed | −2.46 | 0.024377738 | 5.18384 | 8.03774 |

TABLE 1-continued

| Gene model | Annotation | Fold change drought (B7-12/A36) | p-value | B7-12 (RPKM) | A36 (RPKM) |
|---|---|---|---|---|---|
| Os06g01210.1 | plastocyanin, chloroplast precursor, putative, expressed | −2.47 | 0.017359677 | 505.916 | 788.873 |
| Os04g40630.3 | BTBZ4 - Bric-a-Brac, Tramtrack, Broad Complex BTB domain with TAZ zinc finger and Calmodulin-binding domains, expressed | −2.48 | 0.040222601 | 3.98385 | 6.23537 |
| Os08g23410.1 | rubredoxin family protein, putative, expressed | −2.49 | 0.021188627 | 22.0919 | 34.7154 |
| Os02g56940.2 | expressed protein | −2.50 | 0.048028799 | 4.29532 | 6.76306 |
| Os11g02424.2 | LTPL9 - Protease inhibitor/seed storage/LTP family protein precursor, expressed | −2.50 | 0.025681419 | 17.3126 | 27.3406 |
| Os01g09620.1 | zinc finger/CCCH transcription factor, putative, expressed | −2.51 | 0.026677194 | 6.04229 | 9.57034 |
| Os09g26420.4 | AP2 domain containing protein, expressed | −2.51 | 0.020683786 | 13.4701 | 21.3636 |
| Os04g40100.1 | BTBN11 - Bric-a-Brac, Tramtrack, Broad Complex BTB domain with non-phototropic hypocotyl 3 NPH3 domain, expressed | −2.52 | 0.028632449 | 3.80953 | 6.06242 |
| Os02g45750.1 | protein kinase domain containing protein, expressed | −2.53 | 0.045403651 | 2.33871 | 3.73764 |
| Os10g24004.1 | expressed protein | −2.54 | 0.02111726 | 27.7315 | 44.3977 |
| Os11g13890.5 | chlorophyll A-B binding protein, putative, expressed | −2.56 | 0.018394166 | 25.1011 | 40.4963 |
| Os03g28960.1 | DNA-directed RNA polymerase subunit, putative, expressed | −2.56 | 0.03528912 | 2.1012 | 3.39128 |
| Os03g54150.1 | expressed protein | −2.57 | 0.032852054 | 1.98813 | 3.21744 |
| Os06g39708.1 | photosystem II P680 chlorophyll A apoprotein, putative, expressed | −2.58 | 0.023484887 | 5.94125 | 9.65741 |
| Os03g17174.1 | PsbP, putative, expressed | −2.58 | 0.034992189 | 5.56692 | 9.05769 |
| Os04g33660.1 | bifunctional monodehydroascorbate reductase and carbonic anhydrasenectarin-3 precursor, putative, expressed | −2.62 | 0.037315729 | 3.86508 | 6.38636 |
| Os08g17390.1 | expressed protein | −2.63 | 0.024950826 | 3.38554 | 5.6187 |
| Os02g40240.1 | receptor kinase, putative, expressed | −2.63 | 0.03901775 | 1.04241 | 1.73003 |
| Os07g22650.1 | expressed protein | −2.63 | 0.031528124 | 4.61748 | 7.66277 |
| Os02g45520.1 | uncharacterized membrane protein, putative, expressed | −2.64 | 0.020549594 | 3.45497 | 5.74754 |
| Os01g01280.1 | expressed protein | −2.67 | 0.015628319 | 13.0445 | 21.9808 |
| Os04g33830.1 | membrane protein, putative, expressed | −2.68 | 0.010216745 | 211.314 | 356.58 |
| Os12g27370.1 | expressed protein | −2.71 | 0.041699717 | 1.6132 | 2.75822 |
| Os07g13969.1 | expressed protein | −2.71 | 0.0181913 | 10.7634 | 18.4216 |
| Os12g34054.1 | mitochondrial ribosomal protein S3, putative, expressed | −2.73 | 0.049477102 | 1.26015 | 2.1663 |
| Os07g35260.1 | TKL_IRAK_DUF26-lc.9 - DUF26 kinases have homology to DUF26 containing loci, expressed | −2.76 | 0.019314796 | 3.40647 | 5.92903 |
| Os08g15296.1 | photosystem II reaction center protein H, putative, expressed | −2.77 | 0.009029597 | 65.7876 | 114.745 |
| Os01g57968.1 | expressed protein | −2.77 | 0.007427768 | 1261.8 | 2207.7 |
| Os02g42810.1 | oxidoreductase, short chain dehydrogenase/reductase family domain containing protein, expressed | −2.78 | 0.013632634 | 8.61573 | 15.1268 |
| Os05g48630.1 | expressed protein | −2.79 | 0.007437456 | 246.127 | 432.689 |
| Os12g41560.1 | expressed protein | −2.80 | 0.02902244 | 3.1284 | 5.52978 |
| Os10g21310.1 | photosystem II P680 chlorophyll A apoprotein, putative, expressed | −2.80 | 0.015449955 | 4.52616 | 8.0044 |
| Os01g41710.1 | chlorophyll A-B binding protein, putative, expressed | −2.81 | 0.006905218 | 323.987 | 573.608 |
| Os08g06090.1 | zinc finger, C3HC4 type domain containing protein, expressed | −2.82 | 0.036649395 | 2.8734 | 5.11857 |
| Os03g52239.2 | homeobox domain containing protein, expressed | −2.85 | 0.020717277 | 3.22534 | 5.788 |
| Os02g24598.1 | chloroplast envelope membrane protein, putative, expressed | −2.85 | 0.007994176 | 36.1604 | 64.9277 |
| Os04g12080.1 | TKL_IRAK_DUF26-lc.7 - DUF26 kinases have homology to DUF26 containing loci, expressed | −2.85 | 0.041070403 | 1.31646 | 2.36718 |
| Os04g44924.1 | short-chain dehydrogenase/reductase, putative, expressed | −2.86 | 0.017612658 | 4.64346 | 8.3898 |
| Os02g01140.1 | GDSL-like lipase/acylhydrolase, putative, expressed | −2.87 | 0.01280911 | 6.24649 | 11.3211 |
| Os12g33946.1 | cytochrome c oxidase subunit 1, putative, expressed | −2.89 | 0.014298673 | 3.79342 | 6.92534 |

TABLE 1-continued

| Gene model | Annotation | Fold change drought (B7-12/A36) | p-value | B7-12 (RPKM) | A36 (RPKM) |
| --- | --- | --- | --- | --- | --- |
| Os10g21230.1 | ATP synthase C chain, putative, expressed | −2.91 | 0.044044755 | 4.26926 | 7.82835 |
| Os09g37710.1 | NIN, putative, expressed | −2.93 | 0.046112809 | 0.58783 | 1.08828 |
| Os05g11064.1 | expressed protein | −2.94 | 0.028587135 | 2.32589 | 4.31324 |
| Os09g17850.1 | acetyltransferase type B catalytic subunit, putative, expressed | −2.95 | 0.040313841 | 1.18819 | 2.21185 |
| Os06g40640.2 | fructose-bisphospate aldolase isozyme, putative, expressed | −2.97 | 0.005871929 | 18.5791 | 34.7809 |
| Os03g11250.1 | expressed protein | −2.97 | 0.037124169 | 1.90148 | 3.56756 |
| Os02g42310.2 | OsSCP8 - Putative Serine Carboxypeptidase homologue, expressed | −2.98 | 0.007515762 | 8.86358 | 16.6299 |
| Os07g12800.2 | expressed protein | −3.00 | 0.040948201 | 0.964209 | 1.82098 |
| Os12g19470.1 | ribulose bisphosphate carboxylase small chain, chloroplast precursor, putative, expressed | −3.00 | 0.006825462 | 9.71274 | 18.4053 |
| Os12g34108.1 | ATP synthase protein 9, mitochondrial, putative, expressed | −3.01 | 0.01931871 | 3.70372 | 7.04199 |
| Os12g16350.12 | enoyl-CoA hydratase/isomerase family protein, putative, expressed | −3.03 | 0.015357674 | 2.53417 | 4.84772 |
| Os01g57960.1 | retrotransposon protein, putative, unclassified, expressed | −3.05 | 0.003686299 | 113.058 | 217.275 |
| Os04g02920.1 | leucine-rich repeat family protein, putative, expressed | −3.05 | 0.040133619 | 0.894626 | 1.71945 |
| Os06g15730.1 | expressed protein | −3.06 | 0.01207292 | 2.04551 | 3.94106 |
| Os01g51410.2 | glycine dehydrogenase, putative, expressed | −3.06 | 0.004114518 | 12.9951 | 25.0591 |
| Os02g39570.6 | ACT domain containing protein, expressed | −3.09 | 0.041130025 | 1.10089 | 2.13905 |
| Os08g02070.1 | OsMADS26 - MADS-box family gene with MIKCc type-box, expressed | −3.09 | 0.008546826 | 6.93434 | 13.5106 |
| Os12g42250.1 | ZOS12-10 - C2H2 zinc finger protein, expressed | −3.11 | 0.043405939 | 1.68039 | 3.29125 |
| Os09g01000.1 | expressed protein | −3.13 | 0.002835193 | 28626.9 | 56678.2 |
| Os01g48950.1 | expressed protein | −3.14 | 0.009488916 | 9.21536 | 18.2327 |
| Os01g53330.1 | anthocyanidin 5,3-O-glucosyltransferase, putative, expressed | −3.15 | 0.03594689 | 0.977994 | 1.94335 |
| Os02g36210.1 | ent-kaurene synthase, chloroplast precursor, putative, expressed | −3.16 | 0.013488185 | 1.26204 | 2.51531 |
| Os11g41034.1 | expressed protein | −3.17 | 0.026471925 | 1.06521 | 2.13003 |
| Os02g24614.1 | DNA-directed RNA polymerase subunit beta, putative, expressed | −3.18 | 0.020292773 | 1.16077 | 2.32663 |
| Os06g43350.1 | cytochrome P450, putative, expressed | −3.19 | 0.021363349 | 1.41985 | 2.86078 |
| Os02g42330.2 | nitrilase, putative, expressed | −3.20 | 0.031210755 | 1.40234 | 2.82859 |
| Os03g04060.1 | CHIT16 - Chitinase family protein precursor, expressed | −3.20 | 0.004653141 | 11.2584 | 22.7463 |
| Os04g52479.3 | peptidase, trypsin-like serine and cysteine proteases, putative, expressed | −3.22 | 0.01634472 | 1.2232 | 2.48759 |
| Os05g26070.1 | cyclin, putative, expressed | −3.22 | 0.024496667 | 1.48547 | 3.01958 |
| Os11g13890.4 | chlorophyll A-B binding protein, putative, expressed | −3.23 | 0.002404666 | 108.795 | 221.402 |
| Os06g03580.1 | zinc RING finger protein, putative, expressed | −3.24 | 0.044828258 | 1.12059 | 2.29091 |
| Os01g45274.1 | carbonic anhydrase, chloroplast precursor, putative, expressed | −3.26 | 0.002517656 | 38.5148 | 79.1304 |
| Os03g12660.1 | cytochrome P450, putative, expressed | −3.32 | 0.013360285 | 1.53999 | 3.22067 |
| Os02g24100.1 | expressed protein | −3.32 | 0.044769085 | 1.86548 | 3.90163 |
| Os04g24300.1 | OsWAK35a - OsWAK short gene, expressed | −3.32 | 0.027020786 | 0.623301 | 1.30685 |
| Os10g21190.1 | expressed protein | −3.33 | 0.001711351 | 2445.89 | 5139.54 |
| Os11g06800.1 | retrotransposon protein, putative, unclassified, expressed | −3.39 | 0.049559639 | 1.39094 | 2.97058 |
| Os11g46810.1 | retrotransposon protein, putative, unclassified, expressed | −3.42 | 0.002118456 | 13.8543 | 29.8772 |
| Os01g57020.1 | expressed protein | −3.44 | 0.003842246 | 4.58919 | 9.94446 |
| Os01g48990.2 | uncharacterized kinase mug58, putative, expressed | −3.44 | 0.003696533 | 5.13813 | 11.1609 |
| Os12g34018.1 | ATP synthase protein YMF19, putative, expressed | −3.45 | 0.044235735 | 1.23426 | 2.68572 |
| Os01g44020.1 | expressed protein | −3.45 | 0.041502973 | 2.27925 | 4.96304 |
| Os10g37180.1 | glycine cleavage system H protein, putative, expressed | −3.46 | 0.001738309 | 32.6701 | 71.3354 |
| Os01g12710.2 | oxidoreductase, short chain dehydrogenase/reductase family domain containing protein, expressed | −3.47 | 0.008159118 | 1.98177 | 4.34252 |

TABLE 1-continued

| Gene model | Annotation | Fold change drought (B7-12/A36) | p-value | B7-12 (RPKM) | A36 (RPKM) |
|---|---|---|---|---|---|
| Os03g22200.2 | nodulin MtN3 family protein, putative, expressed | −3.48 | 0.049214892 | 1.06068 | 2.32982 |
| Os12g44030.1 | purple acid phosphatase precursor, putative, expressed | −3.49 | 0.011989244 | 1.94701 | 4.28544 |
| Os03g14040.2 | expressed protein | −3.50 | 0.028420934 | 1.76265 | 3.89431 |
| Os02g22100.3 | OsRhmbd6 - Putative Rhomboid homologue, expressed | −3.54 | 0.042450158 | 0.656258 | 1.47098 |
| Os12g24320.1 | ATPase 3, putative, expressed | −3.55 | 0.018458942 | 0.924916 | 2.06871 |
| Os05g45890.2 | tRNAHis guanylyltransferase family protein, expressed | −3.60 | 0.039618106 | 0.528332 | 1.20289 |
| Os10g21396.1 | NADPH-dependent oxidoreductase, putative, expressed | −3.60 | 0.008362727 | 2.31162 | 5.25042 |
| Os07g01480.1 | oxygen evolving enhancer protein 3 domain containing protein, expressed | −3.60 | 0.03269576 | 0.946308 | 2.14243 |
| Os10g42020.1 | RALFL29 - Rapid ALkalinization Factor RALF family protein precursor, expressed | −3.64 | 0.002649312 | 11.3037 | 25.9462 |
| Os07g05480.2 | photosystem I reaction center subunit, chloroplast precursor, putative, expressed | −3.66 | 0.003326406 | 8.08208 | 18.6791 |
| Os06g38450.1 | vignain precursor, putative, expressed | −3.66 | 0.002890345 | 4.15974 | 9.60965 |
| Os08g15322.1 | cytochrome b559 subunit alpha, putative, expressed | −3.66 | 0.008488865 | 2.77526 | 6.41236 |
| Os03g34310.2 | expressed protein | −3.67 | 0.038910641 | 0.830196 | 1.91576 |
| Os03g15460.1 | expressed protein | −3.68 | 0.019181151 | 1.94767 | 4.51519 |
| Os11g13890.6 | chlorophyll A-B binding protein, putative, expressed | −3.70 | 0.005435782 | 2.43461 | 5.68905 |
| Os01g69840.1 | expressed protein | −3.71 | 0.002170427 | 14.9403 | 34.9671 |
| Os07g48040.1 | peroxidase precursor, putative, expressed | −3.71 | 0.002173163 | 5.36435 | 12.5589 |
| Os11g40090.1 | A49-like RNA polymerase I associated factor family protein, expressed | −3.73 | 0.017651288 | 0.842065 | 1.98187 |
| Os12g34094.1 | NADH-ubiquinone oxidoreductase chain 4, putative, expressed | −3.75 | 0.028523155 | 0.860706 | 2.03713 |
| Os04g16820.1 | DNA-directed RNA polymerase subunit beta, putative, expressed | −3.77 | 0.009887744 | 0.555736 | 1.32178 |
| Os06g46434.1 | cytochrome c biogenesis protein ccsA, putative, expressed | −3.78 | 0.046199711 | 0.769943 | 1.83503 |
| Os04g10750.4 | inorganic phosphate transporter, putative, expressed | −3.80 | 0.007369382 | 1.16562 | 2.7978 |
| Os08g35740.2 | 12-oxophytodienoate reductase, putative, expressed | −3.80 | 0.006247429 | 1.87677 | 4.50112 |
| Os01g63990.5 | hydrolase, alpha/beta fold family protein, putative, expressed | −3.81 | 0.029529997 | 0.763068 | 1.82868 |
| Os03g45779.1 | expressed protein | −3.83 | 0.012357599 | 1.6604 | 4.01537 |
| Os06g41010.3 | zinc finger A20 and AN1 domain-containing stress-associated protein, putative, expressed | −3.86 | 0.019926181 | 1.28767 | 3.1428 |
| Os10g42040.1 | expressed protein | −3.88 | 0.030731625 | 2.21964 | 5.4372 |
| Os10g01080.1 | SOR/SNZ family protein, putative, expressed | −3.89 | 0.005069858 | 2.20006 | 5.39425 |
| Os06g40640.1 | fructose-bisphospate aldolase isozyme, putative, expressed | −3.91 | 0.001400842 | 4.08166 | 10.0541 |
| Os07g11110.1 | NAD dependent epimerase/dehydratase family protein, putative, expressed | −3.93 | 0.000675528 | 11.7843 | 29.1984 |
| Os02g45520.2 | uncharacterized membrane protein, putative, expressed | −3.94 | 0.00421714 | 1.15253 | 2.87185 |
| Os01g16920.1 | embryonic protein DC-8, putative, expressed | −3.98 | 0.006093606 | 2.35729 | 5.91148 |
| Os06g23870.2 | acyl-CoA dehydrogenase domain protein, putative, expressed | −3.98 | 0.001086021 | 12.4808 | 31.332 |
| Os08g31410.5 | sulfate transporter, putative, expressed | −3.98 | 0.018120375 | 0.481531 | 1.21264 |
| Os10g38940.1 | fatty acid hydroxylase, putative, expressed | −3.98 | 0.012011389 | 1.32302 | 3.32473 |
| Os01g45274.4 | carbonic anhydrase, chloroplast precursor, putative, expressed | −4.00 | 0.000390136 | 71.9813 | 181.803 |
| Os09g24200.1 | RAD23 DNA repair protein, putative, expressed | −4.06 | 0.011957671 | 0.943316 | 2.41856 |
| Os01g61880.2 | respiratory burst oxidase, putative, expressed | −4.11 | 0.001153124 | 2.15394 | 5.57829 |
| Os11g01240.1 | IBR domain containing protein, expressed | −4.11 | 0.021607225 | 0.542908 | 1.40751 |
| Os03g39610.2 | chlorophyll A-B binding protein, putative, expressed | −4.11 | 0.000332278 | 30.8309 | 79.9466 |
| Os01g13120.1 | aquaporin protein, putative, expressed | −4.12 | 0.026464665 | 0.811939 | 2.1104 |

TABLE 1-continued

| Gene model | Annotation | Fold change drought (B7-12/A36) | p-value | B7-12 (RPKM) | A36 (RPKM) |
|---|---|---|---|---|---|
| Os04g29550.1 | RIPER2 - Ripening-related family protein precursor, expressed | −4.12 | 0.007320102 | 2.32311 | 6.04122 |
| Os04g01780.1 | uncharacterized ACR, COG1399 family protein, expressed | −4.13 | 0.003012322 | 2.22556 | 5.79825 |
| Os05g37170.8 | transcription factor, putative, expressed | −4.14 | 0.0137674 | 0.798359 | 2.07846 |
| Os09g26210.1 | ZOS9-12 - C2H2 zinc finger protein, expressed | −4.16 | 0.017146048 | 1.47155 | 3.85929 |
| Os04g38600.1 | glyceraldehyde-3-phosphate dehydrogenase, putative, expressed | −4.23 | 0.002482698 | 1.73177 | 4.6172 |
| Os01g28500.1 | SCP-like extracellular protein, expressed | −4.25 | 0.006643665 | 2.32969 | 6.24835 |
| Os02g46380.2 | purine permease, putative, expressed | −4.33 | 0.033108641 | 0.449198 | 1.21927 |
| Os03g31026.2 | retrotransposon protein, putative, unclassified, expressed | −4.33 | 0.004295454 | 0.867985 | 2.37493 |
| Os12g33962.1 | uncharacterized tatC-like protein ymf16, putative, expressed | −4.34 | 0.048989573 | 0.531805 | 1.45633 |
| Os01g32460.1 | expressed protein | −4.39 | 0.03102075 | 0.964544 | 2.67056 |
| Os12g39620.5 | disease resistance protein, putative, expressed | −4.41 | 0.012012142 | 0.436545 | 1.21301 |
| Os01g25484.3 | ferredoxin--nitrite reductase, putative, expressed | −4.43 | 0.000827728 | 2.18109 | 6.1005 |
| Os04g16770.1 | photosynthetic reaction center protein, putative, expressed | −4.46 | 0.000193741 | 17.4533 | 49.0407 |
| Os06g40640.3 | fructose-bisphospate aldolase isozyme, putative, expressed | −4.46 | 0.000239742 | 9.6605 | 27.1746 |
| Os12g12580.2 | NADP-dependent oxidoreductase, putative, expressed | −4.46 | 0.008349851 | 1.02209 | 2.88737 |
| Os01g51570.1 | glycosyl hydrolases family 17, putative, expressed | −4.51 | 0.040226868 | 0.445291 | 1.26603 |
| Os08g01690.1 | retrotransposon protein, putative, unclassified, expressed | −4.52 | 0.007619224 | 0.811031 | 2.30538 |
| Os10g21418.1 | NADPH-dependent oxidoreductase, putative, expressed | −4.54 | 0.000351456 | 3.03207 | 8.68233 |
| Os01g62060.3 | plant-specific domain TIGR01589 family protein, expressed | −4.57 | 0.042980678 | 0.944953 | 2.72623 |
| Os04g40530.1 | methyltransferase domain containing protein, expressed | −4.60 | 0.001394639 | 2.6646 | 7.7336 |
| Os08g01240.1 | expressed protein | −4.65 | 0.007485999 | 1.61447 | 4.73775 |
| Os01g64660.4 | fructose-1,6-bisphosphatase, putative, expressed | −4.79 | 0.007454393 | 0.760764 | 2.29732 |
| Os08g35420.1 | photosynthetic reaction center protein, putative, expressed | −4.81 | 7.82E−05 | 27.3698 | 83.0373 |
| Os02g01380.1 | expressed protein | −4.85 | 0.005170394 | 0.670185 | 2.05088 |
| Os10g42030.1 | expressed protein | −4.87 | 0.01204109 | 0.834753 | 2.56518 |
| Os12g38170.1 | osmotin, putative, expressed | −4.88 | 5.60E−05 | 80.4968 | 247.673 |
| Os10g04730.1 | TKL_IRAK_DUF26-la.6 - DUF26 kinases have homology to DUF26 containing loci, expressed | −4.96 | 0.000585907 | 1.3146 | 4.1092 |
| Os04g52260.1 | LTPL124 - Protease inhibitor/seed storage/LTP family protein precursor, expressed | −4.96 | 0.001867307 | 2.12163 | 6.63514 |
| Os02g57180.2 | NADH dehydrogenase 1 alpha subcomplex subunit 9,mitochondrial precursor, putative, expressed | −5.12 | 0.006046562 | 0.649766 | 2.10466 |
| Os04g58050.1 | expressed protein | −5.13 | 0.002431313 | 1.06758 | 3.45488 |
| Os01g03310.1 | BBTI1 - Bowman-Birk type bran trypsin inhibitor precursor, expressed | −5.14 | 5.53E−05 | 19.5107 | 63.2453 |
| Os07g40690.1 | NAD dependent epimerase/dehydratase family protein, putative, expressed | −5.18 | 0.009711085 | 0.587754 | 1.92089 |
| Os01g55570.4 | expressed protein | −5.20 | 0.002342732 | 1.82155 | 5.97436 |
| Os06g21980.2 | pantothenate kinase 4, putative, expressed | −5.23 | 0.044238551 | 0.307777 | 1.00544 |
| Os01g55974.3 | deoxycytidylate deaminase, putative, expressed | −5.29 | 0.014567188 | 0.470402 | 1.57056 |
| Os05g10310.1 | acid phosphatase, putative, expressed | −5.37 | 0.016168211 | 0.382125 | 1.29311 |
| Os01g74160.1 | carboxyl-terminal peptidase, putative, expressed | −5.37 | 0.000165502 | 3.05855 | 10.3628 |
| Os02g14170.2 | peroxidase precursor, putative, expressed | −5.38 | 0.006864916 | 0.652723 | 2.21656 |
| Os11g05190.1 | phytosulfokines precursor, putative, expressed | −5.48 | 0.01678246 | 0.678707 | 2.34629 |
| Os10g41999.1 | RALFL27 - Rapid ALkalinization Factor RALF family protein precursor, expressed | −5.52 | 0.040682104 | 0.495348 | 1.72315 |

TABLE 1-continued

| Gene model | Annotation | Fold change drought (B7-12/A36) | p-value | B7-12 (RPKM) | A36 (RPKM) |
|---|---|---|---|---|---|
| Os06g39120.1 | expressed protein | −5.53 | 0.000226805 | 3.33059 | 11.6259 |
| Os12g39620.4 | disease resistance protein, putative, expressed | −5.55 | 0.003196162 | 0.39917 | 1.40199 |
| Os12g24050.1 | retrotransposon protein, putative, unclassified, expressed | −5.56 | 0.000491875 | 0.388465 | 1.36269 |
| Os07g13770.1 | UDP-glucoronosyl and UDP-glucosyl transferase domain containing protein, expressed | −5.73 | 0.002184869 | 0.618458 | 2.23392 |
| Os02g24642.1 | photosystem II reaction center protein K precursor, putative, expressed | −5.76 | 0.020955552 | 0.944201 | 3.43118 |
| Os03g14669.2 | core histone H2A/H2B/H3/H4, putative, expressed | −5.81 | 2.24E−05 | 5.57868 | 20.4331 |
| Os11g13890.2 | chlorophyll A-B binding protein, putative, expressed | −6.10 | 0.016302812 | 0.309686 | 1.19768 |
| Os01g42210.1 | LTPL47 - Protease inhibitor/seed storage/LTP family protein precursor, putative, expressed | −6.14 | 0.016649766 | 0.564518 | 2.18593 |
| Os02g42310.4 | OsSCP8 - Putative Serine Carboxypeptidase homologue, expressed | −6.16 | 0.007460782 | 0.402748 | 1.56816 |
| Os07g03750.1 | SCP-like extracellular protein, expressed | −6.26 | 0.021306065 | 0.629922 | 2.48532 |
| Os09g16950.1 | cysteine-rich receptor-like protein kinase 25 precursor, putative, expressed | −6.47 | 0.001787905 | 0.393259 | 1.60501 |
| Os06g06980.3 | caffeoyl-CoA O-methyltransferase, putative, expressed | −6.62 | 0.000382154 | 1.29041 | 5.38687 |
| Os01g65090.2 | aminotransferase, classes I and II, domain containing protein, expressed | −7.08 | 0.006093234 | 0.291077 | 1.31301 |
| Os01g03320.1 | BBTI2 - Bowman-Birk type bran trypsin inhibitor precursor, expressed | −7.11 | 2.37E−05 | 3.12949 | 14.0342 |
| Os02g51770.2 | TLD family protein, putative, expressed | −7.13 | 0.002653059 | 0.434182 | 1.96715 |
| Os04g31804.1 | OsMADS64 - MADS-box family gene with M-alpha type-box, expressed | −7.26 | 0.00051423 | 0.810366 | 3.70925 |
| Os04g32240.1 | retrotransposon, putative, centromere-specific, expressed | −7.68 | 0.018735285 | 0.231279 | 1.12061 |
| Os10g40210.1 | retrotransposon protein, putative, Ty3-gypsy subclass | −7.80 | 0.035737399 | 0.342591 | 1.68629 |
| Os03g14334.1 | expressed protein | −7.94 | 0.015788103 | 0.239218 | 1.21521 |
| Os02g47744.3 | MYB family transcription factor, putative, expressed | −8.32 | 0.002155136 | 0.206919 | 1.09648 |
| Os02g21530.1 | expressed protein | −9.07 | 0.020448368 | 0.268415 | 1.53588 |
| Os10g42020.2 | RALFL29 - Rapid ALkalinization Factor RALF family protein precursor, expressed | −9.24 | 0.021519728 | 0.381216 | 2.18003 |
| Os11g26010.1 | retrotransposon protein, putative, unclassified, expressed | −9.89 | 0.000658558 | 0.218587 | 1.36391 |
| Os07g36080.3 | oxygen evolving enhancer protein 3 domain containing protein, expressed | −10.04 | 1.73E−07 | 5.56036 | 35.2314 |
| Os03g13976.1 | expressed protein | −10.81 | 0.029242121 | 0.197642 | 1.38591 |
| Os01g47200.1 | retrotransposon protein, putative, unclassified, expressed | −12.25 | 5.76E−05 | 0.290781 | 2.2469 |
| Os08g09240.2 | autophagy-related protein, putative, expressed | −12.93 | 0.016103366 | 0.1591 | 1.3233 |
| Os06g25010.1 | glycosyl hydrolase, putative, expressed | −13.59 | 0.007430365 | 0.122906 | 1.05329 |
| Os01g01307.2 | translocon-associated protein beta domain containing protein, expressed | −14.63 | 0.000460409 | 0.294688 | 2.771 |
| Os01g02790.1 | protein kinase domain containing protein, expressed | −18.02 | 0.000612146 | 0.089325 | 1.01503 |
| Os01g45914.1 | expressed protein | −23.65 | 1.07E−12 | 8.78029 | 130.938 |
| Os03g51530.1 | expressed protein | −27.22 | 0.000248169 | 0.162814 | 2.79487 |
| Os07g04930.1 | retrotransposon protein, putative, unclassified, expressed | −27.51 | 0.000226137 | 0.103328 | 1.79281 |
| Os03g26210.3 | helix-loop-helix DNA-binding domain containing protein, expressed | −28.64 | 0.001162253 | 0.0557487 | 1.03806 |
| Os02g06215.1 | RNA-directed DNA polymerase, putative, expressed | −33.24 | 3.25E−06 | 0.0862936 | 1.80899 |
| Os03g02670.3 | transporter family protein, putative, expressed | −42.44 | 0.000115651 | 0.0417516 | 1.17481 |
| Os12g04870.1 | expressed protein | −43.17 | 9.89E−05 | 0.0913211 | 2.48629 |
| Os01g52240.1 | chlorophyll A-B binding protein, putative, expressed | −50.81 | 9.01E−12 | 0.255551 | 8.18971 |
| Os07g06834.1 | expressed protein | −72.95 | 1.14E−17 | 0.722018 | 33.2201 |
| Os12g02210.1 | RING finger protein, putative, expressed | −110.89 | 3.36E−12 | 0.130078 | 9.09714 |
| Os08g14195.1 | expressed protein | −154.67 | 5.22E−17 | 0.0767163 | 7.48325 |

TABLE 1-continued

| Gene model | Annotation | Fold change drought (B7-12/A36) | p-value | B7-12 (RPKM) | A36 (RPKM) |
|---|---|---|---|---|---|
| Os07g15460.2 | metal transporter Nramp6, putative, expressed | −185.36 | 8.47E−10 | 0.0156898 | 1.63297 |
| Os08g28010.1 | expressed protein | −224.48 | 1.76E−14 | 0.0183586 | 2.5991 |
| Os03g18779.1 | expressed protein | −334.14 | 1.98E−14 | 0.0244952 | 5.1619 |
| Os07g26100.1 | expressed protein | −427.31 | 4.85E−09 | 0.00865809 | 2.33326 |
| Os08g29980.1 | retrotransposon protein, putative, unclassified, expressed | −818.52 | 1.24E−22 | 0.0052153 | 2.69221 |
| Os11g35300.1 | expressed protein | −1027.30 | 6.27E−16 | 0.0092041 | 5.96317 |

ABA levels increase when plants sense drought, and ABA-dependent signaling plays a predominant role in the plant response to water deficit (Nambara and Marion-Poll, Annu, Rev. Plant Biol. 56:165-185, 2005; Zhu, Annu, Rev. Plant Biol. 53:247-273, 2002). ABA contents were compared between A36 and B7-12 seedlings after drought treatment. Two-week-old seedlings were air-dried for 0, 1, 3 or 4 hours in a growth chamber (23° C.). Fully-expanded leaves (~100 mg FW) were harvested from the treated seedlings and immediately frozen in liquid nitrogen. After lyophilization, the dried materials were weighed and then ground in liquid nitrogen. ABA extraction was performed in darkness for 16 hours at 4° C. with extraction buffer (80% methanol, 100 mg/L butylated hydroxytoluene and 500 mg/L citric acid monohydrate). Quantification of ABA was carried out using a Phytodetek ABA ELISA kit (Agdia Inc., Elkhart, Ind.) following the manufacturer's instructions. No significant difference was observed despite dramatically elevated levels of ABA observed in the treated seedlings of both genotypes (FIG. 6E). The results suggest that the heightened expression of drought/ABA-responsive genes described above is likely due to an increased ABA sensitivity in Xa21 plants.

Since the infection of rice by any Xoo strains causes water stress, activation of Xa21 by drought raised the possibility of some degree of non-race-specific defense against this bacterial pathogen. Plants were inoculated with Xoo strains at the seedling or adult stages using the leaf-clipping method (Kauffman, et al., Plant Disease Rep. 57:537-541, 1973). For the adult inoculation, plants were grown in the greenhouse for 6 weeks, transferred to a controlled facility and clipped with scissors dipped in the Xoo inoculum. Seedling inoculation was performed at the 2-week-old stage. After inoculation, seedlings were cultured in water in growth chambers (27° C., under florescent light with light/dark photoperiod of 16/8) for the indicated time period. For hormone and water stress treatment assays, inoculated seedlings were grown in water supplemented with ABA and PEG, respectively. Disease lesion development and bacterial population were determined as described previously (Xu, et al., Plant J. 45:740-751, 2006).

Strain DY87031 possesses mutations in the sulfenylation system required by Xoo to trigger Xa21-mediated resistance (Burdman, et al., *Mol. Plant Microbe Interact.* 17:602-612, 2004) and induced similar lesion developments between A36 and B7-12 plants. Water stress was further enhanced by incubating challenged seedlings with polyethylene glycol (PEG), a nonionic water-soluble polymer widely used to simulate drought in plants (Lagerwerff, et al., *Science* 133: 1486-1487, 1961). Beginning at 5 days post-inoculation (dpi), B7-12 seedlings repeatedly showed a reduction in disease progression relative to A36 (FIG. 7A for the data at 7 dpi). Growth of Xoo in B7-12 was also at lower levels than that seen in A36 (FIG. 7B). However, at 10 dpi, lesion had spread to the entire length of infected B7-12 leaves. Therefore, cumulative drought stress does elicit an Xa21-dependent defense response capable of providing partial protection against Xoo. Notably, this defense mechanism might help explain the puzzling phenomenon that, under high temperatures in greenhouses (presumably elevating the water stress of infected leaves), adult IRBB21 plants (containing Xa21) exhibited shorter lesions than IR24 controls after challenge with compatible Xoo strains of different origins (Gu, et al., *Theor. Appl. Genet.* 108:800-807, 2003).

The interplay between drought and Xa21 resistance in the context of incompatible interactions was also examined. Treatment of B7-12 seedlings with PEG suppressed Xa21 resistance to incompatible PXO99A as evidenced by the reduction in lesion lengths and bacterial growth (FIG. 8A and FIG. 8B). Likewise, high temperatures appear to have a negative impact on Xa21 resistance at the adult stage (Gu, et al., *Theor. Appl. Genet.* 108:800-807, 2003). The apparent paradoxical effects of PEG/drought on Xa21 defense and resistance responses would suggest that distinct defense signaling pathways are initiated by Xa21 after Xoo infection (FIG. 9A-C).

Treatment of rice seedlings with PEG rapidly and significantly increases endogenous ABA accumulation (Ye, et al., *Plant Cell Physiol.* 52:689-698, 2011). The ability of ABA to suppress Xa21 resistance was tested by introduction of this hormone into the root zone. ABA can be taken up by roots from soil or cultural medium and transported via xylem to leaf blades (Schraut, et al., *J. Exp. Bot.* 55:1635-1641, 2004; Sauter, et al., *J. Exp. Bot.* 52:1991-1997, 2001). Application of ABA significantly compromised Xa21 resistance in a dosage dependent manner (FIG. 8C and FIG. 8D). The suppression effect can be attributed to the positive role of ABA in enhancing Xoo virulence (Xu, et al., *BMC Plant Biol.* 15:10, 2015; Xu, et al., *PLoS One* 8:e67413, 2013) and the potentially negative impacts of the hormone on XA21 signaling. Support for the later possibility comes from the well-established suppression effects of ABA on plant defense events (Mang, et al., *Plant Cell* 24:1271-1284, 2012).

Example 9—XB3 Functions as a Drought Regulator

The inventors previously showed that XB3 interacts with XA21 in planta (Wang, et al., 2006, supra). Interestingly, Xb3 transcripts were markedly induced by drought stress in wild-type cultivar TP309 (carrying no Xa21). Stress treatment of previously characterized RNA interference (RNAi) lines, A13 and 37-2 (Wang, et al., 2006, supra), revealed that down-regulation of Xb3 increased drought sensitivity (FIG. 7A). The inventors predicted that over-expression of Xb3 might enhance rice tolerance to drought. To test this, a 3×FLAG tagged Xb3 was placed in an expression cassette under the control of the maize ubiquitin promoter. More than 50 independent transgenic rice lines were generated, and found to represent a range of transgene expression based on RNA blot analysis. Six transgenic lines with moderate and high levels of Xb3 transcripts were randomly chosen for further characterization. Importantly, all plants were similar in size when grown under normal conditions. By contrast, drastically enhanced abilities to survive severe drought stress and to maintain water status were observed in Xb3 over-expression transgenic plants compared with the control lines A36 and TP309 (FIG. 7B). Notably, the extent of damage caused by the stress was inversely correlated with levels of Xb3 expression. These results indicate that accumulation of Xb3 transcript levels improves drought tolerance in rice.

Example 10—XB3 is Localized to Both the Plasma Membrane and the Nucleus

In this Example, a monopartite nuclear localization signal (NLS) was identified in XB3-C that is in addition to other previously reported domains (Wang, et al., 2006, supra). Based on this and the presence of the putative N-myristoylation site (a membrane targeting signal), the inventors predicted that XB3 is localized in both the plasma membrane and the nucleus. This hypothesis was tested by performing confocal microscopic analysis using rice protoplasts expressing fluorescently tagged XB3 fusion proteins under the control of a double cauliflower mosaic virus (CaMV) 35S promoter. To avoid disturbance of the putative membrane localization, enhanced green fluorescent protein (eGFP) was placed in-frame with XB3 between Thr10 and Gly11 (downstream of the N-myristoylation site). Transient co-expression of eGFP-XB3 with Discosoma sp. red fluorescent protein (DsRed)-nuclear localization signal fusion (DsRed-NLS) resulted in rice protoplasts with yellow nuclei. N-(3-Triethylammoniumpropyl)-4-(6-(4-(Diethylamino) Phenyl) Hexatrienyl) Pyridinium Dibromide (FM4-64) dye has been widely used to stain plasma membrane (red color) and visualize endocytosis (Vida and Emr, *J. Cell Biol.* 128:779-792, 1995). FM4-64 staining of rice protoplasts expressing eGFP-XB3 confirmed the plasma membrane localization of the fusion protein. To demonstrate co-localization of XB3 and XA21, the fluorescent tags mCherry and eGFP were fused to the C-termini of these two proteins, respectively. Consistent with the observations made for eGFP-XB3, red XB3-mCherry signals were clearly seen in the plasma membrane and the nucleus. Green fluorescence was detected in the plasma membrane and an ER-like compartment as previously reported (Park, et al., *PLoS One* 5:e9262, 2010). Co-localization of XB3-mCherry and XA21-eGFP in the plasma membrane was evidenced by the yellow color that resulted from superimposed single color images of the two fluorescent proteins. By contrast, mutations of the predicted NLS and the putative N-myristoylation residue Gly-2 eliminated the fluorescent signals from the nucleus and the plasma membrane, respectively. As a control, GFP was present in both the cytoplasm and the nucleus.

To confirm the subcellular localizations of functional XB3 expressed by its native promoter in planta, the nuclear and membrane fractions were purified from leaf tissues of TP309 and the Myc-XA21 line 4021-3, respectively. 4021-3, rather than double-tagged B7-12, plants were selected for protein-related experiments because of the relatively easy detection of XA21 by anti-c-Myc in this line coupled with the successful development of a monoclonal antibody that recognizes the C-terminal kinase domain of XA21 in the later stage of this study. As expected, XB3 was detected in both the nuclei-enriched and nuclei-depleted fractions. Fractionations were validated by the nuclear marker histone H3 and the chloroplast protein ribulose-1,5-bisphosphate carboxylase/oxygenase (Rubisco, nuclei-depleted). XB3 was also found in the microsomal pool of 4021-3 plants, in which membrane-localized XA21, but not the cytoplasmic marker UGPase, was present. Purification of the microsomal fraction led to XA21 degradation as evidenced by the accumulation of XA21$^{ncp}$ observed previously (Xu, et al., 2006, supra). The presence of XB3 in the cytosolic fraction (S) might be due to a leak from the nuclei and a release from the XA21 complex through cleavage during purification. Taken together, these results indicate that XB3 is co-localized with XA21 to the plasma membrane and also accumulates in the nucleus.

Example 11—XA21 Mediates a Higher Steady-State Level of XB3

Because Xb3 is required for full accumulation of XA21 in rice (Wang, et al., 2006, supra), it was examined whether the opposite scenario also holds true. It was found that abundance is increased in the Myc-XA21 line 4021-3 relative to the empty-vector control line A36. Furthermore, epitope-tagged XB3-3×FLAG was co-expressed with Myc-XA21 in *N. benthamiana* using a well-established transient system mediated by *Agrobacterium* transformation (Huang, et al., 2013, supra). Consistently, XB3 accumulated to a markedly higher level when co-expressed with XA21 in the infiltrated leaves than when expressed with the empty vector.

Example 12—XA21 Increases the Nuclear Accumulation of XB3 in Rice

It was next determined whether XA21 regulates subcellular distributions of XB3. It was decided to focus on the nuclear abundance of XB3 because it is unlikely that nuclear trafficking of proteins is influenced by the process of protein purification. By contrast, XB3 in the membrane pool could be released by cleavage of XA21 during sample preparation (see above). In addition, a monoclonal antibody was developed, anti-XA21K, against the C-terminal intracellular domain of XA21. This antibody specifically recognized the 140 kDa Myc-XA21 in 4021-3 plants. It was determined that XB3 is readily detectable in the nuclear fraction prepared from two-week-old untreated seedlings of 4021-3 but not in that of A36 control. In the XA21 nuclear pool, the cleaved XA21$^{ccp}$ product of 37 kDa was also detected using anti-XA21K. XA21$^{ccp}$ did not react with anti-c-Myc. Thus, XA21 is cleaved constitutively to some extent in vivo at the seedling stage, coinciding with the accumulation of XB3 in the same subcellular compartment.

In response to water stress, a marked increase in XB3 protein levels followed by a decline was observed in the A36 control. By contrast, XB3 accumulation in the nucleus of Xa21 seedlings reached higher levels and was sustained at five hours post drought stress (hpd). These changes in protein abundance likely result from a redistribution of pre-existing XB3 since no apparent difference in Xb3 mRNA was observed between the two lines during the time period of stress treatment, and the induction of Xb3 transcripts by drought in seedlings occurred at seven hpd. XA21$^{ccp}$ was detectable after drought, but appeared to be decreased at five hpd.

Example 13—Drought Tolerance Mediated by XA21 is Associated with Nuclear Accumulation of XB3

Plants, unlike mammals, lack the advanced adaptive immunity required to eliminate most infectious pathogens. This results in significant burden of invaders remaining inside the host for an extended period of time or even a lifetime. An ability to cope with pathogen-induced stresses would therefore be beneficial for infected plants. In the case of rice BLB, cumulative growth of xylem-limited Xoo can induce water deficit in diseased leaves. However, injury is largely reduced in plants expressing the immune receptor XA21. The simplest interpretation of this phenomenon is the lower level of Xoo in the resistant plants than that in susceptible individuals. The present disclosure, however, reveals a novel function of XA21, namely drought tolerance. Without being bound by any one theory, the inventors believe that XA21 carries an integrated ability to suppress bacterial over-accumulation during early stage infection and then contributes to the control of drought effects. Both of these functions serve to limit water loss injury (FIG. 11).

The present disclosure demonstrates that XB3, an E3 ubiquitin ligase associating with XA21, also acts as a drought regulator. Unlike Xa21, which is natural only in the wild species *O. longistaminata* (Khush, et al., 1990, supra), Xb3 is a member of an evolutionarily conserved plant gene family (Huang, et al., 2013, supra). In addition to Xb3 another member, AdZFP1 from the drought-tolerant species *Artemisia desertorum* Spreng, has been shown to be water-stress-responsive and capable of enhancing drought tolerance when over-expressing in tobacco (Yang, et al., *J. Biosci.* 33:103-112, 2008). Thus, XB3 likely represents a regulator of a conserved plant drought signaling network and the immune receptor XA21 is linked to this network through binding to XB3. Furthermore, the present results show that these two proteins are co-localized in the membrane system and that the expression of Xa21 leads to a higher abundance of XB3. Therefore, XA21 appears to promote storage of XB3 under normal growth conditions, potentially enhancing the ability of rice plants to survive drought stress. Of note, increased XB3 was not only observed in the total protein extracts, but also in the nuclei-enriched fraction from 23° C. treated two-week-old seedlings that accumulate the cleaved $XA21^{ccp}$. Independent studies have confirmed the proteolytic cleavage of XA21 by an unidentified protease at a site (designated XA21CS-1) near the transmembrane domain (Park, et al., 2010, supra; Wang, et al., 2006, supra; Jiang, et al., *Plant J.* 73:814-823, 2013; Chen, et al., *Mol. Plant* 7:874-892, 2014; Xu, et al., 2006, supra; Park and Ronald, *Nat. Commun.* 3:920, 2012). In contrast to the observations made using adult plants (Park and Ronald, *Nat. Commun.* 3:920, 2012, supra), the present data indicate that XA21 is constitutively cleaved to some extent at the seedling stage, which provides an explanation for the XA21-dependent nuclear accumulation of XB3.

Without being bound to any one theory, there are a number of ways that drought conditions can be perceived by the receptor kinase XA21 in a pathogen ligand-independent manner. One possibility is that water stress induces the production of a rice protein/peptide that can be recognized by the LRR domain of XA21. Since there is no homologs of RaxX identified in the rice genome, this would imply that XA21 is capable of recognizing two distinct ligands for pathogen defense and drought response, respectively. It has been shown that the *Arabidopsis* damage-associated molecule AtPep1 binds to the LRR-receptor kinase AtPEPR1 and activates immune responses (Huffaker, et al., *Proc. Natl. Acad. Sci. USA* 103:10098-10103, 2006; Yamaguchi, et al., *Proc. Natl. Acad. Sci. USA* 103:10104-10109, 2006). An alternative scenario is that drought might induce proteolysis of XA21, which in turn leads to a release and translocation of XA21-associated drought regulators (e.g., XB3) into the nucleus. However, no significant increase in $XA21^{ccp}$ levels was observed in the nuclei-enriched pool after drought stress treatment. By contrast, the nuclear abundance of XB3 was markedly increased after drought in an XA21-dependent manner. The distinct kinetics of XB3 and $XA21^{ccp}$ accumulation might reflect a difference in their stabilities in drought environments. Alternatively, XB3 might be released by a second, drought-induced cleavage of XA21 that results in short-lived intermediates. It has been well-documented in the animal system that cell-surface receptors can be activated via complex proteolysis (Kopan and Ilagan, *Cell* 137:216-33, 2009; Rawson, *Biochim. Biophys. Acta* 1828: 2801-2807, 2013). Regardless of the explanation, drought-triggered, XA21-dependent accumulation of XB3 might allow the E3 ubiquitin ligase to exceed a threshold in the nucleus leading to the degradation of its substrate(s) (FIG. 11).

XA21-mediated drought tolerance and defense likely utilize different signaling mechanisms. In response to water stress, the present studies identified 17 DEGs between XA21 and control plants known to be drought-responsive. Of these, four were subjected to q-PCR analysis to validate drought induction and differential expression. They include three later embryogenesis abundant (LEAs) genes (OsLEA1, OsLEA3 and OsLEA33) and OsNAC10. LEAs encode hydrophilic proteins that potentially function in cellular protection during water deficit, whereas OsNAC10 codes for a transcription factor of the NAM ATAF CUC2 (NAC) family (Xiao, et al., *Theor. Appl. Genet.* 115:35-46, 2007; Jeong, et al., *Plant Physiol.* 153:185-197, 2010; Battaglia, et al., *Plant Physiol.* 148:6-24, 2008). Overexpression of either OsLEA3 or OsNAC10 in transgenic rice plants enhances drought tolerance. In contrast, no defense marker genes, including PR10b (Os12g36850), Os04g10010 and Os12g36830, previously shown to be induced by RaxX treatments in an XA21-dependent manner (Pruitt, et al., *Sci. Adv.* 1:e1500245, 2015), were detected as DEGs following drought. These results strongly suggest that in XA21 plants water stress triggers a heightened drought response signaling, but does not activate pathogen defense.

In conclusion, the immune sensor XA21 was surprisingly demonstrated to confer tolerance to drought. This novel function may act directly or indirectly through sensing water stress and subsequently activating of drought regulators (e.g., OsNAC10). Based on these results, an integrated ability for XA21 to suppress Xoo over-accumulation during early stage infection and then to control the water deficit caused by remaining bacteria may be achieved (FIG. 9A-C). These findings therefore unify biotic and abiotic signaling under the control of a single stress sensor, XA21.

Rice is the staple food of more than half of the population in the world. Demonstration of the drought tolerance function of XA21 allows development of rice varieties with a broad-spectrum resistance/tolerance to environmental stresses using a single gene/pathway.

Example 14. Methods

A. Plant Materials:

Rice (*Oryza sativa* L.) subspecies *japonica* cv. TaiPei309 (TP309), *O. sativa* ssp. *indica* IR24, and their derivatives were used in this study. Seeds with similar vigor were surface-sterilized with bleach and germinated on half-strength Murashige-Skoog (MS) medium supplemented with 30 g/L sucrose and 50 µg/ml hygromycin (for transgenic *japonica* lines only) for 9 days in a growth room with a 16 h photoperiod, a light intensity of 160-180 µm photons m$^{-2}$ sec$^{-1}$ and 23-25° C. Germinated seedlings were either grown in a greenhouse or cultured in water until stress treatments or Xoo inoculation as described below.

B. Rice Inoculation and Disease Evaluation:

Two-week-old seedlings (grown in medium) or 6-week-old plants (grown in soil) were inoculated with the Xoo strain PXO99$^4$ using the leaf-clipping method (Kauffman et al. "An improved technique for evaluating resistance of rice varieties to *Xanthomonas oryzae*." *Plant Dis. Rep.* 57, 537-541 (1973)). The seedlings were cultured for additional 12 days after inoculation for disease development in an incubator as above but at 27° C. Inoculated adult plants were maintained in a growth room as above between 26-30° C. Disease lesion and bacterial population were determined as described (Wang et al. 2006).

C. Plasmid Construction:

The 3×FLAG-XA21-Myc construct was made using an 9.9-kb genomic fragment, containing the c-Myc-tagged Xa21 coding region, intron (not shown) and the native 5' and 3' regulatory sequences, previously used for rice transformation (Wang et al. 2006). To delete the extra 3' sequence from the 9.9 kb Xa21-containing fragment, a KpnI-SpeI fragment with Myc-Xa21 was mobilized from the plasmid pBEK822-Bm into the vector pKBluescript to generate pKBXA21KS-M. An additional 1.8 kb 3' sequence, PCR amplified from the 9.9 kb Xa21 fragment with primers XA21-Tail-F/-R (5' CTTTCCGAAGACGAGTATATC-TAACG 3' (SEQ ID NO: 3)/5' ACTAGTGGTACCCGTCT-TATATCGCCTCA 3' (SEQ ID NO: 4)) was added to the 3' end of the KpnI-SpeI fragment of pBXA21KS-M using the SpeI site. The resultant construct, pKB-Myc-XA21-S, contains a c-Myc tag in the N-terminal region (domain B) of XA21. To introduce a c-Myc tag to the C-terminus of XA21, the EcoRI fragment of pKB-Myc-XA21-S was replaced by one with the tag fused to the C-terminus of XA21. The N-terminal c-Myc tag in the construct was replaced with 3×FLAG using the DraIII site. The 8.7-kb KpnI fragment containing Myc-Xa21-3×FLAG was verified by DNA sequencing and subcloned into the binary vector pCAM-BIA1300. *Agrobacterium*-mediated transformation was performed using rice cultivar TP309 as described (Wang et al. 2006).

D. Stress Treatments:

For dehydration assays, 11-day-old (for indica lines IRBB21 and IR24) or 2-week-old (for all *japonica* lines) seedlings were air-dried in a growth chamber (23° C.) for the indicated time periods followed by a recovery in liquid half-strength MS medium for three days. Survivors were defined as individuals possessing at least one true leaf flattened after recovery.

We determined RWC of dehydration-stressed leaves using the equation: RWC=(FW−DW)/(TW−DW), where FW is the fresh weight of the leaf discs collected. Turgid weight (TW) was measured after floating the leaf discs on water for 24 hour at room temperature in dark. Dry weight (DW) was determined by weighing the leaves after drying at 65° C. for three days.

For HgCl$_2$ treatments of detached rice leaves, 2-week-old seedlings of B7-12 and A36 lines were air-dried for the indicated times at 23° C. The second leaves of the stressed seedlings were excised under water and the cut side was immersed into artificial xylem sap (AXS: 1 mM KH$_2$PO$_4$, 1 mM K$_2$HPO$_4$, 1 mM CaCl$_2$, 0.1 mM MgSO$_4$, 3 mM KNO$_3$ and 0.1 mM, MnSO$_4$ buffered to pH 5.8 with 1 M HCl or KOH) or AXS containing 200 mM HgCl$_2$. AXS uptake was allowed for 1.5 h under light-emitting diode (LED) lights (1200 µm photons m$^{-2}$ sec$^{-1}$) at 23-25° C. in the growth room. As a control, leaves were also cut from well-watered seedlings subjected to the same treatments. Leaf damage was defined as the length of shrunken plant tissues from tips.

Dye uptake experiments using detached rice leaves were conducted the same as the HgCl$_2$ treatments except that 0.1% (w/v) safranin used instead of HgCl$_2$.

PEG stress assays were carried out as described (Verslues et al. "Methods and concepts in quantifying resistance to drought, salt and freezing, abiotic stresses that affect plant water status." *The Plant Journal* 45(4), 523-539 (2006)), with some modifications. Briefly, rice seeds with similar vigor were germinated on half-strength MS medium (containing no sucrose) supplemented with 50 µg/ml hygromycin for three days. Germinated seedlings were then transferred onto freshly prepared PEG-infused agar plates (containing no sucrose nor hygromycin, −0.7 MPa) or control medium (−0.25 MPa) for additional five days. Growth parameters were then scored.

To assess the growth performance of plants under mild to moderate water-deficit stress in soil, germinated seedlings were planted in containers of 21.5×15.5×9.5 cm (L×W×H) (three plants each genotype in one container) with pre-wetting soil. Plants were maintained in the growth room mentioned above. An MPS-6 water potential sensor (Decagon Devices) was embedded into soil to monitor the soil matric potential (SMP) every 60 min for the entire period of plant growth. Re-watering was carried out periodically to keep SMP between −700 to −900 kPa. Growth parameters were recoded one month after transplanting (FIG. 12).

E. RNA-Seq Analysis:

Leaf blades of dehydration-treated and the control seedlings (see Table 2) were harvested for RNA preparation. For moderate drought-treated and the control plants (Table 2), only the leaf blades at position 6 were collected. Total RNA was extracted using the TRIzol Reagent (Ambion) according to the manufacturer's instruction. After treatment with RNase-free DNase (Qiagen) to eliminate genomic DNA contamination followed by further purification using RNeasy MinElute Cleanup Kit (Qiagen), the purified RNA was submitted to Novogene for RNA-seq library construction and sequencing.

Fastq files containing Illumina reads were quality filtered (Phred score >20) and clipped for sequencing adapters using trim_galore software. Alignment was conducted with Tophat2 using the reference genome deposited at the Rice Genome Annotation Project. Alignment results were transformed to barn format and reads were de-duplicated with Samtools. Quantification of the number of reads per gene was performed using the FeatureCounts tool. Read quantification were conducted at the exon level. Differential Expression (DE) analysis was performed using DESeq2 (adjusted P-value ≤0.05). Comparison of DE genes for each condition, and construction of Venn Diagrams and plots were conducted with the R package.

GO terms enrichment was conducted using the Plant-GOSlim annotation obtained from the Rice Genome Annotation Project. The analysis was performed using the Network Gene Ontology tool, Bingo (hypergeometric test with Benjamini and Hochberg (FDR) correction, adjusted P-value ≤0.05). Hierarchical networks generated in Bingo were used to extract and select enriched GO terms.

F. Immunodetection:

Protein extraction and protein blot analysis were performed as described (Wang et al. 2006).

G. Quantification of Lignin:

Lignin content of rice leaves was quantified according to the thioglycolic acid method described previously (Suzuki et al. "High-throughput determination of thioglycolic acid lignin from rice." *Plant Biotech.* 26(3), 337-340 (2009)). In brief, leaf tissues were harvested from 2-week-old seedlings. The prepared cell wall samples were dried, weighted and mixed with a reaction mixture containing 0.1 ml of thioglycolic acid (Sigma) and 1 ml of 3 N HCl. The samples were then incubated at 80° C. for 3 h. After centrifugation, the pellet was collected, washed once with distilled water and dissolved in 1 ml of 1 N NaOH. Following acidification with 0.2 ml of concentrated HCl for 4 h at 4° C., the samples were dissolved in 1 ml of 1 N NaOH. Diluted samples were subjected to spectrophotometric measurements.

H. Quantification of Cellulose:

Cellulose content of rice leaves was measured as described (Kumar and Turner "Protocol: a medium-throughput method for determination of cellulose content from single stem pieces of *Arabidopsis thaliana.*" *Plant methods,* 11(1), 46 (2015)). Briefly, leaf tissues were harvested from 2-week-old seedlings and the alcohol insoluble residue (AIR) was prepared, weighed and extracted with acetic/nitric reagent. The samples were then hydrolyzed with 67% sulfuric acid and the released glucose was quantified with anthrone reagent.

I. Histological Analysis:

For calcofluor white staining, leaf blades were fixed in Dietrich's Formalin Acetic Acid (FAA) overnight at 4° C. Fixed samples were processed with the aid of a Pelco BioWave Pro laboratory microwave. Samples were dehydrated in a graded ethanol series, 75%, 85%, 95%, 100%, followed by 100% anhydrous acetone. Dehydrated samples were infiltrated in LRWhite Hard resin 50% then 100% and cured at 100° C. for 24 h. Semi-thick sections (500 nm) were stained with Calcofluor-white (Sigma) for one minute followed by mounting sections to slides with Depex mounting medium and viewed under UV using an Olympus BX 51 upright fluorescence microscope.

For lignin staining, hand-cut specimens prepared from leaf blades were incubated in 2% (w/v) phloroglucinol-HCl for 5 min and viewed using an Olympus BX 51 upright fluorescence microscope Example 15. Xa21 Increases Plant Survival after Dehydration Stress The ability of Xa21 to confer dehydration survival was tested. Newly generated homozygous Xa21 lines (B7-12 and B7-11), expressed 3×FLAG-XA21-Myc under the control of the native Xa21 promoter. Air-drying of 2-week-old seedlings for 3.5 hours (h) at 23° C. caused ≥54% mortality in A36 plants, but ≤25% death in B7-12, B7-11 and 4021-3 plants expressing a heterologous Xa21 gene (FIGS. 13A-B). The introgression line IRBB21 also exhibited better performance under dehydration relative to the near-isogenic recurrent parent *O. sativa* ssp. *indica* cv. IR24 (FIG. 13B). Under well-watered conditions, the relative leaf water content (RWC) of the two genotypes were similar. However, the RWC was sharply reduced by dehydration in both the B7-12 and A36 lines, with a statistically larger decrease in the control seedlings (FIG. 13C). These results indicated that heterologous expression of Xa21 increase survival of rice during dehydration stress.

Example. 16. Dehydration Stress Induces Xa21-Dependent Up-Regulation of Cellular Protective Genes RNA-sequencing (RNA-seq) analysis using leaf tissues of B7-12 and A36 seedlings harvested at 0 and 3 h post air-drying (hpa) is shown in Table 2). 3.0 hpa was chosen for RNA-seq analysis to ensure that the identified transcriptomic alterations potentially contribute to the phenotypic differences at 3.5 hpa. Among the differentially expressed genes (DEGs) (adjusted P<0.05) at 3 hpa were numerous up-regulated genes associated with drought tolerance in Xa21 seedlings (B7-12) even though the RWC in this line was higher compared to that of A36. These genes included 18 out of the 34 predicted rice OsLEAs (known for their protective functions of membrane and proteins from dehydration/desiccation damage), three of the six rice OsELIPs (photoprotective), a variety of genes encoding antioxidant and detoxication enzymes (e.g., ascorbate peroxidases (APX), superoxide dismutases (SOD), peroxiredoxin and glutathione S-transferases (GSTs)) and the genes coding for sugar (raffinose family oligosaccharides, sucrose and octulose) metabolic enzymes (FIG. 14A-D and Table 3). Compared to the transcript levels at 0 hpa, many of the DEGs (e.g., OsLEAs) were induced by the stress in the two genotypes, but to a lower magnitude in A36 (Table 3). Interestingly, OsELIP1, 5 and 6 were specifically induced by dehydration stress in Xa21 seedlings (B7-12) (FIGS. 14C-D). These findings indicated that Xa21 expression activates a cellular protective machinery probably distinct from the general dehydration-responsive mechanism in rice leaves under extreme drought conditions. One or more of the genes identified above as being up-regulated by Xa21 are known to be expressed in drought conditions.

Example 17. Plants Expressing Heterologous Xa21 Accumulate Higher Levels of Cellulose and Lignin in Leaf Vascular Tissues Transcripts up-regulated in Xa21 seedlings (B7-12) relative to A36 at 3 hpa included seven OsCESAs genes encoding cellulose synthases (Table 4). OsCESA4, 7 and 9 are individually required for secondary cell-wall formation. OsCESA1, 3 and 8 may participate in primary wall synthesis. Prior to air-drying, transcript levels of most of these genes (except for OsCESA6) seemed to be slightly higher in B7-12 seedlings than in A36 control. The difference became statistically significant due to greater suppression of their expression in A36 during dehydration stress. In 2-week-old seedlings, biochemical quantification showed that B7-12 leaves accumulated higher levels of cellulose compared to A36 (FIG. 15A, at the 0 time point) and that these levels were maintained during 24 h of drought stress. The increased cellulose deposition occurred mainly in cell walls of the vascular tissues (FIG. 15B). These results indicated that Xa21 expression enhances cellulose accumulation.

Among the up-regulated transcripts in Xa21 seedlings (B7-12) at 3 hpa were OsSWN1, but not its cognate gene OsSWN2, and three OsMYBs (OsMYB55/61, and OsMYB58/63 and OsMYB58/63-L) which all, including OsSWN2, encode key transcription regulators controlling secondary cell-wall formation and lignin content in rice (Table 4). Accordingly, Xa21 seedlings expressed higher levels of 44 out of the 46 DEGs potentially involved in lignin biosynthesis at 3 hpa (Table 4). Similar to most of the Xa21-influenced OsCESAs, transcript levels of many of the genes related to lignin synthesis appeared to be higher in Xa21 seedlings (B7-12) compared to A36 control prior to stress treatments (FIG. 15C, FIG. 16). Three of the five lignin synthetic genes (Os4CL3, Snl6 and OsCAD2) were induced by dehydration in both B7-12 and A36, but to a higher magnitude in Xa21 seedlings. The expression of OsFNSII, which is involved in the biosynthesis of tricin, was reduced by stress. Consistent with the expression data, higher lignin content was detected before dehydration in B7-12 than in the control (A36) (FIG. 15D). Lignin levels in Xa21 leaves were further increased after the stress. Lignin accumulated mainly in sclerenchyma and the parenchyma cells adjacent to the xylem vessels of B7-12 seedlings (FIG. 16). Enhanced cellulose and lignin deposition in the xylem of Xa21 seedlings may improve mechanical support of the conduits. Higher content of hydrophobic lignin may also reduce water leakage from the xylem vessels and formation of gas emboli induced by dehydration stress.

Example 18. Heterologous Expression of Xa21 Aids in the Restoration of Xylem Function after Dehydration Stress Refilling of embolized vessels during drought requires water supply from the surrounding cells. AQPs are considered the key channels of this water transport. 10 out of the 34 rice AQPs were identified as DEGs at 3 hpa, with the transcripts of 9 being higher in B7-12 seedlings than in A36 (FIG. 17A). The up-regulated transcript included three AQPs coding for plasma membrane intrinsic proteins (PIPs), five for tonoplast intrinsic proteins (TIPs) and one for a nodulin 26-like intrinsic protein (NIP). Among the PIPs, OsPIP1; 3 (also known as RWC3) and OsPIP2; 3 (OsPIP2-2) have been implicated in improving stress tolerance and water status. Prior to stress, transcript levels of these AQPs appeared to be slightly lower in B7-12 than in A36 (FIG. 17B). To test whether AQP function is essential for Xa21-mediated dehydration survival, we treated rice leaves with mercuric chloride, a widely used inhibitor of AQPs, using a previously established detached leaf assay (Stiller et al. "Embolized conduits of rice (*Oryza sativa*, Poaceae) refill despite negative xylem pressure." *Am. J. Bot.* 92(12), 1970-1974 (2005) and Shatil-Cohen et al. "Bundle-sheath cell regulation of xylem-mesophyll water transport via aquaporins under drought stress: a target of xylem-borne ABA?" *The Plant Journal* 67(1), 72-80 (2011)). Leaves were excised from seedlings pre-hydrated for 3.5 h and then their cut-ends were immersed into artificial xylem sap (AXS). Those from B7-12, but not A36, uncurled in the absence of mercuric chloride (FIG. 17C). The recovery of the B7-12 leaves occurred within 5-10 min, suggesting that the water transport ability in the Xa21 line may not be disrupted by dehydration-induced embolisms, thereby allowing quick delivery of water to the mesophyll cells in the recovery phase. By contrast, the feeding of mercuric chloride into the transpiration stream from the cut-ends largely blocked the recovery of the pre-hydrated B7-12 leaves (FIG. 17C). Increased recovery was observed when the two genotypes were stressed for a shorter time period (i.e., 2.5 h), and B7-12 leaves maintained a better performance compared to A36. Thus, AQP accumulation during dehydration is likely required for Xa21 leaves to survive a longer time period of severe water stress.

Safranin uptake assays were used to assess the role of Xa21 in xylem refilling after dehydration treatments. The dye moves in the transpiration stream to stain the xylem elements, and serves as a tool to trace water transport in the conduits. Safranin was readily visible in whole veins of the leaves excised from unstressed A36 and B7-12 seedlings 1.5 h after dye perfusion. A36 leaves dehydrated for 2.5 or 3.5 h, however, showed very limited dye staining, indicative of irreversible impairment of xylem function induced by dehydration stress in the control line. Accordingly, large areas on the distal half of the stressed leaves were unable to recover from the stress. By contrast, safranin stained most of each B7-12 leaf subjected to the same duration of dehydration stress, despite a reduction in the density of stained vessels compared with leaves from unstressed seedlings. These findings, in combination with the quick recovery of B7-12 leaves described above, suggested heterologous Xa21 expression improves to maintenance of the xylem during dehydration, consequently facilitating the restoration of water transport in the recovery phase.

Example 19. Heterologous Expression of Xa21 Enhances Rice Growth Under Moderate Drought The effect of heterologous expression of Xa21 plant growth under mild to moderate drought was examined. As expected, the growth of A36 seedlings was reduced by about 40% when transferred from half strength MS medium to a low-water potential (low-$\psi_w$), PEG-infused medium (−0.7 MPa) (FIG. 18A). B7-12 seedlings displayed significantly better growth, as measured by the fresh and dry weights of both shoots and roots, under the same low-$\psi_w$ conditions (FIG. 18A-E). Soil drying experiments showed that under moderate levels of drought stress, imposed by keeping the final soil matric potential (SMP) between −700 to −900 kPa, Xa21 plants (B7-12) showed a growth advantage, as judged by fresh and dry weight, over the control line one month after stress treatments (FIG. 18F-H). B7-12 had longer leaves than A36, starting with the fourth leaf (Supplementary FIG. 18B). No significant difference in growth was observed when both B7-12 and A36 were grown under well-watered conditions.

Example 20. Moderate Water-Deficit Induces Xa21-Dependent Up-Regulation of Transcription Regulators Involved in Growth-Promoting and Stress Responsive Networks RNA-seq analysis using the expanded leaf 6 of both genotypes revealed that water stress led to significantly higher transcript levels of eight OsJAZ [Jasmonate (JA) ZIM-domain]/OsTIFY genes, namely OsJAZ1, 4, 6, 7, 9, 10, 11, 12, in an Xa21-dependent manner (Table 5). JAZs are key repressors of JA-responsive genes and belong to the plant-specific TIFY protein family (Browse "Jasmonate passes muster: a receptor and targets for the defense hormone." *Annu. Rev. Plant Biol.* 60, 183-205 (2009) and Ye et al. "Identification and expression profiling analysis of TIFY family genes involved in stress and phytohormone responses in rice." *Plant. Mol. Biol.* 71(3), 291-305 (2009).). Hakata et al. ("Overexpression of TIFY genes promotes plant growth in rice through jasmonate signaling." *Biosci Biotechnol Biochem.* 81(5), 906-913 (2017)) reported that over-expression of OsJAZ1, 6, 7, 9, 10, 11, or 12 alone can improve rice growth. Drought stress also triggered the accumulation of transcripts encoding the APETALA2 (AP2) transcription factors OsDREB1A, B, C, E and H in B7-12 plants (Table 5). OsDREB1A and OsDREB1B are cold-inducible, but confer tolerance to various abiotic stresses, including drought, when over-expressed in rice and *Arabidopsis* (Dubouzet et al. "OsDREB genes in rice, *Oryza sativa* L., encode transcription activators that function in drought-, high-salt- and cold-responsive gene expression." *The Plant Journal* 33(4), 751-763 (2003) and Ito et al. "Functional analysis of rice DREB1/CBF-type transcription factors involved in cold-responsive gene expression in transgenic rice." *Plant Cell Physiol.* 47(1), 141-153 (2006). Over-expression of OsDREB1E can also improve rice tolerance to drought (Chen et al. "Over-expression of OsDREB genes lead to enhanced drought tolerance in rice." *Biotechnology letters* 30(12), 2191-2198 (2008). In all rice plants tested, OsbHLH148 transcripts were increased by severe dehydration treatments (Seo et al. "OsbHLH148, a basic helix-loop-helix protein, interacts with OsJAZ proteins in a jasmonate signaling pathway leading to drought tolerance in rice." *The Plant Journal* 65(6), 907-921 (2011)). However, moderate drought stress was able to induce the expression of OsbHLH148 in B7-12, but not in A36 plants. In addition, moderate drought stress resulted in a greater accumulation of transcripts encoding the rice DELLA gene SLR1 in A36 than in B7-12.

Example 21. Distinct Water Stresses Induce Different Transcriptomic Alterations in Xa21 Plants The above analysis of selected genes suggested distinct transcriptional responses are triggered by dehydration stress and by moderate drought in the plants expressing heterologous Xa21. This observation was supported by comparing entire DEG datasets from A36 and B7-12 samples. There was a limited number of shared DEGs (61 up-regulated and 72 down-regulated) between air-drying (2215 up-regulated and 1669 down-related) and moderate drought (529 up-regulated, 538 down-related). Gene Ontology (GO) enrichment of DEGs indicated that dehydration treatments altered the levels of transcripts involved in broader biological processes, ranging from photosynthesis to protein modification process. By contrast, in the plants exposed to moderate drought, the significantly enriched GO terms were over-represented by the categories of responses to various stresses and stimuli. Interestingly, Xa21 transcripts were dramatically decreased by dehydration (FIG. 19).

All of the compositions and methods disclosed and claimed herein can be made and executed without undue experimentation in light of the present disclosure. While the compositions and methods of this disclosure have been described in terms of embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

TABLE 2

Summary of RNA-sequencing data

| Sample name | Genotype | Developmental stage | Treatment | Raw Reads | Cleaned reads | GC (%) | read mapping rate in reference (%) | Concordant pair alignment rate (%) |
|---|---|---|---|---|---|---|---|---|
| A36_0.1 | Empty vector/TP309 | 2-week-old seedlings | None (0) | 43,729,273 | 43,644,130 | 52 | 89.60 | 81.6 |
| A36_0.2 | Empty vector/TP309 | 2-week-old seedlings | None (0) | 41,515,844 | 41,445,179 | 52 | 89.60 | 81.90 |
| A36_0.3 | Empty vector/TP309 | 2-week-old seedlings | None (0) | 53,792,634 | 53,712,858 | 52 | 90.60 | 83.10 |
| B7-12_0.1 | 3xFLAG-XA21-Myc/TP309 | 2-week-old seedlings | None (0) | 50,580,748 | 50,482,863 | 52 | 86.60 | 77.20 |
| B7-12_0.2 | 3xFLAG-XA21-Myc/TP309 | 2-week-old seedlings | None (0) | 48,520,459 | 48,423,776 | 52 | 88.70 | 80.60 |
| B7-12_0.3 | 3xFLAG-XA21-Myc/TP309 | 2-week-old seedlings | None (0) | 52,217,212 | 52,118,735 | 52 | 89.60 | 81.70 |
| A36_3.1 | Empty vector/TP309 | 2-week-old seedlings | Air-drying (3 h) | 51,537,030 | 51,443,535 | 52 | 89.60 | 81.90 |
| A36_3.2 | Empty vector/TP309 | 2-week-old seedlings | Air-drying (3 h) | 47,770,273 | 47,673,035 | 52 | 88.80 | 80.60 |
| A36_3.3 | Empty vector/TP309 | 2-week-old seedlings | Air-drying (3 h) | 48,373,866 | 48,262,551 | 52 | 88.10 | 79.40 |
| B7-12_3.1 | 3xFLAG-XA21-Myc/TP309 | 2-week-old seedlings | Air-drying (3 h) | 58,727,386 | 58,606,604 | 53 | 84.80 | 74.20 |
| B7-12_3.2 | 3xFLAG-XA21-Myc/TP309 | 2-week-old seedlings | Air-drying (3 h) | 45,652,457 | 45,563,718 | 52 | 89.50 | 81.70 |
| B7-12_3.3 | 3xFLAG-XA21-Myc/TP309 | 2-week-old seedlings | Air-drying (3 h) | 45,300,340 | 45,227,542 | 52 | 89.30 | 81.30 |
| A36_W.1 | Empty vector/TP309 | 1-month-old plants | Well-watered | 40,215,599 | 40,136,444 | 56 | 83.10 | 74.30 |
| A36_W.2 | Empty vector/TP309 | 1-month-old plants | Well-watered | 44,443,392 | 44,381,768 | 54 | 88.70 | 81.40 |
| A36_W.3 | Empty vector/TP309 | 1-month-old plants | Well-watered | 40,398,852 | 40,367,894 | 50 | 87.10 | 79.30 |
| B7-12_W.1 | 3xFLAG-XA21-Myc/TP309 | 1-month-old plants | Well-watered | 38,755,166 | 38,676,650 | 54 | 83.70 | 73.80 |
| B7-12_W.2 | Empty vector/TP309 | 1-month-old plants | Well-watered | 42,479,420 | 42,421,201 | 54 | 86.50 | 77.90 |
| B7-12_W.3 | 3xFLAG-XA21-Myc/TP309 | 1-month-old plants | Well-watered | 40,089,459 | 40,034,093 | 53 | 87.70 | 79.30 |
| A36_MD.1 | Empty vector/TP309 | 1-month-old plants | Mild drought | 38,297,754 | 38,228,150 | 56 | 85.40 | 77.60 |
| A36_MD.2 | Empty vector/TP309 | 1-month-old plants | Mild drought | 45,759,799 | 45,659,439 | 57 | 83.40 | 74.00 |
| A36_MD.3 | Empty vector/TP309 | 1-month-old plants | Mild drought | 41,641,451 | 41,577,381 | 56 | 85.00 | 75.70 |
| B7-12_MD.1 | 3xFLAG-XA21-Myc/TP309 | 1-month-old plants | Mild drought | 37,541,695 | 37,481,266 | 56 | 84.60 | 76.00 |

TABLE 2-continued

Summary of RNA-sequencing data

| Sample name | Genotype | Developmental stage | Treatment | Raw Reads | Cleaned reads | GC (%) | read mapping rate in reference (%) | Concordant pair alignment rate (%) |
|---|---|---|---|---|---|---|---|---|
| B7-12_MD.2 | Empty vector/TP309 | 1-month-old plants | Mild drought | 41,910,577 | 41,849,015 | 56 | 82.30 | 72.40 |
| B7-12_MD.3 | 3xFLAG-XA21-Myc/TP309 | 1-month-old plants | Mild drought | 39,298,221 | 39,238,739 | 56 | 82.90 | 73.40 |
| Average | | | | 44,939,538 | 44,860,690 | 53.5 | 86.88 | 78.35 |

TABLE 3

List of DEGs related to the DT program between B7-12 and A36 during dehydration.

| | | | Leaf, 3 hpa (B7-12/A36) | | Leaf, 0 hpa (B7-12/A36) | | Leaf, B7-12 (3 hpa/0 hpa) | | Leaf, A36 (3 hpa/0 hpa) | |
|---|---|---|---|---|---|---|---|---|---|---|
| Gene Name | Description | Gene ID | Fold Change | Adj. p-val. | Fold Change | Adj. p-val. | Fold Change | Adj. p-val. | Fold Change | Adj. p-val. |
| *Late embryogenesis abundant proteins (LEAs) (34)* | | | | | | | | | | |
| OsLEA1 | LEA | Os04g49980 | 1.83 | 1.17E−03 | 0.38 | 6.63E−01 | 220.50 | 0 | 46.63 | 0 |
| OsLEA2 | LEA | Os06g02040 | 1.73 | 3.37E−02 | 0.71 | 1.00E+00 | 56.83 | 0 | 23.46 | 1.45E−26 |
| OsLEA3 | LEA | Os06g21910 | 2.09 | 7.10E−03 | 1.34 | 1.00E+00 | | | 88.92 | 1.55E−08 |
| OsLEA4 | LEA | Os08g23870 | 1.88 | 9.24E−05 | 0.86 | 1.00E+00 | 615.64 | 0 | 287.82 | 0 |
| OsLEA5 | LEA | Os01g12580 | 1.79 | 3.81E−04 | 0.65 | 7.05E−01 | 15.75 | 0 | 5.81 | 0 |
| OsLEA11 | LEA | Os03g28260 | 1.39 | 3.41E−02 | 0.58 | 7.08E−01 | 8.37 | 0 | 3.55 | 6.66E−07 |
| OsLEA16 | LEA | Os03g07180 | 1.71 | 2.59E−03 | 0.59 | 1.00E+00 | 16.40 | 9.50E−05 | 5.63 | 3.81E−02 |
| OsLEA17 | LEA | Os03g20680 | 1.71 | 1.33E−08 | 0.55 | 8.27E−01 | 609.38 | 0 | 198.97 | 0 |
| OsLEA18 | LEA | Os04g52110 | 1.47 | 2.13E−02 | 0.51 | 1.00E+00 | 181.40 | 0 | 64.08 | 0 |
| OsLEA19 | LEA | Os05g46480 | 1.63 | 7.11E−04 | 0.57 | 9.70E−01 | 157.44 | 0 | 54.70 | 0 |
| OsLEA21 | LEA | Os05g28210 | 1.63 | 9.18E−03 | 0.16 | 1.00E+00 | 12156.64 | 0 | 1221.44 | 0 |
| OsLEA22 | Dehydrin | Os01g50700 | 2.09 | 3.96E−07 | 1.08 | 1.00E+00 | 51.35 | 0 | 26.65 | 0 |
| OsLEA23 | Dehydrin | Os02g44870 | 1.22 | 3.66E−02 | 0.80 | 1.00E+00 | 48.89 | 0 | 32.56 | 0 |
| OsLEA25 | Dehydrin | Os11g26570 | 1.72 | 3.62E−03 | 0.53 | 8.19E−01 | 193.86 | 0 | 60.28 | 0 |
| OsLEA27 | Dehydrin | Os11g26760 | 1.71 | 1.84E−03 | 0.44 | 1.48E−01 | 88.34 | 0 | 23.18 | 0 |
| OsLEA28 | Dehydrin | Os11g26780 | 1.60 | 1.08E−03 | 0.53 | 6.91E−01 | 294.17 | 0 | 99.21 | 0 |
| OsLEA29 | Dehydrin | Os11g26790 | 1.46 | 3.28E−03 | 0.50 | 8.26E−01 | 81.20 | 0 | 28.29 | 0 |
| OsLEA33 | LEA | Os06g23350 | 1.69 | 2.66E−07 | 0.57 | 1.00E+00 | 414.48 | 0 | 141.66 | 0 |
| *Early light-inducible proteins (ELIP)* | | | | | | | | | | |
| OsELIP1 | ELIP (6)[a] | Os01g14410 | 1.67 | 1.01E−04 | 1.01 | 1.00E+00 | 1.77 | 6.46E−03 | 1.09 | 6.78E−01 |
| OsELIP5 | | Os07g08150 | 2.08 | 7.93E−09 | 0.80 | 1.00E+00 | 2.01 | 1.94E−05 | 0.78 | 3.29E−01 |
| OsELIP6 | | Os07g08160 | 2.14 | 1.11E−04 | 0.68 | 6.98E−01 | 1.94 | 1.88E−03 | 0.62 | 1.87E−02 |
| *Antioxidant defense and detoxification* | | | | | | | | | | |
| OsAPx7 | ascorbate | Os04g35520 | 1.54 | 2.57E−02 | 1.14 | 1.00E+00 | 1.16 | 4.33E−01 | 0.86 | 2.57E−01 |
| OsAPx8 | Peroxidase (8)[a] | Os02g34810 | 1.48 | 1.73E−04 | 1.08 | 1.00E+00 | 1.45 | 7.93E−04 | 1.06 | 6.74E−01 |
| CuZnSOD2 | superoxide | Os03g22810 | 1.62 | 3.17E−08 | 1.82 | 1.61E−07 | 1.29 | 2.96E−03 | 1.46 | 1.13E−04 |
| CuZnSOD3 | dismutase (8)[a] | Os04g48410 | 2.02 | 2.05E−06 | 2.06 | 4.57E−11 | 0.93 | 5.83E−01 | 0.96 | 7.99E−01 |
| CuZnSOD4 | | Os07g46990 | 1.87 | 1.79E−05 | 2.27 | 5.69E−11 | 1.10 | 3.40E−01 | 1.34 | 7.27E−02 |
| CuZnSOD5 | | Os08g44770 | 1.86 | 1.67E−04 | 1.56 | 1.15E−01 | 0.82 | 2.30E−01 | 0.70 | 1.91E−02 |
| OsPrxIIE-2 | peroxiredoxin | Os02g09940 | 1.63 | 3.84E−02 | 1.42 | 8.23E−01 | 0.16 | 0 | 0.14 | 0 |
| OsPrxIIF | (10)[a] | Os01g16152 | 1.41 | 7.58E−04 | 1.32 | 1.04E−01 | 0.98 | 8.23E−01 | 0.92 | 3.74E−01 |
| OsPrxQ | | Os06g09610 | 1.54 | 1.26E−07 | 1.10 | 1.00E+00 | 1.20 | 1.43E−01 | 0.87 | 4.09E−01 |
| Os2-CysPrxA | | Os02g33450 | 1.42 | 3.65E−05 | 1.23 | 6.18E−01 | 0.76 | 2.83E−04 | 0.66 | 3.35E−05 |
| OsGSTF2 | Glutathione | Os01g55830 | 1.36 | 1.29E−04 | 0.94 | 1.00E+00 | 1.34 | 1.98E−04 | 0.94 | 7.12E−01 |
| OsGSTF5 | S-transferase | Os01g27210 | 1.96 | 4.24E−04 | 1.05 | 1.00E+00 | 7.12 | 0 | 3.82 | 0 |
| OsGSTT1 | (79)[a] | Os11g37730 | 2.00 | 1.16E−02 | 0.96 | 1.00E+00 | 3.85 | 0 | 1.86 | 0 |
| OsGSTU18 | | Os10g38580 | 1.97 | 4.60E−05 | 1.02 | 1.00E+00 | 0.28 | 0 | 0.15 | 0 |
| OsGSTU24 | | Os10g38470 | 2.56 | 2.47E−04 | 0.95 | 1.00E+00 | 0.48 | 2.14E−04 | 0.18 | 0 |
| OsGSTU33 | | Os10g22070 | 1.62 | 3.61E−02 | 1.05 | 1.00E+00 | 1.55 | 2.32E−02 | 1.01 | 9.76E−01 |
| OsGSTU38 | | Os06g12290 | 4.43 | 9.30E−13 | 2.07 | 1.00E+00 | 526.12 | 0 | 241.40 | 2.35E−09 |
| OsGSTZ2 | | Os12g10730 | 1.34 | 4.55E−02 | 1.05 | 1.00E+00 | 0.78 | 1.19E−02 | 0.62 | 7.64E−01 |
| OsDHAR2 | | Os06g12630 | 1.31 | 2.03E−03 | 1.13 | 9.38E−01 | 0.80 | 1.79E−02 | 0.70 | 4.60E−06 |
| OsTCHQD1 | | Os04g35560 | 1.69 | 1.02E−12 | 1.17 | 9.75E−01 | 18.72 | 0 | 13.05 | 0 |
| OsGSTF1 b | | Os01g27360 | 0.59 | 3.94E−05 | 0.69 | 2.65E−04 | 1.05 | 6.99E−01 | 1.24 | 4.28E−02 |
| OsGSTU7 b | | Os01g72120 | 0.49 | 1.47E−02 | 0.86 | 1.00E+00 | 1.27 | 4.88E−01 | 2.26 | 2.18E−03 |
| OsGSTU11 b | | Os07g07320 | 0.62 | 1.35E−02 | 0.73 | 1.20E−02 | 0.80 | 2.06E−01 | 0.95 | 7.36E−01 |
| OsGSTU19 b | | Os10g38340 | 0.31 | 2.10E−06 | 0.38 | 5.50E−01 | 1.12 | 8.36E−01 | 1.35 | 3.55E−01 |
| OsGSTU35 b | | Os01g72130 | 0.49 | 7.16E−04 | 0.97 | 1.00E+00 | 1.06 | 7.84E−01 | 2.13 | 8.46E−04 |
| OsGSTU42 b | | Os01g72170 | 0.66 | 8.72E−03 | 0.64 | 4.30E−01 | 0.70 | 5.62E−02 | 0.68 | 3.26E−02 |

TABLE 3-continued

List of DEGs related to the DT program between B7-12 and A36 during dehydration.

| Gene Name | Description | Gene ID | Leaf, 3 hpa (B7-12/A36) | | Leaf, 0 hpa (B7-12/A36) | | Leaf, B7-12 (3 hpa/0 hpa) | | Leaf, A36 (3 hpa/0 hpa) | |
|---|---|---|---|---|---|---|---|---|---|---|
| | | | Fold Change | Adj. p-val. | Fold Change | Adj. p-val. | Fold Change | Adj. p-val. | Fold Change | Adj. p-val. |
| Synthesis of raffinose family oligosaccharides | | | | | | | | | | |
| OsGolS1 | galactinol | Os03g20120 | 1.20 | 3.77E−02 | 0.95 | 1.00E+00 | 56.20 | 0 | 45.08 | 0 |
| OsGolS2 | synthase (2)[a] | Os07g48830 | 1.32 | 1.46E−02 | 0.91 | 1.00E+00 | 56.24 | 0 | 38.96 | 0 |
| Synthesis of sucrose | | | | | | | | | | |
| OsSUS1 | sucrose | Os03g28330 | 2.98 | 6.84E−12 | 2.11 | 7.97E−01 | 0.41 | 3.63E−05 | 0.29 | 9.59E−06 |
| OsSUS4 | synthase (7)[a] | Os03g22120 | 1.66 | 8.32E−06 | 1.11 | 1.00E+00 | 3.06 | 0 | 2.04 | 0 |
| OsSUS6 b | | Os02g58480 | 0.62 | 4.12E−02 | 0.92 | 1.00E+00 | 0.92 | 7.40E−01 | 1.37 | 8.26E−02 |
| Synthesis of octulose | | | | | | | | | | |
| Os07g07470 | transketolase | Os07g07470 | 1.37 | 1.66E−03 | 0.84 | 6.91E−01 | 2.67 | 0 | 1.65 | 7.20E−08 |
| Os12g42230 | | Os12g42230 | 1.30 | 3.51E−02 | 1.04 | 1.00E+00 | 0.92 | 4.18E−01 | 0.74 | 1.74E−03 |

[a] = total number of each family identified in the rice genome

TABLE 4

List of DEGs related to lignin and cellulose biosynthesis between B7-12 and A36 during dehydration

| Gene Name | Description | Gene ID | Leaf, 3 hpa (B7-12/A36) | | Leaf, 0 hpa (B7-12/A36) | | Leaf, B7_12 (3 hpa/0 hpa) | | Leaf, A36 (3 hpa/0 hpa) | |
|---|---|---|---|---|---|---|---|---|---|---|
| | | | Fold Change | Adj. p-val. | Fold Change | Adj. p-val. | Fold Change | Adj. p-val. | Fold Change | Adj. p-val. |
| Synthesis of cellulose | | | | | | | | | | |
| OsCESA1 | Cellulose synthase (CESA) | Os05g08370 | 1.33 | 0.020 | 1.17 | 1.00 | 1.35 | 0.09 | 1.20 | 0.70 |
| OsCESA3 | | Os07g24190 | 1.47 | 0.0033 | 1.30 | 1.00 | 1.08 | 0.70 | 0.97 | 0.91 |
| OsCESA4 | | Os01g54620 | 2.37 | 0.00 | 1.50 | 1.00 | 1.59 | 0.04 | 1.01 | 0.98 |
| OsCESA6 | | Os07g14850 | 1.38 | 0.0061 | 0.81 | 1.00 | 8.83 | 0.00 | 5.23 | 0.00 |
| OsCESA7 | | Os10g32980 | 2.47 | 0.00 | 1.29 | 1.00 | 1.13 | 0.58 | 0.60 | 0.49 |
| OsCESA8 | | Os07g10770 | 1.48 | 0.0011 | 1.20 | 1.00 | 1.38 | 0.11 | 1.13 | 0.69 |
| OsCESA9 | | Os09g25490 | 2.37 | 0.00 | 1.18 | 1.00 | 1.38 | 0.17 | 0.69 | 0.60 |
| Transcription factors related to secondary wall formation | | | | | | | | | | |
| OsPAL1 | Phenylalanine ammonia-lyase (PAL) | Os02g41630 | 1.98 | 0.00 | 1.23 | 1.00 | 1.07 | 0.66 | 0.67 | 0.09 |
| OsSWN1 | Secondary wall NAC domain protein 1 | Os06g04090 | 1.65 | 0.0067 | 1.67 | 0.85 | 1.30 | 0.20 | 1.32 | 0.45 |
| OsMYB55/61 | MYB family | Os01g18240 | 1.46 | 0.050 | 1.35 | 1.00 | 0.64 | 0.04 | 0.60 | 0.10 |
| OsMYB58/63 | MYB family | Os04g50770 | 2.07 | 0.016 | 1.92 | 1.00 | 0.40 | 0.00 | 0.38 | 0.06 |
| OsMYB58/63-L | MYB family | Os02g46780 | 2.31 | 0.036 | 1.63 | 1.00 | 0.81 | 0.55 | 0.58 | 0.39 |
| Synthesis of monolignols | | | | | | | | | | |
| OsPAL1 | Phenylalanine ammonia-lyase (PAL) | Os02g41630 | 1.98 | 0.00 | 1.23 | 1.00 | 1.07 | 0.66 | 0.67 | 0.09 |
| OsPAL4 | | Os02g41680 | 1.59 | 0.0067 | 1.32 | 1.00 | 1.47 | 0.02 | 1.24 | 0.75 |
| OsPAL9 | | Os12g33610 | 1.32 | 0.014 | 1.23 | 0.93 | 0.42 | 0.00 | 0.40 | 0.00 |
| Os4CL3 | | Os02g08100 | 1.57 | 0.000027 | 1.20 | 1.00 | 2.17 | 0.00 | 1.68 | 0.03 |
| Os4CL4 | | Os06g44620 | 1.30 | 0.021 | 1.00 | 1.00 | 2.56 | 0.00 | 1.98 | 0.00 |
| Snl6 (OsCCR2) | Cinnamoyl CoA reductase (CCR) | Os01g45200 | 1.56 | 0.0013 | 0.89 | 1.00 | 4.48 | 0.00 | 2.57 | 0.00 |
| OsCCR19 | | Os09g25150 | 0.81 | 0.019 | 0.73 | 0.0084 | 1.22 | 0.02 | 1.11 | 0.15 |
| OsCCR20 | | Os08g34280 | 1.46 | 0.0029 | 1.04 | 1.00 | 1.19 | 0.27 | 0.85 | 0.75 |
| OsCCR22 | | Os03g60380 | 1.65 | 0.000096 | 1.09 | 1.00 | 15.04 | 0.00 | 9.97 | 0.00 |
| OsCCR23 (Snl6-like) | | Os05g50250 | 1.72 | 0.0027 | 1.31 | 0.98 | 4.48 | 0.00 | 3.42 | 0.00 |
| OsCAld5H1 | Coniferaldehyde 5-hydroxylase (ferulate 5-hydroxylase) (F5H) | Os10g36848 | 3.26 | 0.000081 | 0.98 | 1.00 | 1.63 | 0.09 | 0.49 | 0.09 |
| OsCAldOMT1 | Caffeic acid o-methyl-transferase (ROMT9, OsCOMT1) | OS08g06100 | 1.75 | 0.00 | 1.17 | 1.00 | 0.73 | 0.03 | 0.49 | 0.00 |

TABLE 4-continued

List of DEGs related to lignin and cellulose biosynthesis between B7-12 and A36 during dehydration

| Gene Name | Description | Gene ID | Leaf, 3 hpa (B7-12/A36) Fold Change | Adj. p-val. | Leaf, 0 hpa (B7-12/A36) Fold Change | Adj. p-val. | Leaf, B7_12 (3 hpa/0 hpa) Fold Change | Adj. p-val. | Leaf, A36 (3 hpa/0 hpa) Fold Change | Adj. p-val. |
|---|---|---|---|---|---|---|---|---|---|---|
| OsCAD2 (GH2) | Cinnamyl alcohol dehydrogenase (CAD) | Os02g09490 | 1.56 | 0.0045 | 1.09 | 1.00 | 2.24 | 0.00 | 1.57 | 0.08 |
| Synthesis of tricin | | | | | | | | | | |
| OsCHS1/ OsPKS26 | Chalcone synthase (type III polyketide synthase) | Os11g32650 | 1.49 | 0.00048 | 1.08 | 1.00 | 1.36 | 0.04 | 1.00 | 1.00 |
| OsPKS27 | | Os11g35930 | 8.42 | 0.00072 | 2.11 | 1.00 | 0.65 | 0.38 | 0.16 | 0.05 |
| OsFNSII (CYP93G) | | Os04g01140 | 2.72 | 0.00 | 1.25 | 1.00 | | 0.00 | 0.26 | 0.00 |
| CYP75B4 | flavonoid 3'-hydroxylase (F3'H) | Os10g16974 | 2.36 | 0.00 | 1.33 | 1.00 | 1.14 | 0.54 | 0.65 | 0.36 |
| OsCAldOMT1 | Caffeic acid o-methyl-transferase (ROMT9, OsCOMT1) | Os08g06100 | 1.75 | 0.000 | 1.17 | 1.00 | 0.73 | 0.03 | 0.49 | 0.00 |
| Assembly of lignin | | | | | | | | | | |
| OsLAC4 | | Os01g62480 | 2.38 | 0.0017 | 1.33 | 1.00 | 0.22 | 0.00 | 0.12 | 0.016 |
| OsLAC5 | | Os01g62490 | 2.10 | 0.040 | 0.75 | 1.00 | 0.47 | 0.00 | 0.17 | 0.030 |
| OsLAC8 | | Os01g63190 | 2.21 | 0.00 | 1.16 | 1.00 | 1.07 | 0.70 | 0.57 | 0.033 |
| OsLAC28 | | Os12g15530 | 2.76 | 0.044 | 0.44 | 1.00 | 9.04 | 0.00 | 1.47 | 0.64 |
| OsPrx3 | Class III peroxidase | Os01g15830 | 3.16 | 0.0061 | 1.79 | 0.65 | 0.84 | 0.64 | 0.48 | 0.044 |
| OsPrx11 | | Os01g19020 | 1.64 | 0.00 | 1.01 | 1.00 | 1.26 | 0.25 | 0.79 | 0.61 |
| OsPrx12 | | Os01g22230 | 2.49 | 0.0010 | 1.38 | 1.00 | 1.72 | 0.020 | 0.97 | 0.94 |
| OsPrx15 | | Os01g22352 | 2.04 | 0.00 | 1.17 | 1.00 | 2.66 | 0.00 | 1.54 | 0.0073 |
| OsPrx16 | | Os01g22370 | 1.74 | 0.00 | 1.03 | 1.00 | 2.02 | 0.00 | 1.21 | 0.48 |
| OsPrx22 | | Os01g73200 | 1.78 | 0.0096 | 1.35 | 0.97 | 1.81 | 0.16 | 1.39 | 0.060 |
| OsPrx29 | | Os02g14440 | 1.57 | 0.033 | 1.00 | 1.00 | 0.22 | 0.00 | 0.14 | 0.00 |
| OsPrx39 | | Os03g13200 | 5.07 | 0.00026 | 3.93 | 0.71 | 2.20 | 0.19 | 1.71 | 0.42 |
| OsPrx45 | | Os03g25330 | 4.17 | 0.0061 | 1.11 | 1.00 | 1.52 | 0.33 | 0.41 | 0.16 |
| OsPrx65 | | Os05g04380 | 2.33 | 0.00 | 1.17 | 1.00 | 1.39 | 0.075 | 0.70 | 0.53 |
| OsPrx71 | | Os05g04500 | 4.32 | 0.00 | 1.65 | 1.00 | 1.07 | 0.80 | 0.41 | 0.16 |
| OsPrx74 | | Os05g41990 | 2.30 | 0.0025 | 0.82 | 1.00 | 13.23 | 0.00 | 4.75 | 0.00064 |
| OsPrx97 | | Os07g01370 | 5.55 | 0.016 | 1.52 | 1.00 | 0.64 | 0.31 | 0.18 | 0.040 |
| OsPrx117 | | Os08g02110 | 10.47 | 0.0084 | 0.73 | 1.00 | 0.058 | 0.00052 | 0.00 | 0.00 |
| OsPrx125 | | Os10g02040 | 2.26 | 0.00 | 1.31 | 0.97 | 1.47 | 0.063 | 0.86 | 0.44 |
| OsPrx130 | | Os11g02130 | 1.64 | 0.0092 | 1.58 | 1.00 | 20.46 | 0.00 | 19.90 | 0.00 |
| OsPrx135 | | Os12g02080 | 1.56 | 0.00027 | 0.80 | 1.00 | 24.42 | 0.00 | 12.65 | 0.00 |
| OsPrx50 | | Os03g55410 | 0.56 | 0.0083 | 0.74 | 0.85 | 0.13 | 0.00 | 0.18 | 0.00 |
| OsDIR9 | Dirigent protein | Os04g57130 | 2.40 | 0.0060 | 2.29 | 1.00 | 28.84 | 0.00 | 27.46 | 0.00 |
| OsDIR10 | | Os07g01600 | 3.23 | 0.00 | 1.64 | 0.96 | 1.43 | 0.19 | 0.73 | 0.53 |
| OsDIR16 | | Os07g44250 | 4.90 | 0.022 | 3.08 | 0.11 | 0.42 | 0.02 | 0.26 | 0.038 |
| OsDIR26 | | Os08g28790 | 1.81 | 0.00035 | 0.82 | 1.00 | 1.22 | 0.42 | 0.56 | 0.35 |
| OsDIR44 | | Os11g42500 | 4.29 | 0.000 | 1.76 | 1.00 | 0.34 | 0.18 | 0.14 | 0.00 |
| OsDIR45 | | Os11g42550 | 3.93 | 0.000 | 1.96 | 1.00 | 3.70 | 0.18 | 1.85 | 0.50 |

TABLE 5

List of DEGs related to OsbHLH148-regulated OsJAZ and OsDREB1 family members between B7-12 and A36 during moderate drought.

| Gene Name (Ye et al., 2009) | Gene Name (Seo et al., 2011) | Description | Gene ID | Leaf, one month mild drought (MD) B7-12/A36 Fold Change | Adj. p-val | Leaf, one month well-watered (W) B7-12/A36 Fold Change | Adj. p-val | Leaf, one month B7-12_MD/ A36_W Fold Change | Adj. p-val | Leaf, one month B7-12_MD/ A36_W Fold Change | Adj. p-val |
|---|---|---|---|---|---|---|---|---|---|---|---|
| OsbHLH148 | OsbHLH148 | basic helix-loop-helix protein | OS03g53020 | 3.39 | 0.00 | 1.08 | 1.00 | 2.26 | 0.090 | 0.72 | 0.51 |
| OsJAZ1/ OsTIFY3 | OsJAZ10 | JASMONATE-ZIM-DOMAIN Protein | Os04g55920/ AK059441 | 1.42 | 0.027 | 1.18 | 1.00 | 1.18 | 0.69 | 0.98 | 0.96 |
| OsJAZ4/ OsTIFY6b | OsJAZ8 | JASMONATE-ZIM-DOMAIN Protein | Os09g23660/ AK065170 | 1.93 | 0.0002 | 0.98 | 1.00 | 0.88 | 0.83 | 0.48 | 0.21 |
| OsJAZ6/ OsTIFY10a | OsJAZ5 | JASMONATE-ZIM-DOMAIN Protein | Os03g28940/ AK061842 | 4.20 | 0.00 | 1.78 | 1.00 | 1.59 | 0.66 | 0.64 | 0.29 |
| OsJAZ7/ OsTIFY10b | OsJAZ6 | JASMONATE-ZIM-DOMAIN Protein | Os07g42370/ AK065604 | 2.68 | 0.00 | 1.51 | 1.00 | 1.51 | 0.47 | 0.88 | 0.80 |

TABLE 5-continued

List of DEGs related to OsbHLH148-regulated OsJAZ and OsDREB1 family members between B7-12 and A36 during moderate drought.

| Gene Name (Ye et al., 2009) | Gene Name (Seo et al., 2011) | Description | Gene ID | Leaf, one month mild drought (MD) B7-12/A36 | | Leaf, one month well-watered (W) B7-12/A36 | | Leaf, one month B7-12_MD/ A36_W | | Leaf, one month B7-12_MD/ A36_W | |
|---|---|---|---|---|---|---|---|---|---|---|---|
| | | | | Fold Change | Adj. p-val | Fold Change | Adj. p-val | Fold Change | Adj. p-val | Fold Change | Adj. p-val |
| OsJAZ9/ OsTIFY11a | OsJAZ3 | JASMONATE-ZIM-DOMAIN Protein | Os03g08310/ AK070649 | 41.38 | 0.00 | 3.85 | 1.00 | 7.43 | 0.054 | 0.52 | NA |
| OsJAZ10/ OsTIFY11b | OsJAZ4 | JASMONATE-ZIM-DOMAIN Protein | Os03g08330/ AK120087 | 33.85 | 0.0073 | 6.10 | 1.00 | 5.11 | 0.43 | 0.74 | 0.80 |
| OsJAZ11/ OsTIFY11c | OsJAZ2 | JASMONATE-ZIM-DOMAIN Protein | Os03g08320/ AK073589 | 16.11 | 0.0002 | 0.92 | 1.00 | 3.63 | 0.18 | 0.20 | 0.11 |
| OsJAZ12/ OsTIFY11d | OsJAZ1 | JASMONATE-ZIM-DOMAIN Protein | Os10g25290/ AK061602 | 13.20 | 0.0001 | 2.68 | 1.00 | 3.58 | 0.60 | 0.65 | 0.63 |
| OsDREB1A | | AP2 transcription factor | Os09g35030/ AF300970 | 6.66 | 0.00 | 0.49 | 1.00 | 14.50 | 0.00 | 1.11 | 0.92 |
| OsDREB1B | | AP2 transcription factor | Os09g35010/ AF300972 | 9.25 | 0.00 | 1.71 | 1.00 | 14.45 | 0.00 | 2.56 | 0.33 |
| OsDREB1C | | AP2 transcription factor | Os06g03670/ AY327040 | 5.76 | 0.031 | 1.27 | 1.00 | 9.77 | 0.024 | 3.72 | NA |
| OsDREB1E | | AP2 transcription factor | Os04g48350/ AY114110 | 20.71 | 0.017 | 0.44 | 1.00 | 29.51 | 0.025 | N/A | NA |
| OsDREB1H | | AP2 transcription factor | Os09g35020 | 17.35 | 0.0013 | 2.23 | 1.00 | 11.57 | 0.009 | 0.99 | NA |

Nomenclature used by Ye et al. (2009) to describe OsJAZs.

---

What is claimed is:

1. A method of increasing drought tolerance in a plant, the method comprising expressing a heterologous receptor kinase Xa21 coding region that encodes a polypeptide sharing at least 95% identity to SEQ ID NO: 2 in one or more plants thereby overexpressing Xa21 in the plants and selecting one or more plants for increased drought resistance as compared to a control plant grown under the same conditions that lacks the heterologous Xa21 coding region.

2. The method of claim 1, wherein said expressing comprises introducing into the plant a DNA construct comprising said heterologous receptor kinase Xa21 coding region operably linked to a receptor kinase Xa21 promoter.

3. The method of claim 1, wherein said expressing comprises introducing into the plant a DNA construct comprising said heterologous receptor kinase Xa21 coding region operably linked to a heterologous promoter functional in the plant.

4. The method of claim 3, wherein the promoter is a constitutive or inducible promoter.

5. The method of claim 1, wherein said heterologous receptor kinase Xa21 coding region encodes a protein having the amino acid sequence of SEQ ID NO: 2.

6. The method of claim 1, wherein said heterologous receptor kinase Xa21 coding region shares at least 90% identical to SEQ ID NO: 1.

7. The method of claim 5, wherein said heterologous receptor kinase Xa21 coding region shares at least 95% identical to SEQ ID NO: 1.

8. The method of claim 1, wherein the plant is a monocotyledonous plant.

9. The method of claim 8, wherein the monocotyledonous plant is selected from the group consisting of maize, wheat, rice, sorghum, Sorghum bicolor, oats, barley, sugar cane, African oil palm, Elaeis guineensis, and switchgrass.

10. The method of claim 1, wherein the plant is a dicotyledonous plant.

11. The method of claim 10, wherein the dicotyledonous plant is selected from the group consisting of Arabidopsis, peanut, Arachis hypogaea, barrel medic, Medicago truncatula, carrot, soybean, Glycine max, cotton, Brassica, canola, tomato, potato, alfalfa, grape, clover, poplar, willow, eucalyptus, hemp, a Lotus sp., a Vinca sp., a Nicotiana sp., a Vitis sp., and a Ricinus sp.

12. A method of producing food for human or animal consumption, the method comprising:
   a) increasing drought tolerance in a plant by expressing a heterologous receptor kinase Xa21 coding region that encodes a polypeptide sharing at least 95% identity to SEQ ID NO: 2 in one or more plants thereby overexpressing Xa21 in the plants and selecting one or more plants for increased drought resistance as compared to a control plant grown under the same conditions that lacks the heterologous Xa21 coding region; and
   b) preparing food for human or animal consumption from the plant or a part thereof.

13. The method of claim 12, wherein the food is starch, protein, meal, flour or grain.

14. The method of claim 1, wherein the plant is a rice plant.

15. A method of producing a drought tolerant plant, the method comprising crossing a first plant expressing a heterologous receptor kinase Xa21 coding region that encodes a polypeptide sharing at least 95% identity to SEQ ID NO: 2 thereby overexpressing Xa21 in the plant with a second plant, and selecting at least a first progeny plant expressing the heterologous Xa21 coding region for increased drought tolerance when compared to a control plant grown under the same conditions that lacks the heterologous Xa21 coding region.

16. The method of claim 15, wherein said drought tolerant plant is a drought tolerant rice plant.

17. The method of claim 15 wherein the heterologous receptor kinase Xa21 coding region is operably linked to a promoter.

18. The method of claim 17, wherein said promoter is a drought-inducible promoter.

19. A method for improving plant growth during moderate drought, the method comprising expressing a heterologous Xa21 coding region that encodes a polypeptide sharing at least 95% identity to SEQ ID NO: 2 in one or more plants thereby overexpressing Xa21 in the one or more plants and selecting one or more plants for increased plant growth during moderate drought as compared to a control plant grown under the same conditions that lacks the heterologous Xa21 coding region.

20. A method of increasing drought tolerance in a plant, the method comprising expressing a heterologous receptor kinase Xa21 coding region that encodes a polypeptide sharing at least 95% identity to SEQ ID NO: 2 in one or more plants thereby overexpressing Xa21 in the plants, subjecting the one or more plants to a drought condition, and selecting one or more plants for one or more of: increased drought survival; increased expression of one or more genes related to desiccation tolerance, biosynthesis of cell walls, and/or transcellular water movement; increased deposition of lignin and cellulose in the xylem vessels and/or their surrounding cells; decreased xylem wall collapse and/or decreased embolism formation in xylem; and improved xylem functionality when compared to a control plant grown under the same conditions that lacks the heterologous Xa21 coding region.

* * * * *